(12) United States Patent
Shao et al.

(10) Patent No.: US 11,826,471 B2
(45) Date of Patent: *Nov. 28, 2023

(54) COMPOSITIONS COMPRISING PGI2-RECEPTOR AGONISTS AND PROCESSES FOR THE PREPARATION THEREOF

(71) Applicant: Arena Pharmaceuticals, Inc., San Diego, CA (US)

(72) Inventors: Zezhi Jesse Shao, San Diego, CA (US); Raizza Berania Florida, Escondido, CA (US); Ching-Yuan Li, San Diego, CA (US); Lee Alani Selvey, Longview, WA (US)

(73) Assignee: ARENA PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/400,957

(22) Filed: Aug. 12, 2021

(65) Prior Publication Data

US 2021/0378965 A1 Dec. 9, 2021

Related U.S. Application Data

(63) Continuation of application No. 16/386,183, filed on Apr. 16, 2019, now Pat. No. 11,123,298, which is a continuation of application No. PCT/US2018/020519, filed on Mar. 1, 2018.

(60) Provisional application No. 62/530,515, filed on Jul. 10, 2017, provisional application No. 62/526,039, filed on Jun. 28, 2017, provisional application No. 62/468,832, filed on Mar. 8, 2017, provisional application No. 62/465,675, filed on Mar. 1, 2017.

(51) Int. Cl.
| | | |
|---|---|---|
| *A61K 9/20* | (2006.01) | |
| *A61K 31/27* | (2006.01) | |
| *A61K 9/16* | (2006.01) | |
| *A61K 9/28* | (2006.01) | |
| *A61K 9/48* | (2006.01) | |

(52) U.S. Cl.
CPC .......... *A61K 9/2054* (2013.01); *A61K 9/1617* (2013.01); *A61K 9/1623* (2013.01); *A61K 9/1641* (2013.01); *A61K 9/1652* (2013.01); *A61K 9/2009* (2013.01); *A61K 9/2013* (2013.01); *A61K 9/2018* (2013.01); *A61K 9/28* (2013.01); *A61K 9/284* (2013.01); *A61K 9/48* (2013.01); *A61K 9/4825* (2013.01); *A61K 9/4858* (2013.01); *A61K 9/4866* (2013.01); *A61K 31/27* (2013.01)

(58) Field of Classification Search
CPC ....... A61K 9/2018; A61K 9/28; A61K 9/4858
See application file for complete search history.

(56) References Cited

U.S. PATENT DOCUMENTS

| | | |
|---|---|---|
| 5,558,071 A | 9/1996 | Ward et al. |
| 5,849,919 A | 12/1998 | Hamanaka et al. |
| 6,579,851 B2 | 6/2003 | Goeke et al. |
| 6,746,729 B1 | 6/2004 | Cherkaoui et al. |
| 7,115,746 B2 | 10/2006 | Snoonian et al. |
| 7,202,253 B2 | 4/2007 | Lloyd et al. |
| 7,226,550 B2 | 6/2007 | Hou et al. |
| 8,461,129 B2 | 6/2013 | Bolduc et al. |
| 8,895,776 B2 | 11/2014 | Tran et al. |
| 10,537,546 B2 | 1/2020 | Glicklich |
| 10,668,033 B2 | 6/2020 | Tran et al. |
| 10,688,076 B2 | 6/2020 | Glicklich |
| 11,000,500 B2 | 5/2021 | Glicklich |
| 2003/0144350 A1 | 7/2003 | Stevenson et al. |
| 2004/0048844 A1 | 3/2004 | Nugiel et al. |
| 2006/0063930 A1 | 3/2006 | Agoston et al. |
| 2006/0258728 A1 | 11/2006 | Tani et al. |
| 2008/0139655 A1* | 6/2008 | Bortz ................ A61P 25/16 514/563 |

(Continued)

FOREIGN PATENT DOCUMENTS

| | | |
|---|---|---|
| CA | 2125074 A1 | 12/1994 |
| CN | 1418187 A | 5/2003 |

(Continued)

OTHER PUBLICATIONS

ADEMPAS® product information. Available at https://www.adempas-us.com/ (2 pgs.) (2019).
Aguilar et al. Epoprostenol (prostacyclin) therapy in HIV-associated pulmonary hypertension. Am. J. Respir. Crit. Care Med. 162:1846-1850 (2000).
Archer et al., Nitric oxide deficiency in fenfluramine- and dexfenfluramine-induced pulmonary hypertension. Am. J. Respir. Crit. Care Med. 158:1061-1067 (1998).
Arehart et al., Acceleration of cardiovascular disease by a dysfunctional prostacyclin receptor mutation: potential implications for cyclooxygenase-2 inhibition. Circ. Res. 102(8):986-993 (2008).
Arehart et al., Prostacyclin, atherothrombosis, and cardiovascular disease. Curr. Med. Chem. 14:2161-2169 (2007).

(Continued)

*Primary Examiner* — Andrew S Rosenthal
(74) *Attorney, Agent, or Firm* — WILSON SONSINI GOODRICH & ROSATI

(57) ABSTRACT

Provided herein in some embodiments are pharmaceutical compositions comprising a prostacyclin (PGI2) receptor agonist selected from 2-(((1r,4r)-4-(((4-chlorophenyl)(phenyl)carbamoyloxy)methyl)cyclohexyl)methoxy)acetic acid (Compound 1) and pharmaceutically acceptable salts, solvates, and hydrates thereof, as disclosed herein. In some embodiments the pharmaceutical compositions comprise a compound selected from 2-(((1r,4r)-4-(((4-chlorophenyl)(phenyl)carbamoyloxy)methyl)cyclohexyl)methoxy)acetic acid (Compound 1), and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c) as disclosed herein. The compositions of the present invention are useful in the treatment of PGI2 related disorders, such as those disclosed herein.

25 Claims, 20 Drawing Sheets

(56) References Cited

U.S. PATENT DOCUMENTS

| | | |
|---|---|---|
| 2011/0028412 A1 | 2/2011 | Cappello et al. |
| 2011/0053958 A1 | 3/2011 | Tran et al. |
| 2011/0224262 A1 | 9/2011 | Tran et al. |
| 2011/0245251 A1 | 10/2011 | Tran et al. |
| 2012/0225937 A1 | 9/2012 | Blackburn et al. |
| 2013/0041004 A1 | 2/2013 | Drager et al. |
| 2013/0084243 A1 | 4/2013 | Goetsch et al. |
| 2013/0096073 A1 | 4/2013 | Sidelman |
| 2013/0217706 A1 | 8/2013 | Tran et al. |
| 2015/0126527 A1 | 5/2015 | Tran et al. |
| 2019/0321328 A1 | 10/2019 | Behan et al. |

FOREIGN PATENT DOCUMENTS

| | | |
|---|---|---|
| CN | 1516690 A | 7/2004 |
| CN | 1735598 A | 2/2006 |
| CN | 1822808 A | 8/2006 |
| CN | 1829712 A | 9/2006 |
| CN | 1882532 A | 12/2006 |
| EA | 200000012 A1 | 8/2000 |
| EP | 0028829 A1 | 5/1981 |
| EP | 0442448 A2 | 8/1991 |
| EP | 1013639 A1 | 6/2000 |
| EP | 1046631 A1 | 10/2000 |
| EP | 1716087 A1 | 11/2006 |
| JP | H03160438 A | 7/1991 |
| JP | H06329598 A | 11/1994 |
| JP | H11269138 A | 10/1999 |
| JP | 2005104853 A | 4/2005 |
| JP | 2006083085 A | 3/2006 |
| JP | 2006137856 A | 6/2006 |
| JP | 2007161867 A | 6/2007 |
| JP | 2010539117 A | 12/2010 |
| JP | 2011515396 A | 5/2011 |
| JP | 2014210774 A | 11/2014 |
| JP | 2016028062 A | 2/2016 |
| JP | 2018035194 A | 3/2018 |
| WO | WO-9524393 A1 | 9/1995 |
| WO | WO-02055484 A1 | 7/2002 |
| WO | WO-2007051255 A1 | 5/2007 |
| WO | WO-2007133653 A2 | 11/2007 |
| WO | WO-2009117095 A1 * | 9/2009 ............ A61K 31/17 |
| WO | WO-2010077275 A1 | 7/2010 |
| WO | WO-2011037613 A1 | 3/2011 |
| WO | WO-2016065103 A1 | 4/2016 |
| WO | WO-2018089804 A1 | 5/2018 |
| WO | WO-2018160882 A1 | 9/2018 |
| WO | WO-2019222764 A1 | 11/2019 |

OTHER PUBLICATIONS

Asada et al., Discovery of a series of acrylic acids and their derivatives as chemical leads for selective EP3 receptor antagonists, Bioorganic & Medicinal Chemistry, Pergamon, GB 17(18):6567-6582 (2009).

ATS Committee on Proficiency Standards for Clinical Pulmonary Function Laboratories. ATS statement: guidelines for the six-minute walk test. Am J Respir Crit Care Med. 166(1):111-117 (2002).

ATS statement: guidelines for the six-minute walk test. ATS Committee on Proficiency Standards for Clinical Pulmonary Function Laboratories. Am J Respir 166(1):111-117 (2002).

Badesch et al., Continuous intravenous epoprostenol for pulmonary hypertension due to the scleroderma spectrum of disease. A randomized, controlled trial. Ann. Intern. Med. 132:425-434 (2000).

Badesch et al., Prostanoid therapy for pulmonary arterial hypertension. Journal of the American College of Cardiology 43(12 Suppl. S):56S-61S (2004).

Baliga et al. New perspectives for the treatment of pulmonary hypertension. Br J Pharmacol 163(1):125-140 (2011).

Baradia et al., Inhalation therapy to treat pulmonary arterial hypertension. Pharm. Pat. Analyst 1(5):577-588 (2012).

Berge et al. Pharmaceutical Salts. Journal of Pharmaceutical Sciences 66(1):1-19 (Jan. 1977).

Bernabei et al., Iloprost and echistatin protect platelets during simulated extracorporeal circulation. Ann. Thorac. Surg. 59:149-153 (1995).

BioWorld Today 22(133):1-7 URL: http://epozyme.com/pdf/bwt07132011.pdf (Jul. 13, 2011) (7 pgs).

Boehme et al., Decrease in circulating endothelial cell adhesion molecule and thrombomodulin levels during oral iloprost treatment in rheumatoid arthritis patients: preliminary results. Rheumatol. Int. 26:340-347 (2006).

Burnette et al. PGI2 opens potassium channels in retinal pericytes by cyclic AMP-stimulated, cross-activation of PKG. Exp. Eye Res. 83:1359-1365 (2006).

Cameron et al., The effects of 5-hydroxytryptamine 5-HT2 receptor antagonists on nerve conduction velocity and endoneurial perfusion in diabetic rats. Naunyn Schmiedebergs Arch. Pharmacol. 367:607-614 (2003).

Cameron. Vascular factors and metabolic interactions in the pathogenesis of diabetic neuropathy. Diabetologia 44:1973-1988 (2001).

Caojin et al, Comparison of acute hemodynamic effects of aerosolized iloprost and inhaled nitric oxide in adult congenital heart disease with severe pulmonary arterial hypertension. Department of Cardiology, Guangdong General Hospital & Guangdong Cardiovascular Institute, China, Intern Med. 51:2857-2862 (2012).

Cheng et al., Role of prostacyclin in the cardiovascular response to thromboxane A2. Science 296:539-541 (2002).

Chin et al. Long-term therapy with oral treprostinil in pulmonary arterial hypertension failed to lead to improvement in important physiologic measures: results from a single center. Pulm Circ 5(3):513-520 (2015).

Clapp et al. Phosphodiesterase-type 3 inhibitor potentiates cAMP generation and antiproliferative effects of treprostinil in pulmonary arterial smooth muscle cells from patients with pulmonary hypertension. Presented at: ERS Annual Congress 2010.

Clinical Trials—Cancer. Genetic Engineering and Biotechnology News 32(20):54 (Nov. 15, 2012).

Collier et al, Radiosynthesis and in vivo evaluation of the pseudopeptide δ-opioid antagonist [125I]-ITIPP(ψ) J. Labelled Compd. Radiopharm 42:S264-S266 (1999).

Cote et al., Disruption of the nonneuronal tph1 gene demonstrates the importance of peripheral serotonin in cardiac function. PNAS 100(23):13525-13530 (2003).

Cotter et al., Prevention and reversal of motor and sensory peripheral nerve conduction abnormalities in streptozotocin-diabetic rats by the prostacyclin analogue iloprost. Naunyn Schmiedebergs Arch. Pharmacol. 347:534-540 (1993).

Czeslick et al., Inhibition of intracellular tumour necrosis factor (TNF)-alpha and interleukin (IL)-6 production in human monocytes by iloprost. Eur. J. Clin. Invest. 33:1013-1017 (2003).

Davi et al, Platelet activation and atherothrombosis. N. Eng. J. Med. 357:2482-2494 (2007).

Di Renzo et al., Iloprost treatment reduces TNF-alpha production and TNF-RII expression in critical limb ischemia patients without affecting IL6. Prostaglandin Leukot. Essent. Fatty Acids 73:405-410 (2005).

Dogan et al., Effect of the prostacyclin analogue, iloprost, on infarct size after permanent focal cerebral ischemia. Gen. Pharmacol. 27:1163-1166 (1996).

Driscoll et al., Medical therapy for pulmonary arterial hypertension. Expert Opin. Pharmacother. 9:65-81 (2008).

Drogalis-Kim et al., Right sided heart failure and pulmonary hypertension: New insights into disease mechanisms and treatment modalities. Progress in Pediatric Cardiology 43:71-80 (2016).

Drugs in Japan. Ethical Drugs 2008:2336-2337 (2009).

Egan et al., COX-2-derived prostacyclin confers atheroprotection on female mice. Science 306:1954-1957 (2004).

Fang et al, Induction of prostacyclin/PGI2 synthase expression after cerebral ischemia-reperfusion. J. Cereb. Blood Flow Metab. 26:491-501 (2006).

Farber et al., Practical considerations for therapies targeting the prostacyclin pathway. European Respiratory Review 25(142):418-430 (2016).

(56) References Cited

OTHER PUBLICATIONS

Fetalvero et al., Cardioprotective prostacyclin signaling in vascular smooth muscle. Prostaglandins Other Lipid Mediat. 82:109-118 (2007).
Fetalvero et al., The prostacyclin receptor induces human vascular smooth muscle cell differentiation via the protein kinase A pathway. Am. J. Physiol. Heart. Circ. Physiol. 290:H1337-H1346 (2006).
Fujiwara et al., A stable prostacyclin analogue reduces high serum TNF-alpha levels in diabetic patients. Exp. Clin. Endocrinol. Diabetes 112:390-394 (2004).
Gabriel et al., High throughput screening technologies for direct cyclic AMP measurement. ASSAY and Drug Development Technologies, 1:291-303 (2003).
Gainza et al., Role of prostacyclin (epoprostenol) as anticoagulant in continuous renal replacement therapies: efficacy, security and cost analysis. J. Nephrol. 19:648-655 (2006).
Galie et al. The use of combination therapy in pulmonary arterial hypertension: new developments. Eur Respir Rev 18(113):148-153 (2009).
Gao et al., A 7-day oral treatment of patients with active rheumatoid arthritis using the prostacyclin analog iloprost: cytokine modulation, safety, and clinical effects. Rheumatol. Int. 22:45-51 (2002).
Ghofrani et al. Riociguat for the Treatment of Pulmonary Arterial Hypertension. N Engl J Med 369(4):330-40 (Jul. 25, 2013).
Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Harada et al., Role of neutrophil elastase in development of pulmonary vascular injury and septic shock in rats. Shock 30(4):379-387 (2008).
Hattori et al. Discovery of diphenylcarbamate derivatives as highly potent and selective IP receptor agonists: orally active prostacyclin mimetics. Part 3. Bioorg Med Chem Lett 15:3091-3095 (2005).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Hoeper et al., Bosentan therapy for portopulmonary hypertension. Eur. Respir. J. 25:502-508 (2005).
Hoeper et al., Pulmonary hypertension after splenectomy? Ann. Intern. Med. 130(6):506-509 (1999).
Hotta et al, Effects of beraprost sodium and insulin on the electroretinogram, nerve conduction, and nerve blood flow in rats with streptozotocin-induced diabetes. Diabetes 45:361-366 (1996).
Hotta et al. Prevention of abnormalities in motor nerve conduction and nerve blood-flow by a prostacyclin analog, beraprost sodium, in streptozotocin-induced diabetic rats. Prostaglandins 49:339-349 (1995).
Hoyng et al., Iloprost, a stable prostacyclin analog, reduces intraocular pressure. Invest. Ophthalmol Vis. Sci. 28:470-476 (1987).
Humbert et al., Cellular and molecular pathobiology of pulmonary arterial hypertension. J. Am. Coll. Cardiol. 43:13S-24S (2004).
Humbert et al, Short-term and long-term epoprostenol (prostacyclin) therapy in pulmonary hypertension secondary to connective tissue diseases: results of a pilot study Eur. Respir. J. 13:1351-1356 (1999).
Idzko et al, Inhaled iloprost suppresses the cardinal features of asthma via inhibition of airway dendritic cell function. J. Clin. Invest. 117:464-472 (2007).
Jaffar et al., Prostaglandin I2-IP signaling blocks allergic pulmonary inflammation by preventing recruitment of CD4+ Th2 cells into the airways in a mouse model of asthma. J. Immunol 179:6193-6203 (2007).
Jozefowski et al., Exogenous but not endogenous prostanoids regulate cytokine secretion from murine bone marrow dendritic cells: EP2, DP, and IP but not EP1, EP3, and FP prostanoid receptors are involved. Int. Immunopharmcol. 3:865-878 (2003).
Klapars et al., A general and efficient copper catalyst for the amidation of aryl halides. J. Am. Chem. Soc. 124: 7421-7428 (2002).
Kobayashi et al., Roles of thromboxane A(2) and prostacyclin in the development of atherosclerosis in apoE-deficient mice. J. Clin. Invest. 114:784-794 (2004).
Koike et al., Enhanced angiogenesis and improvement of neuropathy by cotransfection of human hepatocyte growth factor and prostacyclin synthase gene. FASEB J. 17:779-781 (2003).
Le Bas et al., Radioiodinated analogs of EP 00652218 for the exploration of the tachykinin NK1 receptor by spect. J Labelled Compd. Radiopharm 44:S280-S282 (2001).
Liu et al., Treatments for pulmonary arterial hypertension. Respiratory Medicine, Baillier Tindall, London, GB 100(5):765-774 (2006).
Lundblad et al., Increased cortical cell loss and prolonged hemodynamic depression after traumatic brain injury in mice lacking the IP receptor for prostacyclin. Journal of Cerebral Blood Flow & Metabolism 28:367-376 (2008).
Mardla et al., Potentiation of antiaggregating effect of prostaglandins by alpha-tocopherol and quercetin. Platelets 15:319-324 (2004).
McCormick et al., Prostacyclin analogues: the next drug-eluting stent? Biochem. Soc. Trans. 35:910-911 (2007).
McGeer et al., Inflammation and neurodegeneration in Parkinson's disease. Parkinsonism Relat Disord. 10 Suppl 1:S3-S7 (2004).
McGoon et al., Screening, early detection, and diagnosis of pulmonary arterial hypertension: ACCP evidence-based clinical practice guidelines. Chest 126:14S-34S (2004).
McLaughlin et al, Pulmonary arterial hypertension. Pulmonary arterial hypertension. Circulation 114(13):1417-1431 (2006).
Miwa et al., Combination therapy with oral sildenafil and beraprost for pulmonary arterial hypertension associated with CREST syndrome. Int. Heart J. 48:417-422 (2007).
Moncada et al., Human arterial and venous tissues generate prostacyclin (prostaglandin x), a potent inhibitor of platelet aggregation. Lancet 1:18-20 (1977).
Morecroft et al., Effect of tryptophan hydroxylase 1 deficiency on the development of hypoxia-induced pulmonary hypertension. Hypertension 49:232-236 (2007).
Moss. Basic terminology of stereochemistry (IUPAC Recommendations 1996). Pure & Appl. Chem. 68(12):2193-2222 (1996).
Muller et al, Iloprost has potent anti-inflammatory properties on human monocyte-derived dendritic cells. Clinical & Experimental Allergy, Department of Pneumology, University of Freiburg, Germany 40:1214-1221 (2010).
Murata et al., Altered pain perception and inflammatory response in mice lacking prostacyclin receptor. Nature 388:678-682 (1997).
Naeije et al., Expert opinion on available options treating pulmonary arterial hypertension. Expert Opin.Pharmacother. 8:2247-2265 (2007).
Nagao et al., Role of prostaglandin I2 in airway remodeling induced by repeated allergen challenge in mice. Am. J. Respir. Cell Mol. Biol. 29:314-320 (2003).
Okuda et al., Acute effect of beraprost sodium on lower limb circulation in patients with non- insulin-dependent diabetes mellitus-evaluation by color Doppler ultrasonography and laser cutaneous blood flowmetry. Prostaglandins 52:375-384 (1996).
Osol (Editor), Remington's Pharmaceutical Sciences, 1980, Philadelphia College of Pharmaceutical Science, Chapter 27: Structure-Activity Relationship and Drug Design, pp. 420-435.
Owada et al., Effect of long-term administration of prostaglandin I(2) in incipient diabetic nephropathy. Nephron 92:788-796 (2002).
Patel et al. Comparison of current therapies to inhibit endothelin-induced growth of pulmonary artery smooth muscle cells (PASMCs) derived from patients with pulmonary arterial hypertension. Poster 22nd Annual Congress, Munich, Germany Sep. 6-10, 2014.
PCT/US2018/020519 International Search Report and Written Opinion dated Jun. 4, 2018.
Potapov. Stereochemistry. 2nd Ed [Textbook for Chemistry Majors]. USSR. (1988), p. 202, Publisher (Khimiya, Moscow, USSR) (English translation).

(56) References Cited

OTHER PUBLICATIONS

Pugliese et al., Clinical use of extended-release oral treprostinil in the treatment of pulmonary arterial hypertension. Integrated Blood Pressure Control 9:1-7 (2016).
Rabinovitch. Pathobiology of pulmonary hypertension. Annu. Rev. Pathol. Mech. Dis. 2:369-399 (2007).
Raychaudhuri et al., The prostacyclin analogue treprostinil blocks NFkappaB nuclear translocation in human alveolar macrophages. J. Biol. Chem. 277:33344-33348 (2002).
Robbins et al, Epoprostenol for treatment of pulmonary hypertension in patients with systemic lupus erythematosus. Chest 117:14-18 (2000).
Rosenkranz. Pulmonary hypertension: Current diagnosis and treatment. Clin. Res. Cardiol. 96(8):527-541 (2007).
Rosenzweig. Emerging treatments for pulmonary arterial hypertension. Expert Opin. Emerging Drugs 11(4):609-619 (2006).
Rosenzweig et al., Long-term prostacyclin for pulmonary hypertension with associated congenital heart defects. Circulation 99:1858-1865 (1999).
Sato et al., Effect of OP-2507, a novel prostacyclin analogue on ischemia and reperfusion induced arrhythmias in isolated perfused rat heart. Journal of Molecular and Cellular Cardiology, Academic Press, GB, 22:S74 (1990).
Schermuly et al., Antiremodeling effects of iloprost and the dual-selective phosphodiesterase 3/4 inhibitor tolafentrine in chronic experimental pulmonary hypertension. Circ. Res. 94:1101-1108 (2004).
Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).
Semple. Discovery of APDS811: an orally available prostacylclin receptor agonist for the treatment of Pulmonary Arterial Hypertension (PAH). Presentation for 4th RSC/SCI GPCRS in Medicinal Chemistry, Sep. 17-19, 2012 Surrey UK (39 pgs).
Shen et al. Abstract 16601: APD811, a Novel and Highly Selective Non-prostanoid IP Receptor Agonist in Smooth Muscle Cells From Patients With Pulmonary Hypertension. Circulation 134:A16601 (2016).
Shen et al. APD811, a Novel and Highly Selective Non-prostanoid IP Receptor Agonist in Smooth Muscle Cells From Patients With Pulmonary Hypertension. AHA meeting of Nov. 12-16, 2016.
Shindo et al., Clinical efficacy of a stable prostacyclin analog, iloprost, in diabetic neuropathy. Prostaglandins 41:85-96 (1991).
Shinomiya et al., Regulation of TNFalpha and interleukin-10 production by prostaglandins I(2) and E(2): studies with prostaglandin receptor-deficient mice and prostaglandin E-receptor subtype-selective synthetic agonists. Biochem. Pharmacol. 61:1153-1160 (2001).
Simonneau et al., Clinical classification of pulmonary hypertension. J. Am. Coll. Cardiol. 43:5S-12S (2004).
Simonneau et al. Selexipag: an oral, selective prostacyclin receptor agonist for the treatment of pulmonary arterial hypertension. Eur Respir J 40(4):874-880 (2012).
Stitham et al., Human prostacyclin receptor structure and function from naturally-occurring and synthetic mutations. Prostaglandins Other Lipid Mediat. 82:95-108 (2007).
Strauss et al., Prostanoid therapy for pulmonary arterial hypertension. Clin. Chest. Med. 28:127-142 (2007).
Streiter et al., The role of chelating diamine ligands in the goldberg reaction: a kinetic study on the copper-catalyzed amidation of aryl iodides. JACS Communications, J. Am. Chem. Soc. 127:4120-4121 (2005).
Szekeres et al., Delayed antiischemic effect of PgI2 and of a new stable PgI2 analogue 7-oxo-prostacyclin-Na in experimental model angina in dogs. Journal of Molecular and Cellular Cardiology, Academic Press, GB 15:132 (1983).
Taichman et al., Epidemiology of pulmonary arterial hypertension. Clin. Chest. Med., 28:1-22 (2007).
Takahashi et al., Augmentation of allergic inflammation in prostanoid IP receptor deficient mice. Br. J. Pharmacol, 137:315-322 (2002).
Takamura et al. Metabolism investigation leading to novel drug design 2: orally active prostacyclin mimetics. Part 5. Bioorg Med Chem Lett 16:4475-4478 (2006).
Tawara et al., Effects of combined therapy with a Rho-kinase inhibitor and prostacyclin on monocrotaline-induced pulmonary hypertension in rats. Journal of Cardiovascular Pharmacology 50(2):195-200 (2007).
Tennis et al, The role of prostacyclin in lung cancer. Translation Research, Division of Pulmonary Sciences and Critical Care Medicine, Department of Medicine, University of Colorado Denver Health Sciences, Denver, Colorado 155(2):57-61 (2010).
Thoorens et al., Microcrystalline cellulose, a direct compression binder in a quality by design environment—a review. International Journal Pharm. 473(1-2):64-72 (2014).
Tran et al., Discovery of 2-(((1r,4r)-4-(((4-Chlorophenyl)(phenyl)c arbamoyl)oxy)methyl)cyclohexyl)methoxy)acetate (Ralinepag): an orally active prostacyclin receptor agonist for the treatment of pulmonary arterial hypertension. Journal of Medicinal Chemistry 60(3):913-927 (2017).
Tuder et al., Prostacyclin synthase expression is decreased in lungs from patients with severe pulmonary hypertension. Am. J. Respir. Crit. Care Med. 159:1925-1932 (1999).
Type 1 diabetes [online] retrieved from the internet on Jan. 29, 2021. URL: https://www.mayoclinic.org/diseases-conditions/type-1-diabetes/diagnosis-treatnnent/drc-2.
TYVASO® product information. Available at https://www.tyvaso.com (3 pgs.) (2018).
Ueno et al., Effects of beraprost sodium, a prostacyclin analogue, on diabetic neuropathy in streptozotocin-induced diabetic rats. Jpn. J. Pharmacol, 70:177-182 (1996).
Ueno et al., Effects of beraprost sodium, a prostacyclin analogue, on tail flick response in two models of diabetic-neuropathy in rats and its mechanism. Life Sci. 59:PL105-PL110 (1996).
United States Pharmacopeial Convention, Chapter 711; Dissolution (2011).
UPTRAVI® product information. Available at https://www.uptravi.com/ (3 pgs.) (2018).
Van Rijt et al., In vivo depletion of lung CD11c+ dendritic cells during allergen challenge abrogates the characteristic features of asthma. J. Exp. Med., 201:981-991 (2005).
Ventetuolo et al. WHO Group 1 pulmonary arterial hypertension: Current and investigative therapies. Prog Cardiovasc Dis 55(2):89-103 (2012).
Vippagunta et al., Crystalline solids. Advanced Drug Delivery Reviews 48:3-26 (2001).
Walther et al., Synthesis of serotonin by a second tryptophan hydroxylase isoform. Science 299:76 (2003).
Wang et al. Deletion of microsomal prostaglandin E synthase-1 augments prostacyclin and retards atherogenesis. Proc. Natl. Acad. Sci. USA 103:14507-14512 (2006).
Xiao et al., Roles of prostaglandin I(2) and thromboxane A(2) in cardiac ischemia-reperfusion injury: a study using mice lacking their respective receptors. Circulation 104:2210-2215 (2001).
Yamada et al., Hypotensive activity of novokinin, a potent analogue of ovokinin(2-7), is mediated by angiotensin AT(2) receptor and prostaglandin IP receptor. Peptides, 29:412-418 (2008).
Yamagishi et al., Beraprost sodium, a prostaglandin I2 analogue, protects against advanced gycation end products-induced injury in cultured retinal pericytes. Mol. Med. 8:546-550 (2002).
Yamashita et al., Beraprost sodium, prostacyclin analogue, attenuates glomerular hyperfiltration and glomerular macrophage infiltration by modulating ecNOS expression in diabetic rats. Diabetes Res. Clin. Pract. 57:149-161 (2002).
Zhou et al., Prostaglandin I2 analogs inhibit proinflammatory cytokine production and T cell stimulatory function of dendritic cells. J. Immunol. 178:702-710 (2007).
Zhu et al, Synthesis and mode of action of (125)I- and (3)H-labeled thieno[2,3-c]pyridine antagonists of cell adhesion molecule expression. J. Org. Chem. 67:943-948 (2002).
Berge et al.: Pharmaceutical salts. Journal of Pharmaceutical Sciences 66:1-19 (1977).

(56) References Cited

OTHER PUBLICATIONS

Meis et al. Riociguat for the treatment of pulmonary hypertension. Expert Opin Pharmacother 15(16):2419-2427 (2014).
Stasch et al. Soluble guanylate cyclase as an emerging therapeutic target in cardiopulmonary disease. Circulation 123(20):2263-2273 (2011).
Stasch et al. Soluble guanylate cyclase stimulators in pulmonary hypertension. Pharmacotherapy of Pulmonary Hypertension (Springer) pp. 279-313 (2013).

* cited by examiner

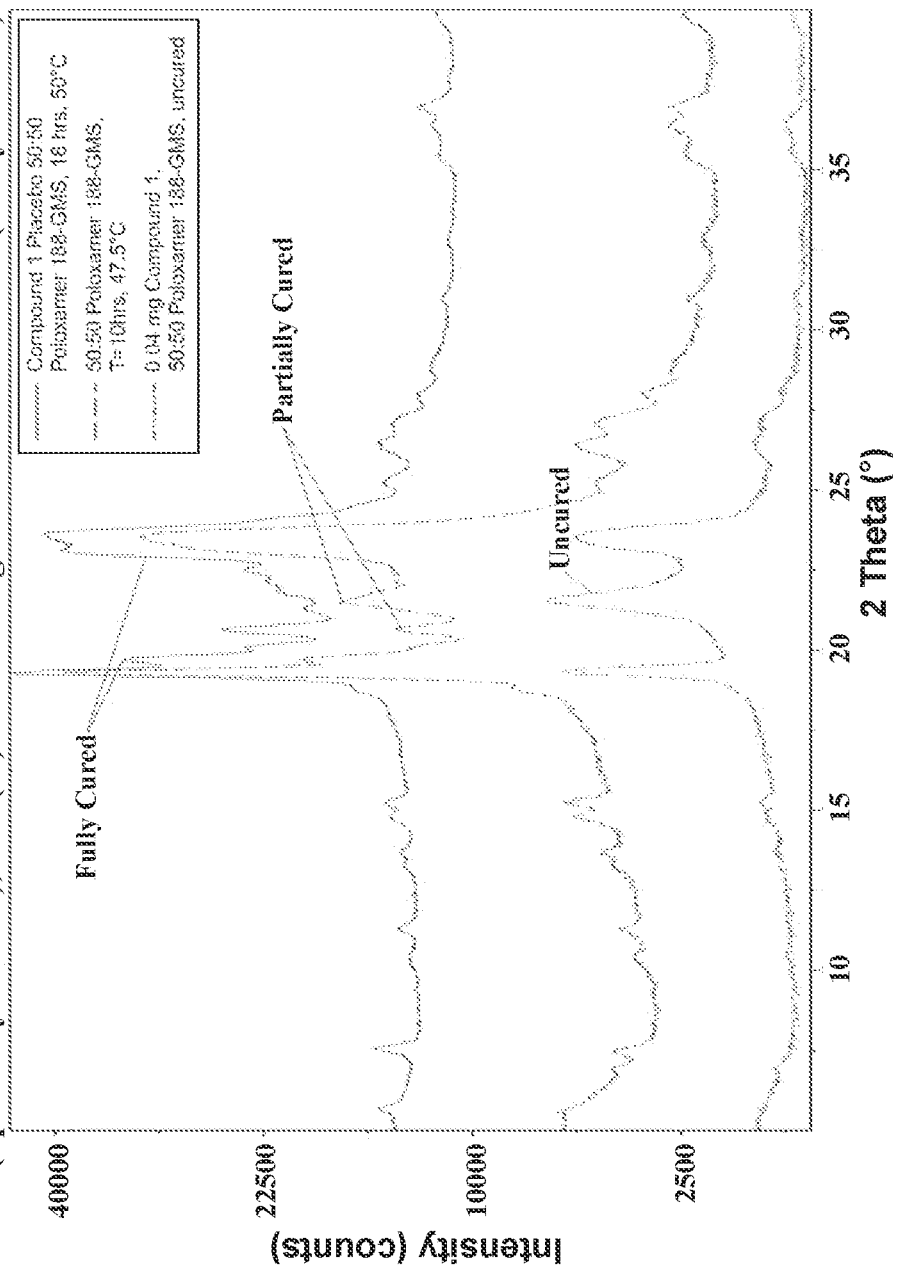

COMPOSITIONS COMPRISING PGI2-RECEPTOR AGONISTS AND PROCESSES FOR THE PREPARATION THEREOF

CROSS-REFERENCE TO RELATED APPLICATIONS

This application is a continuation of U.S. application Ser. No. 16/386,183 filed Apr. 16, 2019, which is a continuation of PCT International Application No. PCT/US2018/020519, filed Mar. 1, 2018, which claims the benefit of U.S. Provisional Application No. 62/465,675, filed Mar. 1, 2017; U.S. Provisional Application No. 62/468,832, filed Mar. 8, 2017; U.S. Provisional Application No. 62/526,039, filed. Jun. 28, 2017, and U.S. Provisional Application No. 62/530,515, filed Jul. 10, 2017, all of which are incorporated herein by reference in their entirety.

FIELD OF THE INVENTION

The present invention relates in some embodiments to methods of using, and compositions comprising a prostacyclin (PGI2) receptor agonist selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof. The compositions of the present invention are useful in the treatment of, for example: pulmonary arterial hypertension (PAH); idiopathic PAH; familial PAH, PAH associated with: a collagen vascular disease, a congenital heart disease, portal hypertension. HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure, hypertension; inflammation, psoriasis; psoriatic arthritis, rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

BACKGROUND OF THE INVENTION

PGI2 is a lipid molecule derived from arachidonic acid through the cyclooxygenase pathway. It is a potent vasodilator, antiproliferative, anti-thrombotic and antiplatelet agent that mediates its effects as an agonist of a G protein-coupled receptor (PGI2 receptor; e.g, human PGI2 receptor, GenBank® Accession No. NP_000951 and alleles thereof). It is known that the binding of PGI2 (or other such agonists) to the PGI2 receptor leads to coupling with the Gs protein and increased intracellular cAMP levels. (See, e.g, Zhang et al. Arch. Biochem. Biophys, 2006, 454:80-88).

PAH is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin (i.e., an agonist of the PGI2 receptor) has become an important strategy in the treatment of PAH. (See, e.g, Tuder et al. Am. J. Respir. Crit, Care. Med, 1999, 159:1925-1932; Humbert et al, Am. Coll. Cardiol, 2004, 43:13S-24S; Rosenzweig, Expert Opin. Emerging Drugs, 2006, 11:609.619; McLaughlin et al, Circulation, 2006, 114:1417-1431; Rosenkranz, Clin. Res. Cardiol, 2007, 96:527-541; Driscoll et al, Expert Opin. Pharmacother, 2008, 9:2 65-81).

Trepostinil and iloprost are FDA-approved analogs of prostacyclin which, like prostacyclin, are not orally-active. Beraprost is an orally-active analog of prostacyclin approved for the treatment of PAH in Japan, but it has failed registration for the treatment of PAH in Europe and in the US. Of the three FDA-approved drugs, prostacyclin is the best studied in PAH patients. The approximate annual cost of treating PAH with these drugs is $25,000 to $200,000 depending on the dose. At present, many experts consider intravenous prostacyclin to be the most reliable agent for managing the sickest PAH patients. Due to the short half-life of prostacyclin, intravenous treatment is complicated by the need for a continuous infusion. Patients are at risk for potentially fatal rebound pulmonary hypertension if the infusion is abruptly disrupted, as well as significant risk of catheter-related complications including sepsis. (See, e.g, Rosenzweig, Expert Opin. Emerging Drugs, 2006, 11:609-619; Naeije et al, Expert Opin. Pharmacother, 2007, 8:2247-2265; Strauss et al, Clin. Chest. Med, 2007, 28:127-142; Driscoll et al, Expert Opin. Pharmacother, 2008, 9:65-81).

Orally available, non-prostanoid PGI2-receptor agonists that provide clinical benefits similar to currently available PGI2-receptor agonists have the potential to improve the standard of care for PAH. The compositions of the present invention comprise the PGI2-receptor agonist, Compound 1, a novel, non-prostanoid, oral drug candidate discovered by Arena Pharmaceuticals, Inc, and intended for the treatment of PAH. Compound 1 was disclosed in PCT publication WO2009/117095, which is incorporated herein by reference in its entirety. Various synthetic routes to Compound 1, its related salts, prodrugs, crystalline forms, and intermediates, have been reported in PCT publication WO 2011/037613, which is incorporated herein by reference in its entirety. 2-(((1r,4r)-4-(((4-chlorophenyl)(phenyl)carbamoyloxy)methyl)cyclohexylimethoxy)acetic acid (Compound 1) is disclosed in WO 2009/117095 (incorporated by reference herein in its entirety).

Compound 1 has the potential to improve treatment for PAH by providing patients with an oral, once-daily option targeting the PGI2 receptor. In view of the potency of Compound 1, side effects that are associated with this class of compounds may be observed in patients. Examples of such side effects include nausea and headaches.

Compound 1 has a long plasma half-life (~24 hours). Unlike many active compounds, an extended-release formulation of Compound 1 is not necessary to achieve once daily dosing. However, side effects (such as nausea and headaches) are associated with the class of compounds that target the IP receptor, and Compound 1 is a particularly potent IP receptor agonist. Accordingly, it is desirable to develop new pharmaceutical compositions that modify the release of Compound 1 to balance once daily dosing with improved pharmacokinetics In order to optimize treatment for patients with life-threatening disorders.

SUMMARY

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

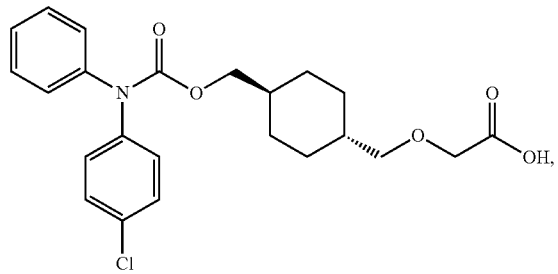

and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c), wherein:
  (a) about 15% to about 35% by weight of the compound is released over the first two hours in the aqueous medium,
  (b) about 24% to about 59% by weight of the compound is released over the first four hours in the aqueous medium; and/or
  (c) about 43% to about 96% by weight of the compound is released over the first eight hours in the aqueous medium.

In some embodiments, the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments, the release rate is measured with USP Apparatus 2 (paddle) at 40 to 60 rpm in 400 to 600 mL of an aqueous medium at a pH of 6.3 to 7.3 at a temperature of 37° C. 0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

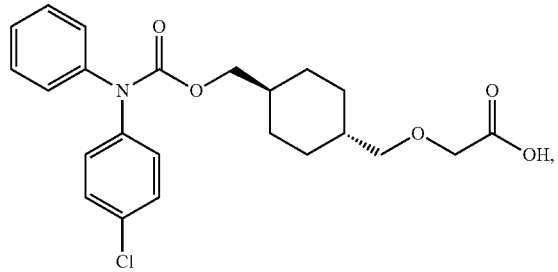

and pharmaceutically acceptable salts, solvates, and hydrates thereof, in an amount equivalent to a therapeutically effective amount of Compound 1, the composition having a release rate by weight of the compound in an aqueous medium that is release rate (a), wherein:
  (a) about 15% to about 35% by weight of the compound is released over the first two hours in the aqueous medium,
  wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

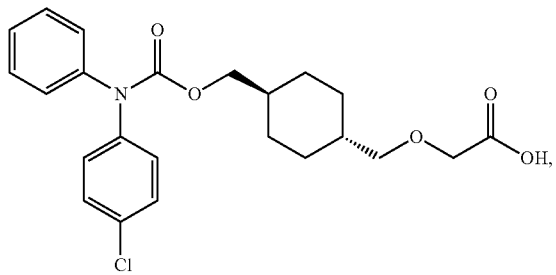

and pharmaceutically acceptable salts, solvates, and hydrates thereof, in an amount equivalent to a therapeutically effective amount of Compound 1, the composition having a release rate by weight of the compound in an aqueous medium that is release rate (b), wherein:
  (b) about 24% to about 59% by weight of the compound is released over the first four hours in the aqueous medium,
  wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

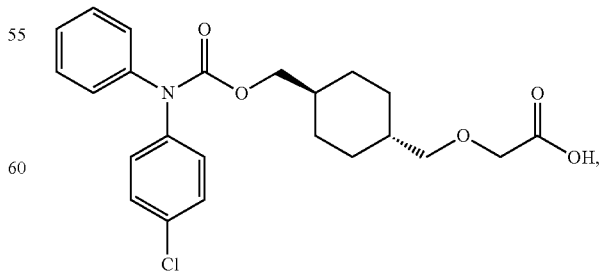

and pharmaceutically acceptable salts, solvates, and hydrates thereof, in an amount equivalent to a therapeutically effective amount of Compound 1, the composition having a release rate by weight of the compound in an aqueous medium that is release rate (c), wherein:
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

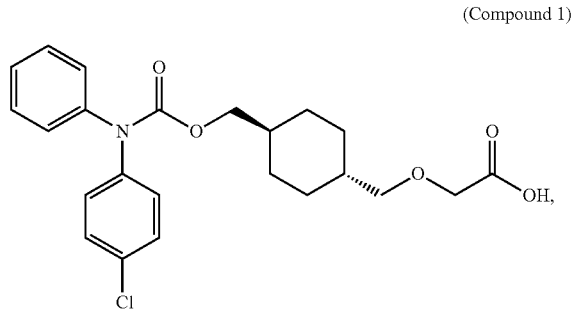 [SMILES: O=C(O)COC[C@H]1CC[C@H](COC(=O)N(c2ccccc2)c2ccc(Cl)cc2)CC1]

(Compound 1)

and pharmaceutically acceptable salts, solvates, and hydrates thereof, in an amount equivalent to a therapeutically effective amount of Compound 1, the composition having release rates by weight of the compound in an aqueous medium that are release rates (a) and (b), wherein:
  (a) about 15% to about 35% by weight of the compound is released over the first two hours in the aqueous medium, and
  (b) about 24% to about 59% by weight of the compound is released over the first four hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

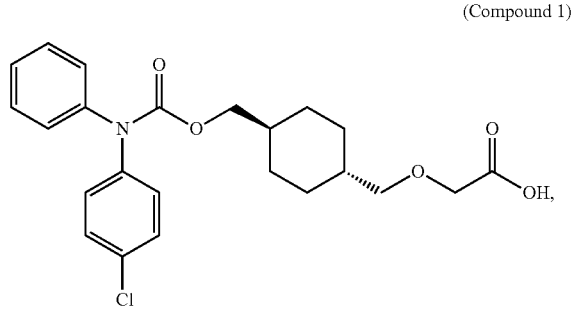 [SMILES: O=C(O)COC[C@H]1CC[C@H](COC(=O)N(c2ccccc2)c2ccc(Cl)cc2)CC1]

(Compound 1)

and pharmaceutically acceptable salts, solvates, and hydrates thereof, in an amount equivalent to a therapeutically effective amount of Compound 1, the composition having release rates by weight of the compound in an aqueous medium that are release rates (a) and (c).
  (a) about 15% to about 35% by weight of the compound is released aver the first two hours in the aqueous medium; and
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

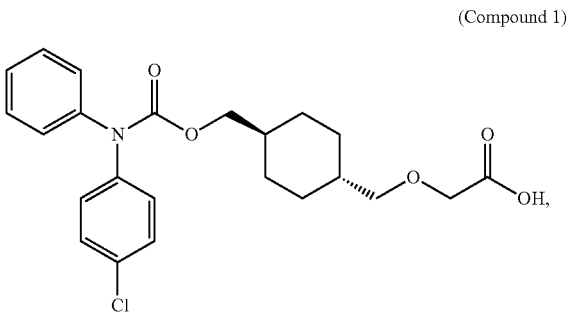 [SMILES: O=C(O)COC[C@H]1CC[C@H](COC(=O)N(c2ccccc2)c2ccc(Cl)cc2)CC1]

(Compound 1)

and pharmaceutically acceptable salts, solvates, and hydrates thereof, in an amount equivalent to a therapeutically effective amount of Compound 1, the composition having a release rate by weight of the compound in an aqueous medium that are release rates (b) and (c), wherein:
  (b) about 24% to about 59% by weight of the compound is released over the first four hours in the aqueous medium; and
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C. 0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

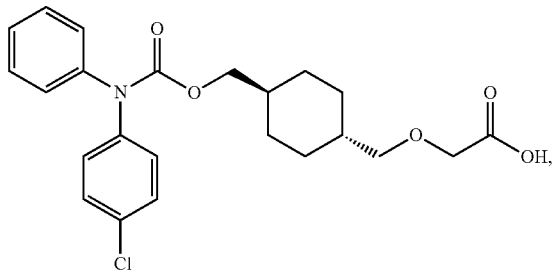

and pharmaceutically acceptable salts, solvates, and hydrates thereof, in an amount equivalent to a therapeutically effective amount of Compound 1 the composition having a release rate by weight of the compound in an aqueous medium that are release rates (a), (b) and (c), wherein:
(a) about 15% to about 35% by weight of the compound is released over the first two hours in the aqueous medium;
(b) about 24% to about 59% by weight of the compound is released over the first four hours in the aqueous medium; and
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a composition having, a release rate by weight of the compound as disclosed herein in an aqueous medium, wherein the release rate is the release rate measured with USP Apparatus 1 (baskets) at 100 rpm in 500 mL of an aqueous medium at a pH of 6.8 at a temperature of 37° C.±0.5° C., comprising sodium phosphate at a concentration of 0.05 M.

In some embodiments provided herein is a composition having a release rate by weight of the compound as disclosed herein in an aqueous medium, wherein the release rate is the release rate measured USP Apparatus 2 (paddle) at 50 rpm in 500 mL of an aqueous medium at a pH of 6.8 at a temperature of 37° C.±0.5° C., comprising sodium phosphate at a concentration of 0.05 M.

In some embodiments provided herein is a composition as disclosed herein, wherein the composition is a tablet. In some embodiments provided herein is a composition as disclosed herein, wherein the composition is in a tablet produced using wet granulation.

In some embodiments provided herein is a pharmaceutical composition comprising a compound selected from 2-(((1r,4r)-4-(((4-chlorophenyl)(phenyl)carbamoyloxy)methyl)cyclohexyl)methoxy acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 2300 mPA seconds to about 3800 mPA seconds when present in an amount of about 2% in water at 20° C., wherein the excipient is present in an amount equal to about 40% to about 60% by weight.

In some embodiments provided herein is a pharmaceutical composition comprising a compound selected from 2-(((1r, 4r)-4-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 75 mPA seconds to about 120 mPA seconds when present in an amount of about 2% in water at 20° C., wherein the excipient is present in an amount equal to about 40% to about 60% by weight.

In some embodiments provided herein is a pharmaceutical composition comprising a compound selected from 2-(((1r, 4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.

In some embodiments provided herein is a process for preparing a pharmaceutical composition comprising a compound selected from 2-(((1r,4r)-4-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, as disclosed herein, wherein the process comprises mixing the compound, ethanol, a first excipient comprising hydroxypropyl methylcellulose having a viscosity of about 2300 mPA seconds to about 3800 mPA seconds when present in an amount of about 2% in water at 20° C., and a second excipient comprising hydroxypropyl methylcellulose having a viscosity of about 75 mPA seconds to about 120 mPA seconds when present in an amount of about 2% in water at 20° C., to form the composition.

In some embodiments provided herein is a pharmaceutical composition comprising a compound selected from 2-(((1r, 4r)-4-(((4-chlorophenyl)(phenyl)carbamoyloxy)methyl)cyclohexyl)methoxy acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain; and the second excipient comprises an ester of a polyalcohol and a fatty acid.

In some embodiments provided herein is a pharmaceutical composition prepared by the process comprising:
curing a mixture comprising a compound selected from 2-(((1r,4r)-4-(((4-chlorophenyl)(phenyl)carbamoyloxy) methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain and the second excipient comprises an ester of a polyalcohol and a fatty acid, to form the composition.

In some embodiments provided herein is a process for preparing a pharmaceutical composition, the process comprising:

curing a mixture comprising a compound selected from 2-(((1r,4r)-4-(((4-chlorophenyl)(phenyl)carbamoyloxy) methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain, and the second excipient comprises an ester of a polyalcohol and a fatty acid, to form the composition.

BRIEF DESCRIPTION OF THE DRAWINGS

FIG. 7C shows three Powder X-Ray Diffraction spectra of capsules comprising Poloxamer 188 and research grade GMS in a 50:50 ratio by weight (i) before curing ("uncured"), (ii) after partial curing at 47.5° C. for 10 hours ("partially cured"), and (iii) after curing at 50° C. for 18 hours ("fully cured").

DETAILED DESCRIPTION OF THE INVENTION

Figure 1:
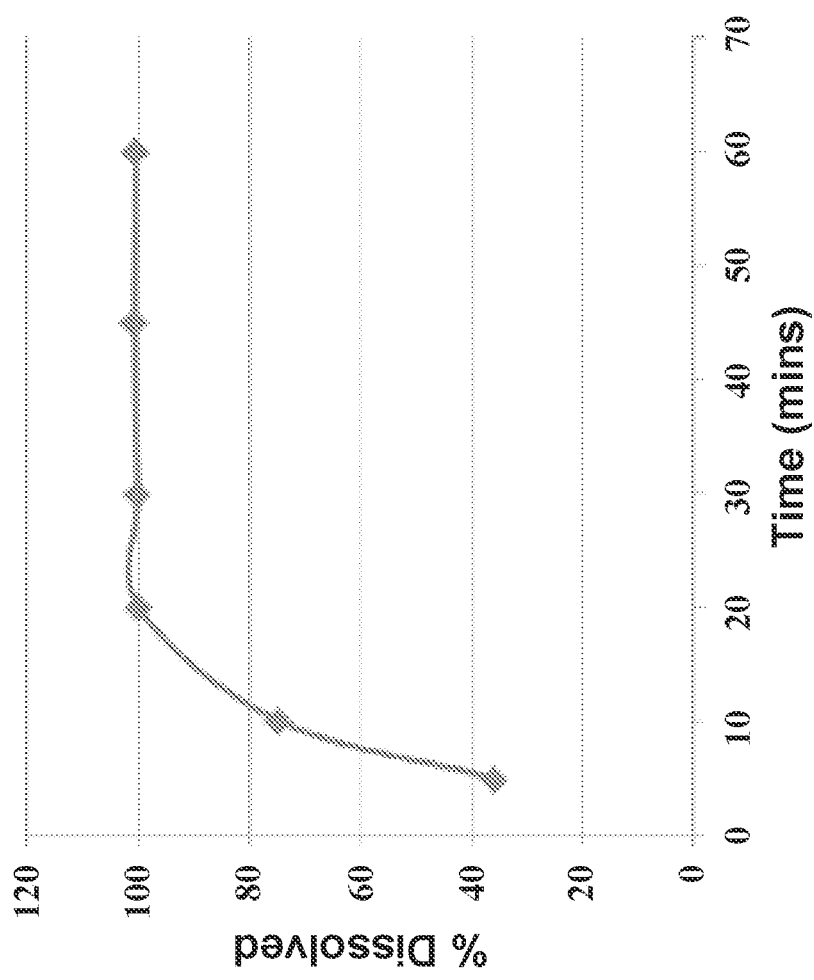
FIG. 1 shows the release profile of Compound 1 with an immediate-release formulation.

Compound 1 is a potent IP receptor agonist. Due to the low doses of Compound 1 needed for therapeutic purposes, a solid oral dosage form (such as a tablet) would require extensive formulation development to achieve content uniformity. A liquid-in-hard gelatin capsule was therefore developed with an immediate-release formulation for initial clinical studies with Compound 1. However, the immediate-release capsule formulation had a high $C_{max}$, and peak-trough fluctuation, which can affect tolerability and patient compliance. To mitigate these concerns, the dosage amount for the immediate-release capsule formulation was reduced and administered twice daily.

Modified-release capsule formulations were developed for subsequent clinical studies to achieve once daily dosing while addressing shortcomings of the immediate-release formulation. These modified-release capsule formulations demonstrated a desirable combination of properties—balancing once daily dosing with a stable release profile and improved pharmacokinetics. Modified-release tablet formulations were also developed to achieve content uniformity and further improve stability and manufacturing processes. Described herein are such modified-release formulations of Compound 1.

Definitions

For clarity and consistency, the following definitions will be used throughout this patent document.

The term "agonist" as used herein refers to a moiety that interacts with and activates a G-protein-coupled receptor, for instance PGI2, and can thereby initiate a physiological or pharmacological response characteristic of that receptor. For example, an agonist may activate an intracellular response upon binding to a receptor, or enhance GTP binding to a membrane.

The term "in need of treatment" and the term "in need thereof" when referring to treatment are used interchangeably and refer to a judgment made by a caregiver (e. g. physician, nurse, nurse practitioner, etc. in the ease of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, eats, swine, cattle, sheep, horses, or primates, and most preferably humans.

The term "modulate or modulating" refers to an increase or decrease in the amount, quality, response or effect of a particular activity, function or molecule.

The term "composition" refers to a compound, including but not limited to, salts, solvates, and hydrates of a compound of the present invention, in combination with at least one additional component.

The term "pharmaceutical composition" refers to a composition comprising at least one active ingredient, such as a compound as described herein; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "hydroxypropyl methylcellulose", which may be also referred to as "hypromellose", refers to a propylene glycol ether of methylcellulose. The hydroxypropyl methylcellulose is available in varying degrees of viscosity. As an example, the hydroxypropyl methylcellulose may be a hydroxypropyl methylcellulose having a viscosity of about 2300 mPA seconds to about 3800 mPA seconds when present in an amount of about 2% in water at 20° C. As an example, the hydroxypropyl methylcellulose may be Methocel K4M Premium CR. As an example, the hydroxypropyl methylcellulose may be a hydroxypropyl methylcellulose having a viscosity of about 75 mPA seconds to about 120 mPA seconds when present in an amount of about 2% in water at 20° C. As an example, the hydroxypropyl methylcellulose may be Methocel K100 Premium INCR.

The term "copolymer comprising (a) a first polyoxyethylene chain; (b) a poly(propylene oxide) chain bonded to the first polyoxyethylene chain; and (c) a second polyoxyethylene chain bonded to the poly(propylene oxide) chain" refers to a polyethylene oxide)-block-poly(propylene oxide)-block-polyethylene oxide) block copolymer.

The term "polyoxyethylene oil" as used herein refers to a class of excipients comprising or consisting essentially of either a single compound or a mixture of compounds obtained from the reaction of varying amounts of ethylene oxide with one or more glycerides derived from one or more hydroxyl substituted fatty acids. Examples of hydroxyl substituted fatty acids include ricinoleic acid. Examples of glycerides derived from one or more hydroxyl substituted fatty acids include castor oil. Examples of polyoxyethylene oils include Kolliphor® RH40 (previously known as Cremophor® RH140) (BASF, Mount Olive, NJ).

The term "stearoyl polyoxylglyeerides" means a mixture of monoesters, diesters, and triesters of glycerol, and monoesters and diesters of polyethylene glycols with a nominal mean relative molecular weight between 300 and 4000. Examples of stearoyl polyoxylglycerides include stearoyl polyoxyl-32 glycerides such as Gelucire® 50/13 (Gattefosse, France) and Acconon® C-50 (ABITEC, USA).

The term "Poloxamer" as used herein refers to an excipient comprising a copolymer comprising (a) a first polyoxyethylene chain; (b) a polypropylene oxide) chain bonded to the first polyoxyethylene chain; and (e) a second polyoxyethylene chain bonded to the poly(propylene oxide) chain. In some embodiments, the copolymer has an average molecular weight of about 17500 or less, such as between about 7680 and about 9510. In some embodiments, the excipient consists essentially of the copolymer. In some embodiments, the excipient is the copolymer.

In some embodiments, the copolymer is represented by the chemical structure below:

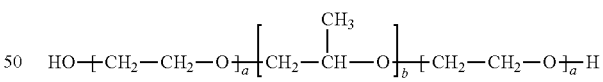

wherein the values in the copolymer for variable a at each occurrence are independently from 1 to about 141, such as from about 64 to about 141, such as from about 80 to about 101, or such as from 1 to about 101: and wherein the values in the copolymer for variable h are from 1 to about 56, such as from about 27 to about 56, such as from about 37 to about 44. Poloxamers are known or can be prepared by methods in the art. A number of poloxamers are commercially available. Representative examples of a Poloxamer include, but are not limited to, Poloxamer 124 (Pluronic® L44NF), Poloxamer 188 (Pluronic® F68NF), Poloxamer 237 (Pluronic® F87NF), Poloxamer 338 (Pluronic® F108NF), Poloxamer 407 (Pluronic® F127NF) and the like.

In some embodiments, the values in the copolymer for variable a and for variable b are as follows:

|   | a | b |
|---|---|---|
| In Poloxamer 188 | about 80 | about 27 |
| In Poloxamer 237 | about 64 | about 37 |
| In Poloxamer 338 | about 141 | about 44 |
| In Poloxamer 407 | about 101 | about 56 |

The term "glycerol monostearate"—also referred to as "glyceryl monostearate" or "GMS"—as used herein refers to an excipient comprising the monoester of glycerol and stearic acid.

The term "monoester content", also referred to as the "monoglyceride content", is the amount, as a mole percentage, of the monoester of glycerol and stearic acid in the excipient relative to the sum of the amounts of the monoester, the diester of glycerol and stearic acid, the triester of glycerol and stearic acid, and glycerol, in the excipient. Various forms of glycerol monostearate (GMS) are commercially available. "Research grade" GMS has a monoester content that is lower than "NF" grade GMS. NF grade GMS has a monoester content that is lower than that of "food grade" GMS. In some embodiments, the compositions of the invention comprise food grade GMS. As used herein, "food grade" GMS has a monoester content of at least about 95%. Representative examples of commercially available GMS include, but are not limited to, Myverol™ 1.8-04 K, Myverol™ 18-06 K, Myverol™ 18-06 PK, Myverol™ 18-04 K, and the like.

The term "cured composition" as used herein refers to a pharmaceutical composition comprising a compound selected from 2-(((1r,4r)-4-(((4-chlorophenyl)(phenyl)carbamoyloxy)methyl)cyclohexyl)methoxy)acetic acid (Compound 1) and pharmaceutically acceptable salts, solvates, and hydrates thereof, the first excipient, and the second excipient that are cured together.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:
 (1) preventing the disease, for example, preventing a disease, condition or disorder in an individual that may be predisposed to the disease, condition or disorder but does not yet experience or display the pathology or symptomatology of the disease;
 (2) inhibiting the disease, for example, inhibiting a disease, condition or disorder in an individual that is experiencing or displaying the pathology or symptomatology of the disease, condition or disorder (i.e., arresting further development of the pathology and/or symptomatology); and
 (3) ameliorating the disease, for example, ameliorating a disease, condition or disorder in an individual that is experiencing or displaying the pathology or symptomatology of the disease, condition or disorder (Le, reversing the pathology and/or symptomatology).

The term "an amount equivalent to", followed by the recitation of an amount of Compound 1 (such as, for example 0.01 mg of Compound 1) refers to the amount of a compound selected from 2-(((1(1r,4r)-4-(((4-chlorophenyl)(phenyl)carbamoyloxy)methyl)cyclohexyl)methoxy)acetic acid (Compound 1) and pharmaceutically acceptable salts, solvates, and hydrates thereof that is equivalent to the recited amount of Compound 1.

The term "% by weight" when referring to an amount of a component that is present in a composition—such as Compound 1, or such as an excipient—refers to the amount of that component as a % by weight of the composition.

The term "release rate", also referred to as a "dissolution rate" herein, with reference to a compound, refers to the percentage amount of that compound that is released in an aqueous medium over a specified time period. As an example, the recitation "a release rate by weight of the compound in an aqueous medium that is release rate (a), wherein (a) about 15% to about 35% by weight of the compound is released over the first two hours" means that the percentage by weight of the compound that is released over the first two hours is about 15% to about 35% by weight of the initial amount of the compound. The term "release profile", also referred to as a "dissolution profile" herein, with reference to a compound, refers to a plot showing the percentage amount of that compound that is released in an aqueous medium over time. The aqueous medium may be an aqueous medium as described herein.

Compositions and Processes of Manufacture

In some embodiments provided herein is a pharmaceutical composition comprising a compound selected from 2-(((1 r,4r)-1-(((4-chlorophenyl)(phenyl)carbamoyloxy)methyl)cyclohexyl)acetic acid, having the structure:

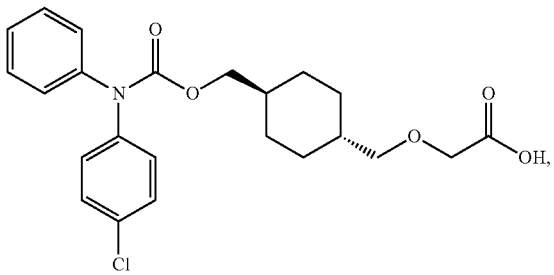

(Compound 1)

and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c), wherein:
 (a) about 15% to about 35% by weight of the compound is released over the first two hours in the aqueous medium;
 (b) about 24% to about 59% by weight of the compound is released over the first four hours in the aqueous medium; and/or
 (c) about 43% to about 96% by weight of the compound is released over the first eight hours in the aqueous medium.

In some embodiments, the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments, the release rate is measured with USP Apparatus 2 (paddle) at 40 to 60 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

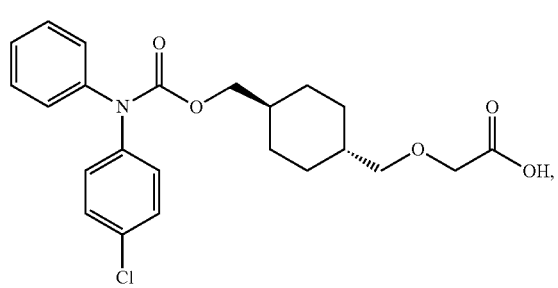

and pharmaceutically acceptable salts, solvates, and hydrates thereof, in an amount equivalent to a therapeutically effective amount of Compound 1, the composition having a release rate by weight of the compound in an aqueous medium that is release rate (a), wherein:
(a) about 15% to about 35% by weight of the compound is released over the first two hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

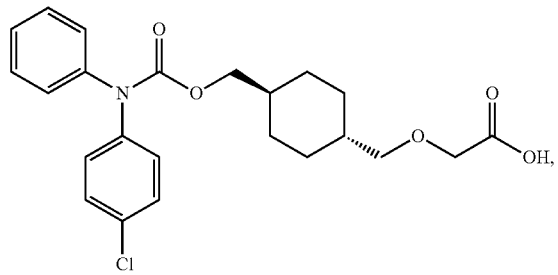

and pharmaceutically acceptable salts, solvates, and hydrates thereof, in an amount equivalent to a therapeutically effective amount of Compound 1, the composition having a release rate by weight of the compound in an aqueous medium that is release rate (b), wherein:
(b) about 24% to about 59% by weight of the compound is released over the first four hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

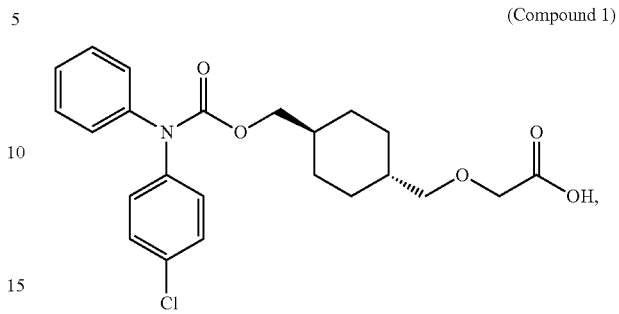

and pharmaceutically acceptable salts, solvates, and hydrates thereof, in an amount equivalent to a therapeutically effective amount of Compound 1, the composition having a release rate by weight of the compound in an aqueous medium that is release rate (c), wherein:
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH 46.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

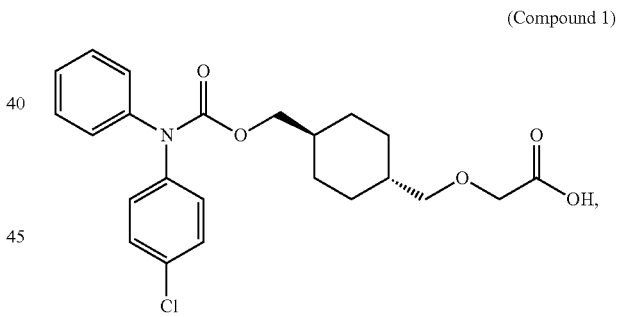

and pharmaceutically acceptable salts, solvates, and hydrates thereof, in an amount equivalent to a therapeutically effective amount of Compound 1, the composition having release rates by weight of the compound in an aqueous medium that are release rates (a) and (b), wherein:
(a) about 15% to about 35% by weight of the compound is released over the first two hours in the aqueous medium; and
(b) about 24% to about 59% by weight of the compound is released over the first four hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r, 4r)-4-(((4-chlorophenyl)(phenyl)carbamoyloxy)methyl)cyclohexyl)methoxy)acetic acid, having the structure:

(Compound 1)

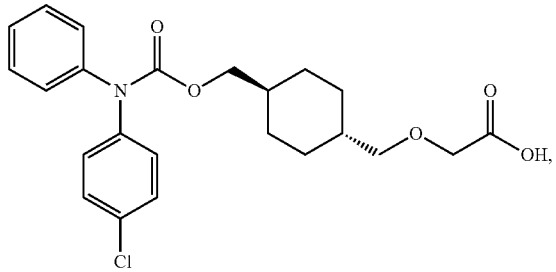

and pharmaceutically acceptable salts, solvates, and hydrates thereof, in an amount equivalent to a therapeutically effective amount of Compound 1, the composition having release rates by weight of the compound in an aqueous medium that are release rates (a) and (c), wherein:
(a) about 15% to about 35% by weight of the compound is released over the first two hours in the aqueous medium; and
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

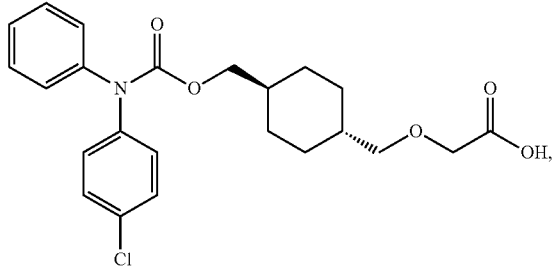

and pharmaceutically acceptable salts, solvates, and hydrates thereof, in an amount equivalent to a therapeutically effective amount of Compound 1, the composition having a release rate by weight of the compound in an aqueous medium that are release rates (b) and (c), wherein:
(b) about 24% to about 59% by weight of the compound is released over the first four hours in the aqueous medium; and
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-4-(((4-chlorophenyl)(phenyl)carbamoyloxy)methyl)cyclohexyl)methoxy)acetic acid, having the structure:

(Compound 1)

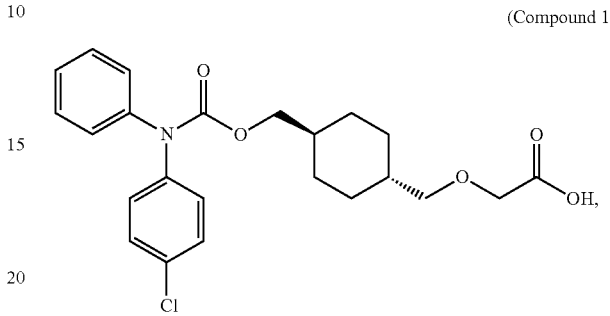

and pharmaceutically acceptable salts, solvates, and hydrates thereof, in an amount equivalent to a therapeutically effective amount of Compound 1, the composition having a release rate by weight of the compound in an aqueous medium that are release rates (a), (b) and (c), wherein:
(a) about 15% to about 35% by weight of the compound is released over the first two hours in the aqueous medium;
(b) about 24% to about 59% by weight of the compound is released over the first four hours in the aqueous medium; and
(c) about 43% to about 6% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a composition having a release rate by weight of the compound as disclosed herein in an aqueous medium, wherein the release rate is the release rate measured with USP Apparatus 1 (baskets) at 100 rpm in 500 mL of an aqueous medium at a pH of 6.8 at a temperature of 37° C.±0.5° C., comprising sodium phosphate at a concentration of 0.05 M.

In some embodiments provided herein is a composition having a release rate by weight of the compound as disclosed herein in an aqueous medium, wherein the release rate is the release rate measured USP Apparatus 2 (paddle) at 50 rpm in 500 mL of an aqueous medium at a pH of 6.8 at a temperature of 37° C.±0.5° C., comprising sodium phosphate at a concentration of 0.05 M.

In some embodiments provided herein is a composition as disclosed herein, wherein the composition is a tablet.

In some embodiments provided herein is a composition as disclosed herein, whereon the composition 3S a capsule.

In some embodiments provided herein is a composition having one or more of release rates (a), (b) and (c) as disclosed herein, wherein the composition comprises one or more excipients selected from the group consisting of (1) ethers of cellulose, such as hydroxypropyl methylcellulose, (2) esters of cellulose, (3) cellulose acetate, (4) ethyl cellulose, (5) polyvinyl acetate, (6) neutral copolymers based on ethylacrylate and methylmethacrylate, (7) copolymers of acrylic and methacrylic acid esters with quaternary ammonium groups, (8) pH-insensitive ammonio methacrylic acid copolymers, (9) polyethylene oxides, (10) polyvinylpyrrolidone, (11) polysaccharides of natural origin such as xanthan gum and locust bean gum, (12) polyethylene glycol, (13) polypropylene glycol, (14) castor oil, (15) triacetin, (16) tributyl citrate, (17) tri-ethyl citrate, (18) acetyl tri-n-butyl citrate, (19) diethyl phthalate, (20) dibutyl sebacate, (21) acetylated mono- and di-glycerides, and mixtures thereof. In some embodiments, the excipients are selected from the group consisting of (1) and mixtures thereof. In some embodiments, the excipients are selected from the group consisting of (2) and mixtures thereof. In some embodiments, the excipients are selected from the group consisting of (3) and mixtures thereof. In some embodiments, the excipients are selected from the group consisting of (4) and mixtures thereof. In some embodiments, the excipients are selected from the group consisting of (5) and mixtures thereof. In some embodiments, the excipients are selected from the group consisting of (6) and mixtures thereof. In some embodiments, the excipients are selected from the group consisting of (7) and mixtures thereof. In some embodiments, the excipients are selected from the group consisting of (8) and mixtures thereof. In some embodiments, the excipients are selected from the group consisting of (9) and mixtures thereof. In some embodiments, the excipients are selected from the group consisting of (10) and mixtures thereof. In some embodiments, the excipients are selected from the group consisting of (11) and mixtures thereof. In some embodiments, the excipients are selected from the group consisting of (12) and mixtures thereof. In some embodiments, the excipients are selected from the group consisting of (13) and mixtures thereof. In some embodiments, the excipients are selected from the group consisting of (14) and mixtures thereof. In some embodiments, the excipients sine selected from the group consisting of (1), (2), and mixtures thereof. In some embodiments, the excipients are selected from the group consisting of (1), (3), and mixtures thereof. In some embodiments, the excipients are selected from the group consisting of (1), (4), and mixtures thereof. In some embodiments, the excipients are selected from the group consisting of (1), (5), and mixtures thereof. In some embodiments, the excipients are selected from the group consisting of (1), (6), and mixtures thereof. In some embodiments, the excipients are selected from the group consisting of (1), (7), and mixtures thereof. In some embodiments, the excipients are selected from the group consisting of (1), (8), and mixtures thereof. In some embodiments, the excipients are selected from the group consisting of (1), (9), and mixtures thereof. In some embodiments, the excipients are selected from the group consisting of (1), (10), and mixtures thereof. In some embodiments, the excipients are selected from the group consisting of (1), (11), and mixtures thereof. In some embodiments, the excipients are selected from the group consisting of (1), (12), and mixtures thereof. In some embodiments, the excipients are selected from the group consisting of (1), (13), and mixtures thereof. In some embodiments, the excipients are selected from the group consisting of (1), (14), and mixtures thereof. In some embodiments, the excipients are selected from the group consisting of (2), (3), and mixtures thereof. In some embodiments, the excipients are selected from the group consisting of (2), (4), and mixtures thereof. In some embodiments, the excipients are selected from the group consisting of (2), (5), and mixtures thereof. In some embodiments, the excipients are selected from the group consisting of (2), (6), and mixtures thereof. In some embodiments, the excipients are selected from the group consisting of (2), (7), and mixtures thereof. In some embodiments, the excipients are selected from the group consisting of (2), (8), and mixtures thereof. In some embodiments, the excipients are selected from the group consisting of (2), (9), and mixtures thereof. In some embodiments, the excipients are selected from the group consisting of (2), (10), and mixtures thereof. In some embodiments, the excipients are selected from the group consisting of (2), (11), and mixtures thereof. In some embodiments, the excipients are selected from the group consisting of (2), (12), and mixtures thereof. In some embodiments, the excipients are selected from the group consisting of (2), (13), and mixtures thereof. In some embodiments, the excipients are selected from the group consisting of (2), (14), and mixtures thereof. In some embodiments, the excipients are selected from the group consisting of (3), (4), and mixtures thereof. In some embodiments, the excipients are selected from the group consisting of (3), (5), and mixtures thereof. In some embodiments, the excipients are selected from the group consisting of (3), (6), and mixtures thereof. In some embodiments, the excipients are selected from the group consisting of (3), (7), and mixtures thereof. In some embodiments, the excipients are selected from the group consisting of (3), (8), and m mixtures thereof. In some embodiments, the excipients are selected from the group consisting of (3), (9), and mixtures thereof. In some embodiments, the excipients are selected from the group consisting of (3), (10), and mixtures thereof. In some embodiments, the excipients are selected from the group consisting of (3), (11), and mixtures thereof. In some embodiments, the excipients are selected from the group consisting of (3), (12), and mixtures thereof. In some embodiments, the excipients are selected from the group consisting of (3), (13), and mixtures thereof. In some embodiments, the excipients are selected from the group consisting of (3), (14), and mixtures thereof. In some embodiments, the excipients are selected from the group consisting of (4), (5), and mixtures thereof. In some embodiments, the excipients are selected from the group consisting of (4), (6), and mixtures thereof. In some embodiments, the excipients are selected from the group consisting of (4), (7), and mixtures thereof. In some embodiments, the excipients are selected from the group consisting of (4), (8), and mixtures thereof. In some embodiments, the excipients are selected from the group consisting of (4), (9), and mixtures thereof. In some embodiments, the excipients are selected from the group consisting of (4), (10), and mixtures thereof. In some embodiments, the excipients are selected from the group consisting of (4), (11), and mixtures thereof. In some embodiments, the excipients are selected from the group consisting of (4), (12), and mixtures thereof. In some embodiments, the excipients are selected from the group consisting of (4), (13), and mixtures thereof. In some embodiments, the excipients are selected from the group consisting of (4), (14), and mixtures thereof. In some embodiments, the excipients are selected from the group consisting of (5), (6), and mixtures thereof. In some embodiments, the excipients are selected from the group consisting of (5), (7), and mixtures thereof. In some embodiments, the excipients are selected from the group consisting of (5), (8), and mixtures thereof. In some embodiments, the excipients are selected from the group consisting of (5), (9), and mixtures thereof. In some embodiments, the excipients are selected from the group consisting of (5), (10), and mixtures thereof. In some embodiments, the excipients are selected from the group consisting of (5), (11), and mixtures thereof. In some embodiments, the excipients are selected from the group consisting of (5), (12), and mixtures thereof. In some embodiments, the excipients are selected from the group consisting of (5), (13), and mixtures thereof. In some embodiments, the excipients are selected from the group consisting of (5), (14), and mixtures thereof. In some embodiments, the excipients are selected from the group consisting of (6), (7), and mixtures thereof. In some embodiments, the excipients are selected from the group consisting of (6), (8), and mixtures thereof. In some embodiments, the excipients are selected from the group consisting of (6), (9), and mixtures thereof. In some embodiments, the excipients are selected from the group consisting of (6), (10), and mixtures thereof. In some embodiments, the excipients are selected from the group consisting of (6), (11), and mixtures thereof. In some embodiments, the excipients are selected from the group consisting of (6), (12), and mixtures thereof. In some embodiments, the excipients are selected from the group consisting of (6), (13), and mixtures thereof. In some embodiments, the excipients are selected from the group consisting of (6), (14), and mixtures thereof. In some embodiments, the excipients are selected from the group consisting of (7), (8), and mixtures thereof. In some embodiments, the excipients are selected from the group consisting of (7), (9), and mixtures thereof. In some embodiments, the excipients are selected from the group consisting of (7), (10), and mixtures thereof. In some embodiments, the excipients are selected from the group consisting of (7), (11), and mixtures thereof. In some embodiments, the excipients are selected from the group consisting of (7), (12), and mixtures thereof. In some embodiments, the excipients are selected from the group consisting of (7), (13), and mixtures thereof. In some embodiments, the excipients are selected from the group consisting of (7), (14), and mixtures thereof. In some embodiments, the excipients are selected from the group consisting of (8), (9), and mixtures thereof. In some embodiments, the excipients are selected from the group consisting of (8), (10), and mixtures thereof. In some embodiments, the excipients are selected from the group consisting of (8), (11), and mixtures thereof. In some embodiments, the excipients are selected from the group consisting of (8), (12), and mixtures thereof. In some embodiments, the excipients are selected from the group consisting of (8), (13), and mixtures thereof. In some embodiments, the excipients are selected from the group consisting of (8), (14), and mixtures thereof. In some embodiments, the excipients are selected from the group consisting of (9), (10), and mixtures thereof. In some embodiments, the excipients are selected from the group consisting of (9), (1 1), and mixtures thereof. In some embodiments, the excipients are selected from the group consisting of (9), (12), and mixtures thereof. In some embodiments, the excipients are selected from the group consisting of (9), (13), and mixtures thereof. In some embodiments, the excipients are selected from the group consisting of (9), (14), and mixtures thereof. In some embodiments, the excipients are selected from the group consisting of (10), (11), and mixtures thereof. In some embodiments, the excipients are selected from the group consisting of (10), (12), and mixtures thereof. In some embodiments, the excipients are selected from the group consisting 4(10), (13), and mixtures thereof. In some embodiments, the excipients are selected from the group consisting of (10), (14), and mixtures thereof. In some embodiments, the excipients are selected from the group consisting of (11), (12), and mixtures thereof. In some embodiments, the excipients are selected from the group consisting of (11), (13), and mixtures thereof. In some embodiments, the excipients are selected from the group consisting of (11), (14), and mixtures thereof. In some embodiments, the excipients are selected from the group consisting of (12), (13), and mixtures thereof. In some embodiments, the excipients are selected from the group consisting of (12), (14), and mixtures thereof. In some embodiments, the excipients are selected from the group consisting of (13), (14), and mixtures thereof.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 2300 mPA seconds to about 3800 mPA seconds when present in an amount of about 2% in water at 20° C.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 2300 m PA seconds to about 3800 mPA seconds when present in an amount of about 2% in water at 20° C., wherein the excipient is present in an amount equal to about 40% to about 60% by weight. In some embodiments, the composition comprises an excipient comprising hydroxypropyl methylcellulose having a viscosity of about 2300 mPA seconds to about 3800 mPA seconds when present in an amount of about 2% in water at 20° C., wherein the excipient is present in an amount equal to about 45% to about 55% by weight. In some embodiments, the composition comprises an excipient comprising hydroxypropyl methylcellulose having a viscosity of about 2300 mPA seconds to about 3800 mPA seconds when present in an amount of about 2% in water at 20° C., wherein the excipient is present in an amount equal to about 50% by weight.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 75 mPA seconds to about 120 mPA seconds when present in an amount of about 2% in water at 20° C.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises an excipient comprising hydroxypropyl methylcellulose having a viscosity of about 75 mPA seconds to about 120 mPA seconds when present in an amount of about 2% in water at 20° C., wherein the excipient is present in an amount equal to about 40% to about 60% by weight. In some embodiments, the composition comprises an excipient comprising hydroxypropyl methylcellulose having a viscosity of about 75 mPA seconds to about 120 mPA seconds when present in an amount of about 2% in water at 200° C., wherein the excipient is present in an amount equal to about 45% to about 55% by weight. In some embodiments, the composition comprises an excipient comprising hydroxypropyl methylcellulose having a viscosity of about 75 mPA seconds to about 120 mPA seconds when present in an amount of about 2% in water at 20° C., wherein the excipient is present in an amount equal to about 50% by weight.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.

In some embodiments provided herein is a process for preparing a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, as disclosed herein, wherein the process comprises mixing the compound, ethanol, a first excipient comprising hydroxypropyl methylcellulose having a viscosity of about 2300 mPA seconds to about 3800 mPA seconds when present in an amount of about 2% in water at 20° C., and a second excipient comprising hydroxypropyl methylcellulose having a viscosity of about 75 mPA seconds to about 120 mPA seconds when present in an amount of about 2% in water at 20° C.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the composition has a release rate by weight of the compound in an aqueous medium that is release rate (a), wherein:
  (a) about 15% to about 35% by weight of the compound is released over the first two hours in the aqueous medium,
  wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
  wherein the composition has a release rate by weight of the compound in an aqueous medium that is release rate (b), wherein:
  (b) about 24% to about 59% by weight of the compound is released over the first four hours in the aqueous medium,
  wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
  wherein the composition has a release rate by weight of the compound in an aqueous medium that is release rate (c), wherein:
  (c) about 43% to about 96% by weight of the compound is released over the first eight hours in the aqueous medium,
  wherein the release rate is measured with USP Apparatus 1 (baskets) at 80 to 120 rpm in 400 to 600 ml of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the composition has release rates by weight of the compound in an aqueous medium that are release rates (a) and (b), wherein:
  (a) about 15% to about 35% by weight of the compound is released over the first two hours in the aqueous medium; and
  (b) about 24% to about 59% by weight of the compound is released over the first four hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
wherein the composition has release rates by weight of the compound in an aqueous medium that are release rates (a) and (c), wherein:
  (a) about 15% to about 35% by weight of the compound is released over the first two hours in the aqueous medium; and
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
wherein the composition has release rates by weight of the compound in an aqueous medium that are release rates (b) and (c), wherein:
  (b) about 24% to about 59% by weight of the compound is released over the first four hours in the aqueous medium; and
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
wherein the composition has release rates by weight of compound in an aqueous medium that are release rates (a), (b) and (c), wherein:
  (a) about 15% to about 35% by weight of the compound is released over the first two hours in the aqueous medium;
  (b) about 24% to about 59% by weight of the compound is released over the first four hours in the aqueous medium; and
  (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the first excipient is present in an amount equal to about 5% to about 45% by weight and the second excipient is present in an amount equal to about 5% to about 45% by weight, in some embodiments, the first excipient is present in an amount equal to about 10% to about 40% by weight and the second excipient is present in an amount equal to about 10% to about 40% by weight. In some embodiments, the first excipient is present in an amount equal to about 12.5% to about 37.5% by weight and the second excipient is present in an amount equal to about 12.5% to about 37.5% by weight. In some embodiments, the first excipient is present in an amount equal to about 25% by weight and the second excipient is present in an amount equal to about 25% by weight.

In some embodiments provided herein is a composition having a release rate by weight of the compound as disclosed herein in an aqueous medium, wherein the release rate is the release rate measured with USP Apparatus 1 (baskets) at 100 rpm in 500 mL of an aqueous medium at a pH of 6.8 at a temperature of 37° C. 0.5° C. In some embodiments, the aqueous medium comprises sodium phosphate at a concentration of 0.05 M.

In some embodiments provided herein is a composition as disclosed herein, wherein the composition is a tablet. In some embodiments, the tablet comprises a core and a coating. In some embodiments, the core comprises one or more excipients selected from the group consisting of (1) ethers of cellulose, such as hydroxypropyl methylcellulose, (2) esters of cellulose, (3) cellulose acetate, (4) ethyl cellulose, (5) polyvinyl acetate, (6) neutral copolymers based on ethylactylate and methylmethacrylate, (7) copolymers of acrylic and methacrylic acid esters with quaternary ammonium groups, (8) pH-insensitive ammonio methacrylic acid copolymers, (9) polyethylene oxides, (10) polyvinylpyrrolidone, (11) polysaccharides of natural origin such as xanthan gum and locust bean gum, (12) polyethylene glycol, (13) polypropylene glycol, (14) castor oil, (15) triacetin, (16) tributyl citrate, (17) tri-ethyl citrate, (18) acetyl tri-n-butyl citrate, (19) diethyl phthalate, (20) dibutyl sebacate, (21) acetylated mono- and di-glycerides, and mixtures thereof. In some embodiments, the core comprises hydroxypropyl methylcellulose. In some embodiments, the coating does not comprise hydroxypropyl methylcellulose. In some embodiments, the coating does not comprise an excipient selected from the group consisting of (1) ethers of cellulose, such as hydroxypropyl methylcellulose, (2) esters of cellulose, (3) cellulose acetate, (4) ethyl cellulose, (5) polyvinyl acetate, (6) neutral copolymers based on ethylacrylate and methylmethacrylate, (7) copolymers of acrylic and methacrylic acid esters with quaternary ammonium groups, (8) pH-insensitive ammonio methacrylic acid copolymers. (9) polyethylene oxides, (10) polyvinylpyrrolidone, (11) polysaccharides of natural origin such as xanthan gum and locust bean gum, (12) polyethylene glycol, (13) polypropylene glycol, (14) castor oil, (15) triacetin, (16) tributyl citrate, (17) tri-ethyl citrate, (18) acetyl tri-n-butyl citrate, (19) diethylphthalate, (20) dibutyl sebacate, (21) acetylated mono- and di-glycerides, and mixtures thereof. In some embodiments provided herein is a tablet having one or more of release rates (a), (b) and (c) as disclosed herein, wherein the tablet comprises one or more excipients selected from the group consisting of (1) ethers of cellulose, such as hydroxypropyl methylcellulose, (2) esters of cellulose, (3) cellulose acetate, (4) ethyl cellulose, (5) polyvinyl acetate, (6) neutral copolymers based on ethylacrylate and methylmethacrylate, (7) copolymers of acrylic and methacrylic acid esters with quaternary ammonium groups, (8) pH-insensitive ammonio methacrylic acid copolymers, (9) polyethylene oxides, (10) polyvinylpyrrolidone, (11) polysaccharides of natural origin such as xanthan gum and locust bean gum, (12) polyethylene glycol, (13) polypropylene glycol, (14) castor oil, (15) triacetin, (16) tributyl citrate, (17) tri-ethyl citrate, (18) acetyl tri-n-butyl citrate, (19) diethyl phthalate, (20) dibutyl sebacate, (21) acetylated mono- and di-glycerides, and mixtures thereof. In some embodiments, the excipients are selected from the group consisting of (1) and mixtures thereof. In some embodiments, the excipients are selected from the group consisting of (2) and mixtures thereof. In some embodiments, the excipients are selected from the group consisting of (3) and mixtures thereof. In some embodiments, the excipients are selected from the group consisting of (4) and mixtures thereof. In some embodiments, the excipients are selected from the group consisting of (5) and mixtures thereof. In some embodiments, the excipients are selected from the group consisting of (6) and mixtures thereof. In some embodiments, the excipients are selected from the group consisting of (7) and mixtures thereof. In some embodiments, the excipients are selected from the group consisting of (8) and mixtures thereof. In some embodiments, the excipients are selected from the group consisting of (9) and mixtures thereof. In some embodiments, the excipients are selected from the group consisting of (10) and mixtures thereof. In some embodiments, the excipients are selected from the group consisting of (11) and mixtures thereof. In some embodiments, the excipients are selected from the group consisting of (12) and mixtures thereof. In some embodiments, the excipients are selected from the group consisting of (13) and mixtures thereof. In some embodiments, the excipients are selected from the group consisting of (14) and mixtures thereof. In some embodiments, the excipients are selected from the group consisting of (1), (2), and mixtures thereof. In some embodiments, the excipients are selected from the group consisting of (1), (3), and mixtures thereof. In some embodiments, the excipients are selected from the group consisting of (1), (4), and mixtures thereof. In some embodiments, the excipients are selected from the group consisting of (I), (5), and mixtures thereof. In some embodiments, the excipients are selected from the group consisting of (1), (6), and mixtures thereof. In some embodiments, the excipients are selected from the group consisting of (1), (7), and mixtures thereof. In some embodiments, the excipients are selected from the group consisting of (1), (8), and mixtures thereof. In some embodiments, the excipients are selected from the group consisting of (1), (9), and mixtures thereof. In some embodiments, the excipients are selected from the group consisting of (1), (10), and mixtures thereof. In some embodiments, the excipients are selected from the group consisting of (1), (11), and mixtures thereof. In some embodiments, the excipients are selected from the group consisting of (1), (12), and mixtures thereof. In some embodiments, the excipients are selected from the group consisting of (1), (13), and mixtures thereof. In some embodiments, the excipients are selected from the group consisting of (1), (14), and mixtures thereof. In some embodiments, the excipients are selected from the group consisting of (2), (3), and mixtures thereof. In some embodiments, the excipients are selected from the group consisting of (2), (4), and mixtures thereof. In some embodiments, the excipients are selected from the group consisting of (2), (5), and mixtures thereof. In some embodiments, the excipients are selected from the group consisting of (2), (6), and mixtures thereof. In some embodiments, the excipients are selected from the group consisting of (2), (7), and mixtures thereof. In some embodiments, the excipients are selected from the group consisting of (2), (8), and mixtures thereof. In some embodiments, the excipients are selected from the group consisting of (2), (9), and mixtures thereof. In some embodiments, the excipients are selected from the group consisting of (2), (10), and mixtures thereof. In some embodiments, the excipients are selected from the group consisting of (2), (11), and mixtures thereof. In some embodiments, the excipients are selected from the group consisting of (2), (12), and mixtures thereof. In some embodiments, the excipients are selected from the group consisting of (2), (13), and mixtures thereof. In some embodiments, the excipients are selected from the group consisting of (2), (14), and mixtures thereof. In some embodiments, the excipients are selected from the group consisting of (3), (4), and mixtures thereof. In some embodiments, the excipients are selected from the group consisting of (3), (5), and mixtures thereof. In some embodiments, the excipients are selected from the group consisting of (3), (6), and mixtures thereof. In some embodiments, the excipients are selected from the group consisting of (3), (7), and mixtures thereof. In some embodiments, the excipients are selected from the group consisting of (3), (8), and mixtures thereof. In some embodiments, the excipients are selected from the group consisting of (3), (9), and mixtures thereof. In some embodiments, the excipients are selected from the group consisting of (3), (10), and mixtures thereof. In some embodiments, the excipients are selected from the group consisting of (3), (11), and mixtures thereof. In some embodiments, the excipients are selected from the group consisting of (3), (12), and mixtures thereof. In some embodiments, the excipients are selected from the group consisting of (3), (13), and mixtures thereof. In some embodiments, the excipients are selected from the group consisting of (3), (14), and mixtures thereof. In some embodiments, the excipients are selected from the group consisting of (4), (5), and mixtures thereof. In some embodiments, the excipients are selected from the group consisting of (4), (6), and mixtures thereof. In some embodiments, the excipients are selected from the group consisting of (4), (7), and mixtures thereof. In some embodiments, the excipients are selected from the group consisting of (4), (8), and mixtures thereof. In some embodiments, the excipients are selected from the group consisting of (4), (9), and mixtures thereof. In some embodiments, the excipients are selected from the group consisting of (4), (10), and mixtures thereof. In some embodiments, the excipients are selected from the group consisting of (4), (11), and mixtures thereof. In some embodiments, the excipients are selected from the group consisting of (4), (12), and mixtures thereof. In some embodiments, the excipients are selected from the group consisting of (4), (13), and mixtures thereof. In some embodiments, the excipients are selected from the group consisting of (4), (14), and mixtures thereof. In some embodiments, the excipients are selected from the group consisting of (5), (6), and mixtures thereof. In some embodiments, the excipients are selected from the group consisting of (5), (7), and mixtures thereof. In some embodiments, the excipients are selected from the group consisting of (5), (8), and mixtures thereof. In some embodiments, the excipients are selected from the group consisting of (5), (9), and mixtures thereof. In some embodiments, the excipients are selected from the group consisting of (5), (10), and mixtures thereof. In some embodiments, the excipients are selected from the group consisting of (5), (11), and mixtures thereof. In some embodiments, the excipients are selected from the group consisting 4(5), (12), and mixtures thereof. In some embodiments, the excipients are selected from the group consisting of (5), (13), and mixtures thereof. In some embodiments, the excipients are selected from the group consisting of (5), (14), and mixtures thereof. In some embodiments, the excipients are selected from the group consisting of (6), (7), and mixtures thereof. In some embodiments, the excipients are selected from the group consisting of (6), (8), and mixtures thereof. In some embodiments, the excipients are selected from the group consisting of (6), (9), and mixtures thereof. In some embodiments, the excipients are selected from the group consisting of (6), (10), and mixtures thereof. In some embodiments, the excipients are selected from the group consisting of (6), (11), and mixtures thereof. In some embodiments, the excipients are selected from the group consisting of (6), (12), and mixtures thereof. In some embodiments, the excipients are selected from the group consisting of (6), (13), and mixtures thereof. In some embodiments, the excipients are selected from the group consisting of (6), (14), and mixtures thereof. In some embodiments, the excipients are selected from the group consisting of (7), (8), and mixtures thereof. In some embodiments, the excipients are selected from the group consisting of (7), (9), and mixtures thereof. In some embodiments, the excipients are selected from the group consisting of (7), (10), and mixtures thereof. In some embodiments, the excipients are selected from the group consisting of (7), (11), and mixtures thereof. In some embodiments, the excipients are selected from the group consisting of (7), (12), and mixtures thereof. In some embodiments, the excipients are selected from the group consisting of (7), (13), and mixtures thereof. In some embodiments, the excipients are selected from the group consisting of (7), (14), and mixtures thereof. In some embodiments, the excipients are selected from the group consisting of (8), (9), and mixtures thereof. In some embodiments, the excipients are selected from the group consisting of (8), (10), and mixtures thereof. In some embodiments, the excipients are selected from the group consisting of (8), (11), and mixtures thereof. In some embodiments, the excipients are selected from the group consisting of (8), (12), and mixtures thereof. In some embodiments, the excipients are selected from the group consisting of (8), (13), and mixtures thereof. In some embodiments, the excipients are selected from the group consisting of (8), (14), and mixtures thereof. In some embodiments, the excipients are selected from the group consisting of (9), (10), and mixtures thereof. In some embodiments, the excipients are selected from the group consisting of (9), (11), and mixtures thereof. In some embodiments, the excipients are selected from the group consisting of (9), (12), and mixtures thereof. In some embodiments, the excipients are selected from the group consisting of (9), (13), and mixtures thereof. In some embodiments, the excipients are selected from the group consisting of (9), (14), and mixtures thereof. In some embodiments, the excipients are selected from the group consisting of (10), (11), and mixtures thereof. In some embodiments, the excipients are selected from the group consisting of (10), (12), and mixtures thereof. In some embodiments, the excipients are selected from the group consisting of (10), (13), and mixtures thereof. In some embodiments, the excipients are selected from the group consisting of (10), (14), and mixtures thereof. In some embodiments, the excipients are selected from the group consisting of (11), (12), and mixtures thereof. In some embodiments, the excipients are selected from the group consisting of (11), (13), and mixtures thereof. In some embodiments, the excipients are selected from the group consisting of (11), (14), and mixtures thereof. In some embodiments, the excipients are selected from the group consisting of (12), (13), and mixtures thereof. In some embodiments, the excipients are selected from the group consisting of (12), (14), and mixtures thereof. In some embodiments, the excipients are selected from the group consisting, of (13), (14), and mixtures thereof. In some embodiments, the core comprises hydroxypropyl methylcellulose and the coating does not comprise hydroxypropyl methylcellulose. In some embodiments, the core comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., and the coating does not comprise hydroxypropyl methylcellulose.

In some embodiments, the tablet has a circular cross-section with a diameter of about ¼ to about ⅓ inch. In some embodiments, the tablet has a circular cross-section with a diameter of about ¼ inch. In some embodiments, the tablet has a circular cross-section with a diameter of about ⅓ inch.

In some embodiments, the tablet has a circular cross-section with a diameter of about 6.35 mm to about 8.46 mm. In some embodiments, the tablet has a circular cross-section with a diameter of about 6.35 mm. In some embodiments, the tablet has a circular cross-section with a diameter of about 8.46 mm.

In some embodiments, the oral form has content uniformity (e.g., for Compound 1). In some embodiments, the content uniformity is as measured by a content uniformity test in the international Pharmacopoeia (IP), British Pharmacopoeia (BP), United States Pharmacopoeia (USP), or European Pharmacopoeia (Ph. Eur.), which are each incorporated herein by reference. In some embodiments, the oral form has a relative standard deviation that is less than, or is less than about, 10%, 9%, 8%, 7%, 6%, 5%, 4%, 3%, 2%, 1%, or 0.5% content. In some embodiments, the oral form has no value that falls outside a range, for example 75-125%, 80-125%, 85-120%, 85-115%, 90-120%, 90-110%, or 95-105% content. In some embodiments, the oral form has no less than, or less than about, 75%, 80%, 85%, 90%, 95%, 96%, 97%, 98%, 99%, or 99.5% content. In some embodiments, the oral form has no more than, or more than about, 100.5%, 101%, 102%, 103%, 104%, 105%, 110%, 115%, 120%, or 125% content.

In some embodiments, the tablet has a hardness of about 5 kp to about 9 kp. In some embodiments, the tablet has a hardness of about 6 kp to about 8 kp. In some embodiments, the tablet has a hardness of about 7 kp.

In some embodiments, the tablet has a core weight of about 95 mg to about 105 mg. In some embodiments, the tablet has a core weight of about 97.5 mg to about 102.5 mg. In some embodiments, the tablet has a core weight of about 99 mg to about 101 mg. In some embodiments, the tablet has a core weight of about 100 mg.

In some embodiments, the tablet has a coating of about 3 mg to about 5 mg. In some embodiments, the tablet has a core weight of about 3.5 mg to about 4.5 mg in some embodiments, the tablet has a core weight of about 4 mg.

In some embodiments, the tablet has a total weight of about 98 mg to about 110 mg. In some embodiments, the tablet has a total weight of about 101 mg to about 107 mg. In some embodiments, the tablet has a total weight of about 104 mg.

In some embodiments, the therapeutically effective amount of Compound 1 in the composition is about 0.01% to about 1% by weight, such as about 0.01% to about 0.6% by weight, such as about 0.02% to about 0.3% by weight, such as about 0.03% to about 0.2% by weight, such as about 0.04% to about 0.12% by weight, such as about 0.04% to about 0, 1% by weight, such as about 0.05% to about 0.08% by weight, such as about 0.06% by weight. In some embodiments, the therapeutically effective amount of Compound 1 is about 0.025%. In some embodiments, the therapeutically effective amount of Compound 1 is about 0.03% by weight. In some embodiments, the therapeutically effective amount of Compound 1 is about 0.04%. In some embodiments, the therapeutically effective amount of Compound 1 is about 0.05% by weight. In some embodiments, the therapeutically effective amount of Compound 1 is about 0.06% by weight.

In some embodiments, the therapeutically effective amount of Compound 1 is about 0.1%. In some embodiments, the therapeutically effective amount of Compound 1 is about 0.2%. In some embodiments, the therapeutically effective amount of Compound 1 is about 0.25%. In some embodiments, the therapeutically effective amount of Compound 1 is about 0.3% by weight. In some embodiments, the therapeutically effective amount of Compound 1 is about 0.35%. In some embodiments, the therapeutically effective amount of Compound 1 is about 0.4%. In some embodiments, the therapeutically effective amount of Compound 1 is about 0.5% by weight. In some embodiments, the therapeutically effective amount of Compound 1 is about 0.6%. In some embodiments, the therapeutically effective amount of Compound 1 is about 0.7%. In some embodiments, the therapeutically effective amount of Compound 1 is about 0.75%. In some embodiments, the therapeutically effective amount of Compound 1 is about 0.8%. In some embodiments, the therapeutically effective amount of Compound 1 is about 0.9%. In some embodiments, the therapeutically effective amount of Compound 1 is about 1.0%.

In some embodiments, the therapeutically effective amount of Compound 1 in the composition is about 0.01 mg to about 1.5 mg, such as about 0.01 to about 1.45 mg, such as about 0.01 to about 1.2 mg, such as about 0.01 to about 1.0 mg, such as about 0.01 to about 0.8 mg, such as about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg.

In some embodiments provided herein is a pharmaceutical composition according to any of the embodiments described herein, wherein the therapeutically effective amount of Compound 1 is selected from, or from about, 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 tug, 0.95 mg, and 1.0 mg daily.

In some embodiments provided herein is a pharmaceutical composition according to any of the embodiments described herein, wherein the therapeutically effective amount of Compound 1 selected from 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 Mg daily.

In some embodiments, the therapeutically effective amount of Compound 1 is about 0.018 mg. In some embodiments, the therapeutically effective amount of Compound 1 is about 0.025 mg. In some embodiments, the therapeutically effective amount of Compound 1 is about 0.01 mg. In some embodiments, the therapeutically effective amount of Compound 1 is about 0.02 mg. In some embodiments, the therapeutically effective amount of Compound 1 is about 0.025 mg. In some embodiments, the therapeutically, effective amount of Compound 1 is about 0.03 mg. In some embodiments, the therapeutically effective amount of Compound 1 is about 0.04 mg. In some embodiments, the therapeutically effective amount of Compound 1 is about 0.05 mg. In some embodiments, the therapeutically effective amount of Compound 1 is about 0.06 mg. In some embodiments, the therapeutically effective amount of Compound 1 is about 0.065 mg. In some embodiments, the therapeutically effective amount of Compound 1 is about 0.07 mg. In some embodiments, the therapeutically effective amount of Compound 1 is about 0.075 mg. In some embodiments, the therapeutically effective amount of Compound 1 is about 0.08 mg. In some embodiments, the therapeutically effective amount of Compound 1 is about 0.09 mg. In some embodiments, the therapeutically effective amount of Compound 1 is about 0.1 mg. In some embodiments, the therapeutically effective amount of Compound 1 is about 0.12 mg. In some embodiments, the therapeutically effective amount of Compound 1 is about 0.15 mg. In some embodiments, the therapeutically effective amount of Compound 1 is about 0.16 mg. In some embodiments, the therapeutically effective amount of Compound 1 is about 0.2 mg. In some embodiments, the therapeutically effective amount of Compound 1 is about 0.25 mg. In some embodiments, the therapeutically effective amount of Compound 1 is about 0.3 mg. In some embodiments, the therapeutically effective amount of Compound 1 is about 0.35 mg. In some embodiments, the therapeutically effective amount of Compound 1 is about 0.4 mg. In some embodiments, the therapeutically effective amount of Compound 1 is about 0.45 mg. In some embodiments, the therapeutically effective amount of Compound 1 is about 0.5 mg. In some embodiments, the therapeutically effective amount of Compound 1 is about 0.55 mg. In some embodiments, the therapeutically effective amount of Compound 1 is about 0.6 mg. In some embodiments, the therapeutically effective amount of Compound 1 is about 0.65 mg. In some embodiments, the therapeutically effective amount of Compound 1 is about 0.7 mg. In some embodiments, the therapeutically effective amount of Compound 1 is about 0.75 mg. In some embodiments, the therapeutically effective amount of Compound 1 is about 0.8 mg. In some embodiments, the therapeutically effective amount of Compound 1 is about 0.85 mg. In some embodiments, the therapeutically effective amount of Compound 1 is about 0.9 mg. In some embodiments, the therapeutically effective amount of Compound 1 is about 0.95 mg. In some embodiments, the therapeutically effective amount of Compound 1 is about 1.0 mg. In some embodiments, the therapeutically effective amount of Compound 1 is about 1.1 mg. In some embodiments, the therapeutically effective amount of Compound 1 is about 1.2 mg. In some embodiments, the therapeutically effective amount of Compound 1 is about 1.25 mg. In some embodiments, the therapeutically effective amount of Compound 1 is about 1.3 mg. In some embodiments, the therapeutically effective amount of Compound 1 is about 1.35 mg. In some embodiments, the therapeutically effective amount of Compound 1 is about 1.4 mg. In some embodiments, the therapeutically effective amount of Compound 1 is about 1.45 mg. In some embodiments, the therapeutically effective amount of Compound 1 is about 1.5 mg.

In some embodiments, the therapeutically effective amount of Compound 1 is a starting dose.

In some embodiments provided herein is a pharmaceutical composition according to any of the embodiments described herein, wherein the therapeutically effective amount of Compound 1 is a starting dose selected from 0.01, 0.02, 0.025, 0.03, 0.04, 0.05, 0.06, 0.07, 0.075, 0.08, 0.09, or 0.1 mg daily, in some embodiments, the therapeutically effective amount of Compound 1 is a starting dose and is about 0.01 mg. In some embodiments, the therapeutically effective amount of Compound 1 is a starting dose and is about 0.02 mg. In some embodiments, the therapeutically effective amount of Compound 1 is a starting dose and is about 0.025 mg. In some embodiments, the therapeutically effective amount of Compound 1 is a starting dose and is about 0.03 mg. In some embodiments, the therapeutically effective amount of Compound 1 is a starting dose and is about 0.04 mg. In some embodiments, the therapeutically effective amount of Compound 1 is a starting dose and is about 0.05 mg. In some embodiments, the therapeutically effective amount of Corn pound 1 is a starting dose and is about 0.06 mg. In some embodiments, the therapeutically effective amount of Compound 1 is a starting dose and is about 0.07 mg. In some embodiments, the therapeutically effective amount of Compound 1 is a starting dose and is about 0.075 mg. In some embodiments, the therapeutically effective amount of Compound 1 is a starting dose and is about 0.08 mg. In some embodiments, the therapeutically effective amount of Compound 1 is a starting dose and is about 0.09 mg. In some embodiments, the therapeutically effective amount of Compound 1 is a starting dose and is about 0.1 mg.

In some embodiments, the therapeutically effective amount of Compound 1 is a highest tolerated dose.

In some embodiments provided herein is a pharmaceutical composition according to any of the embodiments described herein, wherein the therapeutically effective amount of Compound 1 is a highest tolerated dose selected from 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg daily. In some embodiments the therapeutically effective amount of Compound 1 is a highest tolerated dose and is about 0.4 mg. In some embodiments the therapeutically effective amount of Compound 1 is a highest tolerated dose and is about 0.45 mg. In some embodiments the therapeutically effective amount of Compound 1 is a highest tolerated close and is about 0.5 mg. In some embodiments the therapeutically effective amount of Compound 1 is a highest tolerated dose and is about 0.55 mg, in some embodiments the therapeutically effective amount of Compound 1 is a highest tolerated dose and is about 0.6 mg. In some embodiments the therapeutically effective amount of Compound 1 is a highest tolerated dose and is about 0.65 mg. In some embodiments the therapeutically effective amount of Compound 1 is a highest tolerated dose and is about 0.7 mg. In some embodiments the therapeutically effective amount of Compound 1 is a highest tolerated dose and is about 0.75 mg. In some embodiments the therapeutically effective amount of Compound 1 is a highest tolerated dose and is about 0.8 mg. In some embodiments the therapeutically effective amount of Compound 1 is a highest tolerated dose and is about 0.85 mg. In some embodiments the therapeutically effective amount of Compound 1 is a highest tolerated dose and is about 0.9 mg. In some embodiments the therapeutically effective amount of Compound 1 is a highest tolerated dose and is about 0.95 mg. In some embodiments the therapeutically effective amount of Compound 1 is a highest tolerated dose and is about 1.0 mg.

In some embodiments, the therapeutically effective amount of Compound 1 is a maximum dose.

In some embodiments provided herein is a pharmaceutical composition according to any of the embodiments described herein, wherein the therapeutically effective amount of Compound 1 is a maximum dose selected from 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg daily. In some embodiments the therapeutically effective amount of Compound 1 is a maximum dose and is about 0.4 mg. In some embodiments the therapeutically effective amount of Compound 1 is a maximum dose and is about 0.45 mg. In some embodiments the therapeutically effective amount of Compound 1 is a maximum dose and is about 0.5 mg. In some embodiments the therapeutically effective amount of Compound 1 is a maximum dose and is about 0.55 mg. In some embodiments the therapeutically effective amount of Compound 1 is a maximum dose and is about 0.6 mg. In some embodiments the therapeutically effective amount of Compound 1 is a maximum dose and is about 0.65 mg. In some embodiments the therapeutically effective amount of Compound 1 is a maximum dose and is about 0.7 mg. In some embodiments the therapeutically effective amount of Compound 1 is a maximum dose and is about 0.75 mg. In some embodiments the therapeutically effective amount of Compound 1 is a maximum dose and is about 0.8 mg. In some embodiments the therapeutically effective amount of Compound 1 is a maximum dose and is about 0.85 mg. In some embodiments the therapeutically effective amount of Compound 1 is a maximum dose and is about 0.9 mg, in some embodiments the therapeutically effective amount of Compound 1 is a maximum dose and is about 0.95 mg. In some embodiments the therapeutically effective amount of Compound 1 is a maximum dose and is about 1.0 mg.

In some embodiments, the therapeutically effective amount of Compound 1 is a maximum tolerated dose.

In some embodiments provided herein is a pharmaceutical composition according to any of the embodiments described herein, wherein the therapeutically effective amount of Compound 1 is a maximum tolerated dose selected from 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg daily. In some embodiments the therapeutically effective amount of Compound 1 is a maximum tolerated dose and is about 0.4 mg. In some embodiments the therapeutically effective amount of Compound 1 is a maximum tolerated dose and is about 0.45 mg. In some embodiments the therapeutically effective amount of Compound 1 is a maximum tolerated dose and is about 0.5 mg. In some embodiments the therapeutically effective amount of Compound 1 is a maximum tolerated dose and is about 0.55 mg. In some embodiments the therapeutically effective amount of Compound 1 is a maximum tolerated dose and is about 0.6 mg. In some embodiments the therapeutically effective amount of Compound 1 is a maximum tolerated close and is about 0.65 mg. In some embodiments the therapeutically effective amount of Compound 1 is a maximum tolerated close and is about 0.7 mg. In some embodiments the therapeutically effective amount of Compound 1 is a maximum tolerated dose and is about 0.75 mg. In some embodiments the therapeutically effective amount of Compound 1 is a maximum tolerated dose and is about 0.8 mg. In some embodiments the therapeutically effective amount of Compound 1 is a maximum tolerated dose and is about 0.85 mg. In some embodiments the therapeutically effective amount of Compound 1 is a maximum tolerated dose and is about 0.9 mg. In some embodiments the therapeutically effective amount of Compound 1 is a maximum tolerated dose and is about 0.95 mg. In some embodiments the therapeutically effective amount of Compound 1 is a maximum tolerated dose and is about 1.0 mg.

In some embodiments, the therapeutically effective amount of Compound 1 is a maintenance dose.

In some embodiments provided herein is a pharmaceutical composition according to any of the embodiments described herein, wherein the therapeutically effective amount of Compound 1 is a maintenance dose selected from 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 rug, 0.75 mg, 0.8 mg, 0.85 mg, 0.9 mg, 0.95 mg, and 1.0 mg daily. In some embodiments, the therapeutically effective amount of Compound 1 is a maintenance dose and is about 0.01 mg. In some embodiments, the therapeutically effective amount of Compound 1 is a maintenance dose and is about 0.02 mg. In some embodiments, the therapeutically effective amount of Compound 1 is a maintenance dose and is about 0.025 mg. In some embodiments, the therapeutically effective amount of Compound 1 is a maintenance dose and is about 0.03 mg. In some embodiments, the therapeutically effective amount of Compound 1 is a maintenance dose and is about 0.04 mg. In some embodiments, the therapeutically effective amount of Compound 1 is a maintenance dose and is about 0.05 mg. In some embodiments, the therapeutically effective amount of Compound 1 is a maintenance dose and is about 0.06 mg. In some embodiments, the therapeutically effective amount of Compound 1 is a maintenance dose and is about 0.065 mg. In some embodiments, the therapeutically effective amount of Compound 1 is a maintenance dose and is about 0.07 mg. In some embodiments, the therapeutically effective amount of Compound 1 is a maintenance dose and is about 0.075 mg, in some embodiments, the therapeutically effective amount of Compound 1 is a maintenance dose and is about 0.08 mg. In some embodiments, the therapeutically effective amount of Compound 1 is a maintenance dose and is about 0.09 mg. In some embodiments, the therapeutically effective amount of Compound 1 is a maintenance dose and is about 0.1 mg. In some embodiments, the therapeutically effective amount of Compound 1 is a maintenance dose and is about 0.12 mg. In some embodiments, the therapeutically effective amount of Compound 1 is a maintenance dose and is about 0.15 mg. In some embodiments, the therapeutically effective amount of Compound 1 is a maintenance dose and is about 0.16 mg. In some embodiments, the therapeutically effective amount of Compound 1 is a maintenance dose and is about 0.2 mg. In some embodiments, the therapeutically effective amount of Compound 1 is a maintenance dose and is about 0.25 mg. In some embodiments, the therapeutically effective amount of Compound 1 is a maintenance dose and is about 0.3 mg. In some embodiments, the therapeutically effective amount of Compound 1 is a maintenance dose and is about 0.35 mg. In some embodiments, the therapeutically effective amount of Compound 1 is a maintenance dose and is about 0.4 mg. In some embodiments, the therapeutically effective amount of Compound 1 is a maintenance dose and is about 0.45 mg. In some embodiments, the therapeutically effective amount of Compound 1 is a maintenance dose and is about 0.5 mg. In some embodiments, the therapeutically effective amount of Compound 1 is a maintenance dose and is about 0.55 mg. In some embodiments, the therapeutically effective amount of Compound 1 is a maintenance dose and is about 0.6 mg. In some embodiments, the therapeutically effective amount of Compound 1 is a maintenance dose and is about 0.65 mg. In some embodiments, the therapeutically effective amount of Compound 1 is a maintenance dose and is about 0.7 mg. In some embodiments, the therapeutically effective amount of Compound 1 is a maintenance dose and is about 0.75 mg. In some embodiments, the therapeutically effective amount of Compound 1 is a maintenance dose and is about 0.8 mg. In some embodiments, the therapeutically effective amount of Compound 1 is a maintenance dose and is about 0.85 mg. In some embodiments, the therapeutically effective amount of Compound 1 is a maintenance dose and is about 0.9 mg. In some embodiments, the therapeutically effective amount of Compound 1 is a maintenance dose and is about 0.95 mg. In some embodiments, the therapeutically effective amount of Compound 1 is a maintenance dose and is about 1.0 mg.

In some embodiments, the starting dose is for a patient. In some embodiments, the starting dose is for a patient population. In some embodiments, the highest tolerated dose is for a patient. In some embodiments, the highest tolerated dose is for a patient population. In some embodiments, the maximum dose is for a patient. In some embodiments, the maximum dose is for a patient population. In some embodiments, the maximum tolerated dose is for a patient. In some embodiments, the maximum tolerated close is for a patient population. In some embodiments, the maintenance dose is for a patient. In some embodiments, the maintenance dose is for a patient population.

In some embodiments, the starting dose of Compound 1 is selected from, or from about, 0.01, 0.02, 0.025, 0.03, 0.04, 0.05, 0.06, 0.07, 0.075, 0.08, 0.09, or 0.1 mg once daily. In some embodiments, the starting dose of Compound 1 is 0.01 mg once daily. In some embodiments, the starting dose of Compound 1 is 0.02 mg once daily. In some embodiments, the starting dose of Compound 1 is 0.05 mg once daily. In some embodiments, the starting dose of Compound 1 is 0.06 g once daily.

In some embodiments, the dose of Compound 1 is increased at weekly intervals by 0.05 mg once daily to the highest tolerated dose up to 0.8 mg once daily.

In some embodiments, the dose of Compound 1 is increased at weekly intervals. In some embodiments, the dose of Compound 1 is increased at bimonthly intervals.

In some embodiments, the dose of Compound 1 is increased by an amount selected from, or from about, 0.02 mg, 0.05 mg, 0.75 mg and 0.1 mg once daily.

In some embodiments, the dose of Compound 1 is increased at weekly intervals by an amount selected from, or from about, 0.02 mg, 0.05 mg, 0.75 mg, and 0.1 mg once daily.

In some embodiments, the highest tolerated dose of Compound 1 is selected from, or from about, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg once daily. In some embodiments, the maximum dose of Compound 1 is 0.6 mg once daily. In some embodiments, the maximum dose of Compound 1 is 0.75 mg once daily. In some embodiments, the maximum dose of Compound 1 is 0.8 mg once daily. In some embodiments, the highest tolerated dose of Compound 1 is from 0.4 to 1.0 mg once daily. In some embodiments, the highest tolerated dose of Compound 1 is from 0.6 to 1.0 mg once daily. In some embodiments, the highest tolerated dose of Compound 1 is from 0.6 to 0.8 mg once daily. In some embodiments, the highest tolerated dose of Compound 1 is from 0.65 to 1.0 mg once daily. In some embodiments, the highest tolerated dose of Compound 1 is from 0.65 to 0.8 mg once daily. In some embodiments, the highest tolerated dose of Compound 1 is greater than 0.4 mg daily. In some embodiments, the highest tolerated dose of Compound 1 is greater than 0.6 mg daily. In some embodiments, the highest tolerated dose of Compound 1 is greater than 0.8 mg daily. In some embodiments, the highest tolerated dose of Compound 1 is greater than 1.0 mg daily.

In some embodiments, the maximum dose of Compound 1 is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg once daily, in some embodiments, the maximum dose of Compound 1 is 0.6 mg once daily. In some embodiments, the maximum dose of Compound 1 is 0.75 mg, once daily. In some embodiments, the maximum dose of Compound 1 is 0.8 mg once daily. In some embodiments, the highest tolerated dose of Compound 1 is from 0.4 to 1.0 mg once daily. In some embodiments, the maximum dose of Compound 1 is from 0.6 to 1.0 mg daily. In some embodiments, the maximum dose of Compound 1 is from 0.6 to 0.8 mg once daily. In some embodiments, the maximum dose of Compound 1 is from 0.65 to 1.0 mg once daily. In some embodiments, the maximum dose of Compound 1 is from 0.65 to 0.8 mg once daily. In some embodiments, the maximum dose of Compound 1 is greater than 0.4 mg daily. In some embodiments, the maximum dose of Compound 1 is greater than 0.6 Mg daily, in some embodiments, the maximum dose of Compound 1 is greater than 0.8 mg daily. In some embodiments, the maximum dose of Compound 1 is greater than 1.0 mg daily.

In some embodiments, the maximum tolerated dose of Compound 1 is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg once daily. In some embodiments, the maximum tolerated dose of Compound 1 is 0.6 mg once daily. In some embodiments, the maximum tolerated dose of Compound 1 is 0.75 mg once daily. In some embodiments, the maximum tolerated close of Compound 1 is 0.8 mg once daily. In some embodiments, the maximum tolerated dose of Compound 1 is 0.75 mg once daily. In some embodiments, the maximum tolerated close of Compound 1 is 0.8 mg once daily. In some embodiments, the maximum tolerated dose of Compound 1 is from 0.4 to 1.0 mg once daily. In some embodiments, the maximum tolerated dose of Compound 1 is from 0.6 to 1.0 mg once daily. In some embodiments, the maximum tolerated dose of Compound 1 is from 0.6 to 0.8 mg once daily. In some embodiments, the maximum tolerated dose of Compound 1 is from 0.65 to 1.0 mg once daily. In some embodiments, the maximum tolerated dose of Compound 1 is from 0.65 to 0.8 mg once daily. In some embodiments, the maximum tolerated dose of Compound 1 is greater than 0.4 mg daily. In some embodiments, the maximum tolerated dose of Compound 1 is greater than 0.6 mg daily. In some embodiments, the maximum tolerated dose of Compound 1 is greater than 0.8 mg daily. In some embodiments, the maximum tolerated dose of Compound 1 is greater than 1.0 mg daily.

In some embodiments, the maximum dose of Compound 1 in a dosage form is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg. In some embodiments, the maximum dose of Compound 1 in a dosage form is 0.6 mg. In some embodiments, the maximum dose of Compound 1 in a dosage form is 0.75 mg. In some embodiments, the maximum dose of Compound 1 in a dosage form is 0.8 mg. In some embodiments, the maximum dose of Compound 1 is from 0.4 to 1.0 mg daily. In some embodiments, the maximum dose of Compound 1 is from 0.6 to 1.0 mg daily. In some embodiments, the maximum dose of Compound 1 is from 0.6 to 0.8 mg daily. In some embodiments, the maximum dose of Compound 1 is from 0.65 to 1.0 mg daily. In some embodiments, the maximum dose of Compound 1 is from 0.65 to 0.8 mg daily. In some embodiments, the maximum dose of Compound 1 is greater than 0.4 mg daily. In some embodiments, the maximum dose of Compound 1 is greater than 0.6 mg daily. In some embodiments, the maximum dose of Compound 1 is greater than 0.8 mg daily. In some embodiments, the maximum dose of Compound 1 is greater than 1.0 mg daily.

In some embodiments, the maintenance dose of Compound 1 is selected from, or from about, 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg daily. In some embodiments, the maintenance dose of Compound 1 is from 0.4 to 1.0 mg once daily. In some embodiments, the maintenance dose of Compound 1 is from 0.6 to 1.0 mg once daily. In some embodiments, the maintenance dose of Compound 1 is from 0.6 to 0.8 mg once daily. In some embodiments, the maintenance dose of Compound 1 is from 0.65 to 1.0 mg once daily. In some embodiments, the maintenance dose of Compound 1 is from 0.65 to 0.8 mg once daily. In some embodiments, the maintenance dose of Compound 1 is determined by tolerability. In some embodiments, the maintenance dose of Compound 1 is greater than 0.4 mg daily. In some embodiments, the maintenance dose of Compound 1 is greater than 0.6 mg daily. In some embodiments, the maintenance dose of Compound 1 is greater than 0.8 mg daily. In some embodiments, the maintenance dose of Compound 1 is greater than 1.0 mg daily.

In some embodiments, in a patient who receives a dose of Compound 1 that cannot be tolerated, the dose of Compound 1 is reduced to the previous tolerated dose. In some embodiments, the previous tolerated dose is the maximum tolerated dose for the patient.

In some embodiments, the amount of Compound 1 is adjusted to account for a difference in bioequivalence between an immediate-release form and an extended-release form. For example, in some embodiments, 0.8 mg of Compound 1 in an extended-release dosage form is provided to equate two 0.3 mg immediate-release dosage forms of Compound 1, where the extended-release dosage form has less than 100% bioequivalence with the immediate-release dosage forms.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof. In an amount equivalent to a therapeutically effective amount of Compound 1, wherein the composition comprises a first excipient and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain; and the second excipient comprises an ester of a polyalcohol and a fatty acid.

In some embodiments provided herein is a pharmaceutical composition prepared by the process comprising:

curing a mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain, and the second excipient comprise an ester of a polyalcohol and a fatty acid, to form the composition.

In some embodiments provided herein is a process for preparing a pharmaceutical composition, the process comprising:

curing a mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain, and the second excipient comprises an ester of a polyalcohol and a fatty acid, to form the composition.

In some embodiments of the compositions provided herein, the release rate is one or more of the release rates (a), (b) and/or (c) disclosed herein.

In some embodiments, the release rate is the release rate measured with USP Apparatus 1 (baskets) at 100 rpm in 500 mL of an aqueous medium at a pH of 6.8 at a temperature of 37° C.±0.5° C.

In some embodiments, the release rate is the release rate measured with USP Apparatus 1 (baskets) at 100 rpm in 500 mL of an aqueous medium at a temperature of 37° C.±0.5° C., comprising sodium phosphate at a concentration of 0.05 M.

USP Apparatus 1 (BASKETS) is described, for example, in the United States Pharmacopeial Convention, Feb. 1, 2012, Chapter <711> ("Dissolution"), incorporated by reference herein in its entirety. See http://www.usp.org/sites/default/files/usp_pdf/EN/USPNF/revisions/m99470-gc_711.pdf. The USP Apparatus 1 (baskets) assembly consists of the following: a vessel, which may be covered, made of glass or other inert, transparent material; a motor; a metallic drive shaft; and a cylindrical basket. The materials should not sorb, react, or interfere with the specimen being tested. The vessel is partially immersed in a suitable water bath of any convenient size or heated by a suitable device such as a heating jacket. The water bath or heating device permits holding the temperature inside the vessel at 37±0.5° during the test and keeping the bath fluid in constant, smooth motion. No part of the assembly, including the environment in which the assembly is placed, contributes significant motion, agitation, or vibration beyond that due to the smoothly rotating stirring element. An apparatus that permits observation of the specimen and stirring element during the test is preferable. The vessel is cylindrical, with a hemispherical bottom and with one of the following dimensions and capacities: for a nominal capacity of 1 L, the height is 160 mm to 210 mm and its inside diameter is 98 mm to 106 mm; for a nominal capacity of 2 L, the height is 280 mm to 300 mm and its inside diameter is 98 mm to 106 trim and for a nominal capacity of 4 L, the height is 280 trim to 300 mm and its inside diameter is 145 mm to 155 mm. Its sides are flanged at the top. A fitted cover may be used to retard evaporation. If a cover is used, it provides sufficient openings to allow ready insertion of the thermometer and withdrawal of specimens. The shaft is positioned so that its axis is not more than 2 min at any point from the vertical axis of the vessel and rotates smoothly and without significant wobble that could affect the results. The vertical center line of the blade passes through the axis of the shaft so that the bottom of the blade is flush with the bottom of the shaft. A distance of 25±2 mm between the bottom of the blade and the inside bottom of the vessel is maintained during the test. The metallic or suitably inert, rigid blade and shaft comprise a single entity. A suitable two-part detachable design may be used provided the assembly remains firmly engaged during the test.

A speed-regulating device is used that allows the shaft rotation speed to be selected and maintained at the specified rate within ±4%. Shaft and basket components of the stirring element are fabricated of stainless steel, type 316, or other inert material. A basket having a gold coating of about 0.0001 inch (2.5 μm) thick may be used. A dosage unit is placed in a dry basket at the beginning of each test. The distance between the inside bottom of the vessel and the bottom of the basket is maintained at 25±2 mm during the test.

USP Apparatus 2 (Paddle Apparatus) is described, for example, in the United States Pharmacopeial Convention, Feb. 1, 2012, Chapter <711> ("Dissolution"), incorporated by reference herein in its entirety. See http://www.usp.org/sites/default/files/usp_pdf/EN/USPNF/revisions/m99470-gc_711.pdf. The assembly from Apparatus 1 is used, except that a paddle formed from a blade and a shaft is used as the stirring; element. The shaft is positioned so that its axis is not more than 2 mm from the vertical axis of the vessel at any point and rotates smoothly without significant wobble that could affect the results. The vertical center line of the blade passes through the axis of the shaft so that the bottom of the blade is flush with the bottom of the shaft. A distance of 2512 min between the bottom of the blade and the inside bottom of the vessel is maintained during the test. The metallic or suitably inert, rigid blade and shaft comprise a single entity. A suitable two-part detachable design may be used provided the assembly remains firmly engaged during the test. The paddle blade and shaft may be coated with a suitable coating so as to make them inert. The dosage unit is allowed to sink to the bottom of the vessel before rotation of the blade is started. A small, loose piece of nonreactive material, such as not more than a few turns of wire helix, may be attached to dosage units that would otherwise float. Other validated sinker devices may be used.

Where water or a specified rate medium with a pH of less than 6.8 is specified as the medium, the same medium may be used with the addition of purified pepsin that results in an activity of 750,000 Units or less per 1000 mL. For media with a pH of 6.8 or greater, pancreatin can be added to produce not more than 1750 USP Units of protease activity per 1000 mL.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid, having the structure:

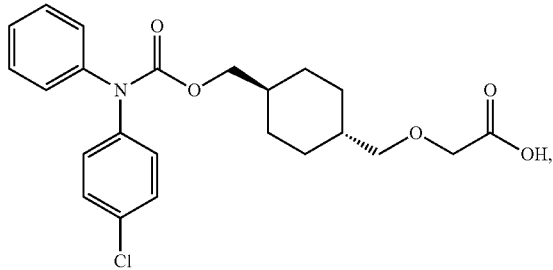

(Compound 1)

and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c), wherein:
(a) about 15% to about 35% by weight of the compound is released over the first two hours in the aqueous medium;
(b) about 24% to about 59% by weight of the compound is released over the first four hours in the aqueous medium; and/or
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid, having the structure:

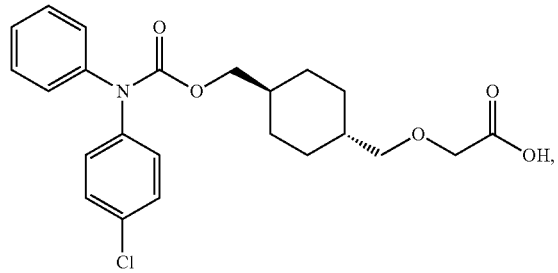

(Compound 1)

and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c), wherein:
(a) less than or equal to about 40% by weight of the compound is released over the first two hours in the aqueous medium;
(b) about 40% to about 60% by weight of the compound is released over the first five hours in the aqueous medium, and/or
(c) more than or equal to about 80% by weight of the compound is released over the first fourteen hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments, the composition has release rate (a). In some embodiments, the composition has release rate (b). In some embodiments, the composition has release rate (c). In some embodiments, the composition has release rates (a) and (b), in some embodiments, the composition has release rates (a) and (c). In some embodiments, the composition has release rates (b) and (c). In some embodiments, the composition has release rates (a), (b) and (c).

In some embodiments, the release rate is the release rate measured with USP Apparatus 1 (baskets) at 100 rpm in 500 mL of an aqueous medium at a pH of 6.8 at a temperature of 37° C.±0.5° C.

In some embodiments, the aqueous medium comprises sodium phosphate at a concentration of 0.05 M.

In some embodiments, the release rate is the release rate measured with UST Apparatus 2 (paddle) at 50 rpm in 500 mL of an aqueous medium at a pH of 6.8 at a temperature of 37° C.±0.5° C. wherein the aqueous medium comprises sodium phosphate at a concentration of 0.05 M.

In some embodiments, the composition is a tablet.

In some embodiments, the composition is a capsule.

In some embodiments, the pharmaceutical composition is a tablet.

In some embodiments, the pharmaceutical composition is a capsule.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises a release modifier having a viscosity of about 2300 mPA seconds to about 3800 mPA seconds when present in an amount of about 2% in water at 20° C. and the second excipient comprises a release modifier having a viscosity of about 75 mPA seconds to about 120 mPA seconds when present in an amount of about 2% in water at 20° C.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C.,
wherein the composition has a release rate by weight of the compound in an aqueous medium that is one or more of release rates (a), (b) and (c), wherein:
(a) about 15% to about 35% by weight of the compound is released over the first two hours in the aqueous medium;
(b) about 24% to about 59% by weight of the compound is released over the first four hours in the aqueous medium and/or
(c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises a release modifier having a viscosity of about 2300 mPA seconds to about 3800 mPA seconds when present in an amount of about 2% in water at 20° C. and the second excipient comprises a release modifier having a viscosity of about 75 mPA seconds to about 120 mPA seconds when present in an amount of about 2% in water at 20° C. wherein the composition has a release rate by weight of the compound in an aqueous medium that is one or more of release rates (a), (b) and (c), wherein:
(a) less than or equal to about 40% by weight of the compound is released over the first two hours in the aqueous medium;
(b) about 40% to about 60% by weight of the compound is released over the first five hours in the aqueous medium; and/or
(c) more than or equal to about 80% by weight of the compound is released over the first fourteen hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments, the composition has release rate (a). In some embodiments, the composition has release rate (b). In some embodiments, the composition has release rate (c), in some embodiments, the composition has release rates (a) and (b). In some embodiments, the composition has release rates (a) and (c). In some embodiments, the composition has release rates (b) and (c). In some embodiments, the composition has release rates (a), (b) and (c).

In some embodiments, the composition is a tablet.

In some embodiments, the pharmaceutical composition is a tablet.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the first excipient is present in an amount equal to about 5% to about 45% by weight and the second excipient is present in an amount equal to about 5% to about 45% by weight.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises a release modifier having a viscosity of about 2300 mPA seconds to about 3800 mPA seconds when present in an amount of about 2% in water at 20° C. and the second excipient comprises a release modifier having a viscosity of about 75 mPA seconds to about 120 mPA seconds when present in an amount of about 2% in water at 20° C., wherein the first excipient is present in an amount equal to about 5% to about 45% by weight and the second excipient is present in an amount equal to about 5% to about 45% by weight.

In some embodiments, the first excipient is present in an amount equal to about 10% to about 40% by weight and the second excipient is present in an amount equal to about 10% to about 40% by weight.

In some embodiments, the first excipient is present in an amount equal to about 12.5% to about 37.5% by weight and the second excipient is present in an amount equal to about 12.5% to about 37.5% by weight.

In some embodiments, the first excipient is present in an amount equal to about 25% by weight and the second excipient is present in an amount equal to about 25% by weight.

In some embodiments, the composition has a release rate by weight of the compound in an aqueous medium that is one or more of release rates (a), (b) and (c), wherein:
 (a) about 15% to about 35% by weight of the compound is released over the first two hours in the aqueous medium;
 (b) about 24% to about 59% by weight of the compound is released over the first four hours in the aqueous medium; and/or
 (c) about 43% to about 96% by weight of the compound is released over the first eight hours in the aqueous medium,
wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

In some embodiments, the release rate is the release rate measured with USP Apparatus 1 (baskets) at 100 rpm in 500 mL of an aqueous medium at a pH of 6.8 at a temperature of 37° C.±0.5° C.

In some embodiments, the aqueous medium comprises sodium phosphate at a concentration of 0.05 M.

In some embodiments, the release rate is the release rate measured with USP Apparatus 2 (paddle) at 50 rpm in 500 mL of an aqueous medium at a pH of 6.8 at a temperature of 37° C.±0.5° C.

In some embodiments, die aqueous medium comprises sodium phosphate at a concentration of 0.05 M.

In some embodiments, the composition is a tablet.

In some embodiments, the pharmaceutical composition is a tablet.

In some embodiments, the tablet comprises a core and a coating.

In some embodiments, the core comprises hydroxypropyl methylcellulose.

In some embodiments, the coating does not comprise hydroxypropyl methylcellulose.

In some embodiments, the core comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., and the coating does not comprise hydroxypropyl methylcellulose.

In some embodiments, the therapeutically effective amount of Compound 1 is about 0.01% to about 1% by weight of the composition.

In some embodiments, the therapeutically effective amount of Compound 1 is about 0.01% to about 0.6% by weight of the composition.

In some embodiments, the therapeutically effective amount of Compound 1 is about 0.02% to about 0.3% by weight of the composition.

In some embodiments, the therapeutically effective amount of Compound 1 is about 0.03% to about 0.2% by weight of the composition.

In some embodiments, the therapeutically effective amount of Compound 1 is about 0.04% to about 0.12% by weight of the composition.

In some embodiments, the therapeutically effective amount of Compound 1 is about 0.04% to about 0.1% by weight of the composition.

In some embodiments, the therapeutically effective amount of Compound 1 is about 0.04% to about 0.1% by weight of the composition.

In some embodiments, the therapeutically effective amount of Compound 1 is about 0.05% to about 0.08% by weight of the composition.

In some embodiments, the therapeutically effective amount of Compound 1 is about 0.06% by weight of the composition.

In some embodiments, the therapeutically effective amount of Compound 1 is about 0.01 mg to about 1 mg.

In some embodiments, the compound is 2-(((1r,4r)-(((4-chlorophenyl)(phenyl)carbamoyloxy)methyl)cyclohexyl)methoxy)acetic acid (Compound 1).

In some embodiments, the therapeutically effective amount of Compound 1 is suitable for administration to a subject once daily.

In some embodiments, the therapeutically effective amount of Compound 1 is suitable for administration to a patient once daily.

In some embodiments provided herein is a pharmaceutical composition comprising 2-(((1r,4r)-(((4-chlorophenyl)(phenyl)carbamoyloxy)methyl)cyclohexyl)methoxy)acetic acid, having the structure:

(Compound 1)

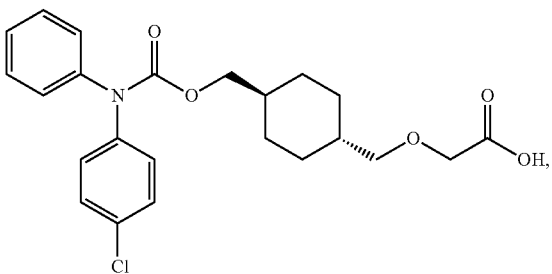

wherein the composition comprises about 0.05% by weight of Compound 1; about 25% by weight of hydroxypropyl methylcellulose having a viscosity of about 2300 mPA seconds to about 3800 mPA seconds when present in an amount of about 2% in water at 20° C.; and about 25% by weight of hydroxypropyl methylcellulose having a viscosity of about 75 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic, having the structure:

(Compound 1)

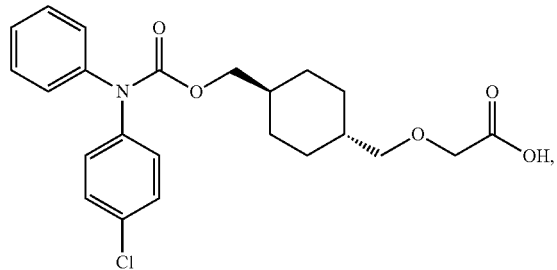

wherein the composition comprises about 0.05 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic acid, having, the structure:

(Compound 1)

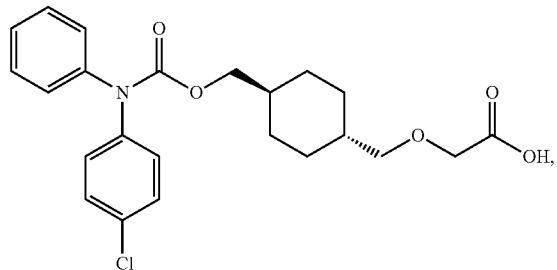

wherein the composition comprises about 0.01 mg to about 0.8 mg of Compound 1; about 5 mg to about 45 mg of hydroxypropyl methylcellulose having a viscosity of about 2300 mPA seconds to about 3800 mPA seconds when present in an amount of about 2% in water at 20° C.; and about 5 mg to about 45 mg of hydroxypropyl methylcellulose having a viscosity of about 7.5 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic acid, having, the structure:

(Compound 1)

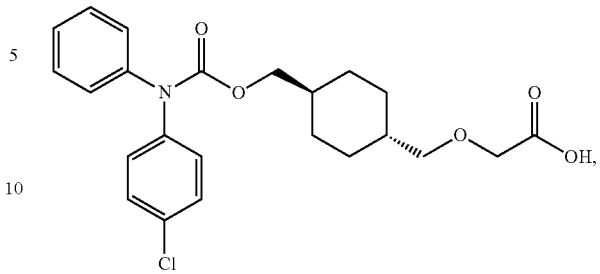

wherein the composition comprises about 0.01 mg to about 0.6 mg of Compound 1; about 5 mg to about 45 mg of hydroxypropyl methylcellulose having a viscosity of about 2300 mPA seconds to about 3800 mPA seconds when present in an amount of about 2% in water at 20° C.; and about 5 mg to about 45 mg of hydroxypropyl methylcellulose having a viscosity of about 75 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic acid, having the structure:

(Compound 1)

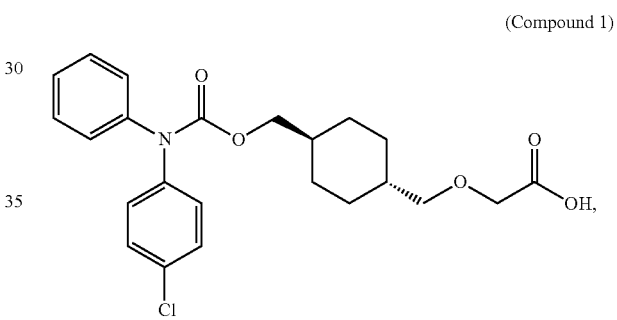

wherein the composition comprises about 0.01 mg to about 0.8 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic acid, having the structure:

(Compound 1)

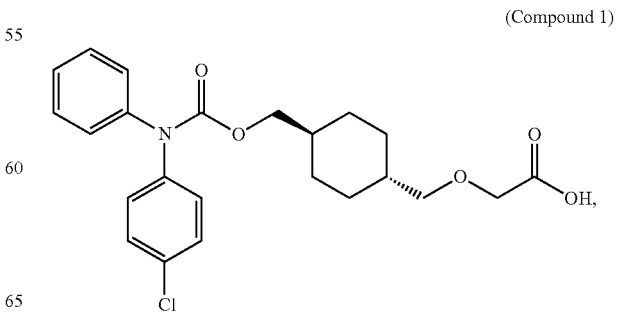

wherein the composition comprises about 0.01 mg to about 0.6 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments provided herein is a pharmaceutical composition comprising 2-(((1r,4r)-(((4-chlorophenyl)(phenyl)carbamoyloxy)methyl)cyclohexyl)methoxy)acetic acid, having the structure:

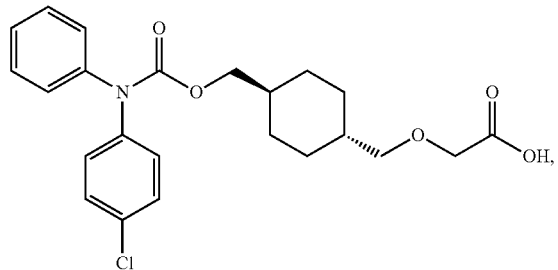

(Compound 1)

wherein the composition comprises about 0.01 mg to about 0.8 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.; about 253 mg of Methocel™ K4M Premium CR; and about 25 mg of Methocel™ K100 Premium LVCR.

In some embodiments provided herein is a pharmaceutical composition comprising 2-(((1r,4r)-(((4-chlorophenyl)(phenyl)carbamoyloxy)methyl)cyclohexyl)methoxy)acetic acid, having the structure:

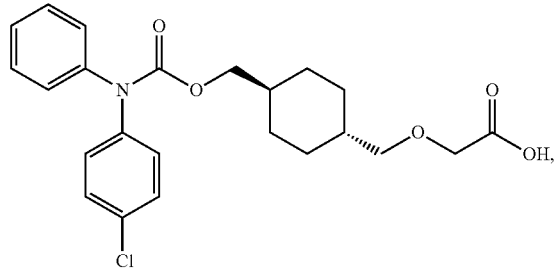

(Compound 1)

wherein the composition comprises about 0.01 mg to about 0.6 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.; about 25 mg of Methocel™ K4M Premium CR; and about 25 mg of Methocel™ K100 Premium LVCR.

In some embodiments provided herein is a process for preparing a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, comprising mixing the compound with a first excipient comprising hydroxypropyl methylcellulose having a viscosity of about 2300 mPA seconds to about 3800 mPA seconds when present in an amount of about 2% in water at 20° C., and a second excipient comprising hydroxypropyl methylcellulose having a viscosity of about 75 mPA seconds to about 120 r seconds when present in an amount of about 2% in water at 0° C., and optionally an additional pharmaceutically acceptable excipient, to form the pharmaceutical composition.

In some embodiments provided herein is a process for preparing a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, comprising mixing the compound with a first excipient comprising a release modifier having a viscosity of about 2300 mPA seconds to about 3800 mPA seconds when present in an amount of about 2% in water at 20° C., and a second excipient comprising a release modifier having a viscosity of about 75 mPA seconds to about 120 mPA seconds when present in an amount of about 2% in water at 20° C., and optionally an additional pharmaceutically acceptable excipient, to form the pharmaceutical composition.

In some embodiments provided herein is a process for preparing a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the process comprises mixing the compound, ethanol, a first excipient comprising hydroxypropyl methylcellulose having a viscosity of about 2300 mPA seconds to about 3800 mPA seconds when present in an amount of about 2% in water at 20° C. and a second excipient comprising hydroxypropyl methylcellulose having a viscosity of about 75 mPA seconds to about 120 mPA seconds when present in an amount of about 2% in water at 20° C., to form the composition.

In some embodiments, the pharmaceutical composition is a tablet.

In some embodiments provided herein is a pharmaceutical composition wherein the composition is storage-stable.

In some embodiments, the storage-stable composition is a pharmaceutical composition wherein the composition is a tablet.

In some embodiments, the storage-stable composition is a pharmaceutical composition wherein the composition is a capsule.

In some embodiments, the storage-stable composition is a pharmaceutical composition wherein the release rate of the compound after storage of the composition at 40° C. and 75% RH for at least about one month does not vary at any given dissolution time point equal or greater than 2 hours by more than about 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, in an amount equivalent to a therapeutically effective amount of Compound 1, wherein the composition comprises a first excipient and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain; and the second excipient comprises an ester of a polyalcohol and a fatty acid.

In some embodiments, the pharmaceutical composition is a composition.

In some embodiments, the first excipient comprises Poloxamer 188.

In some embodiments, the second excipient comprises glycerol monostearate and has a monoester content of at least about 90%.

In some embodiments, the second excipient comprises glycerol monostearate and has a monoester content of at least about 95%.

In some embodiments, the composition is a cured composition.

In some embodiments provided herein is a pharmaceutical composition prepared by the process comprising:
curing a mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain (b) a poly(propylene oxide) chain bonded to the first polyoxyethylene chain; and (c) a second polyoxyethylene chain bonded to the polypropylene oxide) chain, and the second excipient comprises an ester of a polyalcohol and a fatty acid, to form the composition.

In some embodiments, the first excipient comprises Poloxamer 188 and the second excipient comprises glycerol monostearate and has a monoester content of at least about 90%.

In some embodiments, the first excipient comprises Poloxamer 188 and the second excipient comprises glycerol monostearate and has a monoester content of at least about 95%.

In some embodiments, the curing of a mixture is performed at a temperature of about 45° C. to about 55° C.

In some embodiments, the curing of a mixture is performed for about 12 hours to about 36 hours at a temperature of about 50° C. to about 55° C.

In some embodiments, the ratio by weight of the first excipient to the second excipient is from about 70:30 to about 10:90.

In some embodiments, the ratio by weight of the first excipient to the second excipient is about 50:50 to about 30:70.

In some embodiments, the ratio by weight of the first excipient to the second excipient is about 70:30.

In some embodiments, the ratio by weight of the first excipient to the second excipient is about 50:50.

In some embodiments, the ratio by weight of the first excipient to the second excipient is about 40:60.

In some embodiments, the ratio by weight of the first excipient to the second excipient is about 30:70.

In some embodiments, the composition has a release rate by weight of the compound in an aqueous medium that is one or more of release rates (a), (b) and (c), wherein:
(a) about 15% to about 35% of the compound is released over the first two hours in the aqueous medium;
(b) about 24% to about 59% of the compound is released over the first four hours in the aqueous medium; and/or
(c) about 43% to about 96% of the compound is released over the first eight hours in the aqueous medium.

In some embodiments, the composition has release rate (a).

In some embodiments, the composition has release rate (b).

In some embodiments, the composition has release rate (c).

In some embodiments, the composition has release rates (a) and (b).

In some embodiments, the composition has release rates (a) and (c).

In some embodiments, the composition has release rates (b) and (c).

In some embodiments, the composition has release rates (a), (b) and (c).

In some embodiments, the composition is a capsule.

In some embodiments, the release rate is the release rate measured with USP Apparatus 2 (paddle) at 50 rpm in 500 of an aqueous medium at a pH of 6.8 at a temperature of 37° C.±0.5° C.

In some embodiments, the aqueous medium comprises sodium phosphate at a concentration of 0.05 M.

In some embodiments, the compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof is 2-(((1r,4r)-(((4-chlorophenyl)(phenyl)carbamoyloxy)methyl)cyclohexyl)methoxy)acetic acid (Compound 1).

In some embodiments, the composition exhibits peaks in the PXRD spectrum having the following 2□ values: 19.7°, 20.2°, 20.7°, 22.6°, 23°, and 23.7°.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid, having; the structure:

(Compound 1)

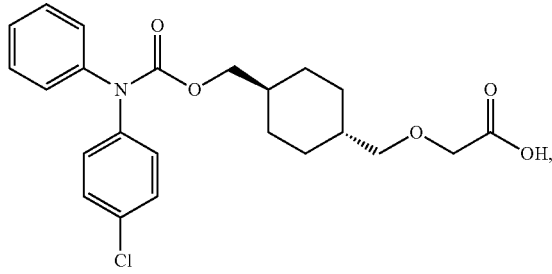

and pharmaceutically acceptable salts, solvates, and hydrates thereof, in an amount equivalent to a therapeutically effective amount of Compound 1, the composition having a release rate by weight of the compound in an aqueous medium that is one or more of release rates (a), (b) and (c), wherein:

(a) about 15% to about 35% by weight of the compound is released over the first two hours in the aqueous medium;
(b) about 24% to about 59% by weight of the compound is released over the first four hours in the aqueous medium; and/or
(c) about 43% to about 96% by weight of the compound is released over the first eight hours in the aqueous medium, wherein the release rate is measured with USP Apparatus 1 (baskets) at 80 to 120 rpm in 400 to 600 mL, of an aqueous medium at a pH of 6.3 to 7.3 at a temperature of 37° C.±0.5° C., comprising sodium phosphate at a concentration of 0.04 to 0.06 M, wherein the composition comprises a first excipient and a second excipient, wherein the first excipient comprises a copolymer comprising (a) a first polyoxyethylene chain; (b) a polypropylene oxide) chain bonded to the first polyoxyethylene chain; and (c) a second polyoxyethylene chain bonded to the polypropylene oxide) chain; and the second excipient comprises an ester of a polyalcohol and a fatty acid.

In some embodiments of the pharmaceutical compositions disclosed herein, the first excipient comprises Poloxamer 188.

In some embodiments of the pharmaceutical compositions disclosed herein, the second excipient comprises glycerol monostearate and has a monoester content of at least about 50%. In some embodiments, the second excipient comprises glycerol monostearate and has a monoester content of at least about 60%, such as at least about 70%, such as at least about 75%, such as at least about 80%, such as at least about 90%, such as at least about 95%, such as at least about 96%, such as at least about 97%, such as at least about 98%, such as at least about 99%.

In some embodiments of the pharmaceutical compositions disclosed herein, the ratio by weight of the first excipient to the second excipient is about 30:70.

In some embodiments of the pharmaceutical compositions disclosed herein, the first excipient comprises Poloxamer 188 and the second excipient comprises glycerol monostearate and has a monoester content of at least about 90%, wherein the ratio by weight of the first excipient to the second excipient is about 30:70.

In some embodiments of the pharmaceutical compositions disclosed herein, the first excipient comprises Poloxamer 188 and the second excipient comprises glycerol monostearate and has a monoester content of at least about 95%, wherein the ratio by weight of the first excipient to the second excipient is about 30:70.

In some embodiments, the pharmaceutical composition is a dosage form composed of a size 4 gelatin capsule, such as a white opaque, hard gelatin capsule. In some embodiments, the pharmaceutical composition is a dosage form composed of a size 2 gelatin capsule, such as a white opaque, hard gelatin capsule. In some embodiments, the pharmaceutical composition is a dosage form composed of a size 4 HPMC capsule. In some embodiments, the pharmaceutical composition is a dosage form composed of a size 2 HPMC capsule.

In some embodiments of the pharmaceutical compositions disclosed herein, the compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof is 2-(((1r,4r)-(((4-chlorophenyl)(phenyl)carbamoyloxy)methyl)cyclohexyl)methoxy)acetic acid (Compound 1).

In some embodiments of the pharmaceutical compositions disclosed herein, the compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof is a pharmaceutically acceptable salt of 2-(((1r,4r)-(((4-chlorophenyl)(phenyl)carbamoyloxy)methyl)cyclohexyl)methoxy)acetic acid (Compound 1).

In some embodiments, the therapeutically effective amount of Compound 1 is suitable for administration to a subject, such as a patient, once daily.

In some embodiments, the therapeutically effective amount of Compound 1 is suitable for administration to a subject, such as a patient, twice daily.

In some embodiments, the pharmaceutical composition contains a release modifier. In some embodiments, the release modifier is hydroxypropyl methylcellulose. For example, in some embodiments, the release modifier is hydroxypropyl methylcellulose K4M CR and/or hydroxypropyl methylcellulose K100 LCR. In some embodiments, the release modifier is a resin. For example, in some embodiments, the release modifier is an ethylene oxide resin (such as Polyox® resin), in some embodiments, the release modifier is another excipient known in the pharmaceutical art to modify release of an active agent.

In some embodiments, the pharmaceutical composition contains a filler. For example, in some embodiments, the pharmaceutical composition contains microcrystalline cellulose. In some embodiments, the filler is another excipient known in the pharmaceutical art. In some embodiments, the pharmaceutical composition contains a glidant. For example, in some embodiments, the pharmaceutical composition contains silicon dioxide. In some embodiments, the glidant is another excipient known in the pharmaceutical art.

In some embodiments, the pharmaceutical composition contains a lubricant. For example, in some embodiments, the pharmaceutical composition contains magnesium stearate. In some embodiments, the lubricant is another excipient known in the pharmaceutical art. In some embodiments, the pharmaceutical composition contains a film coating. For example, in some embodiment, the pharmaceutical composition contains Opadry®. In some embodiments, the film coating is another excipient known in the pharmaceutical art.

In some embodiments, the pharmaceutical composition is in the form of, for example, granules, spheroids or pellets in a capsule or in any other suitable dosage form. In some embodiment; the pharmaceutical composition is in the form of a capsule, such as a hard gelatin capsule. In some embodiments, the pharmaceutical composition is in the form of a tablet.

In addition to the above ingredients, the pharmaceutical composition may further comprise suitable quantities of other materials, e.g. stabilizers, diluents, lubricants, binders, granulating aids, colorants, flavorants and glidants that are conventional in the pharmaceutical art.

In some embodiments, the pharmaceutical composition herein comprises Compound; hydroxypropyl methylcellulose having a viscosity of about 2300 mPA seconds to about 3800 mPA seconds when present in an amount of about 2% in water at 20° C.; and hydroxypropyl methylcellulose having a viscosity of about 75 mPA seconds to about 120 mPA seconds when present in an amount of about 2% in water at 20° C., the composition comprising about 0.01% to about 1% of Compound 1 as a I/O by weight of the composition, such as about 0.02% to about 0.5%, such as about 0.03% to about 0.4%, such as about 0.05% to about 0.2%, such as about 0.03%, about 0.5%, about 0.1%, 0.2% or 0.5%, of Compound 1 as a % by weight of the composition.

In some embodiments, the pharmaceutical composition comprises about 0.03% by weight of Compound 1; about 5% to about 45% by weight of hydroxypropyl methylcellulose having a viscosity of about 2300 mPA seconds to about 3800 mPA seconds when present in an amount of about 2% in water at 20° C. (the first excipient); and about 5% to about 45% by weight of hydroxypropyl methylcellulose having a viscosity of about 75 mPA seconds to about 120 mPA seconds when present in an amount of about 2% in water at 20° C. (the second excipient). In some embodiments, the composition comprises about 0.03% by weight of Compound 1; about 10% to about 40% by weight of the first excipient; and about 10% to about 40% by weight of the second excipient. In some embodiments, the composition comprises about 0.03% by weight of Compound 1; about 12.5% to about 37.5% by weight of the first excipient; and about 12.5% to about 37.5% by weight of the second excipient. In some embodiments, the composition comprises about 0.03% by weight of Compound 1; about 25% by weight of hydroxypropyl methylcellulose having a viscosity of about 2300 mPA seconds to about 3800 mPA seconds when present in an amount of about 2% in water at 20° C.; and about 25% by weight of hydroxypropyl methylcellulose having a viscosity of about 75 mPA seconds to about 120 mPA seconds when present in an amount of about 2% in water at 20° C.

In some embodiments, the pharmaceutical composition comprises about 0.05% by weight of Compound 1; about 5% to about 45% by weight of hydroxypropyl methylcellulose having a viscosity of about 2300 mPA seconds to about 3800 mPA seconds when present in an amount of about 2% in water at 20° C. (the first excipient); and about 5% to about 45% by weight of hydroxypropyl methylcellulose having a viscosity of about 75 mPA seconds to about 120 mPA seconds when present in an amount of about 2% in water at 20° C. (the second excipient). In some embodiments, the composition comprises about 0.05% by weight of Compound 1; about 10% to about 40% by weight of the first excipient; and about 10% to about 40% by weight of the second excipient. In some embodiments, the composition comprises about 0.05% by weight of Compound 1; about 12.5% to about 37.5% by weight of the first excipient; and about 12.5% to about 37.5% by weight of the second excipient. In some embodiments, the composition comprises about 0.05% by weight of Compound 1; about 25% by weight of hydroxypropyl methylcellulose having a viscosity of about 2300 mPA seconds to about 3800 mPA seconds when present in an amount of about 2% in water at 20° C.; and about 25% by weight of hydroxypropyl methylcellulose having a viscosity of about 75 mPA seconds to about 120 mPA seconds when present in an amount of about 2% in water at 20° C.

In some embodiments, the pharmaceutical composition comprises about 0.1% by weight of Compound 1; about 5% to about 45% by weight of hydroxypropyl methylcellulose having a viscosity of about 2300 mPA seconds to about 3800 mPA seconds when present in an amount of about 2% in water at 20° C. (the first excipient); and about 5% to about 45% by weight of hydroxypropyl methylcellulose having a viscosity of about 75 mPA seconds to about 120 mPA seconds when present in an amount of about 2% in water at 20° C. (the second excipient). In some embodiments, the composition comprises about 0.1% by weight of Compound 1; about 10% to about 40% by weight of the first excipient; and about 10% to about 40% by weight of the second excipient. In some embodiments, the composition comprises about 0.1% by weight of Compound 1; about 12.5% to about 37.5% by weight of the first excipient; and about 12.5% to about 37.5% by weight of the second excipient. In some embodiments, the composition comprises about 0.1% by weight of Compound 1; about 25% by weight of hydroxypropyl methylcellulose having a viscosity of about 2300 mPA seconds to about 3800 mPA seconds when present in an amount of about 2% in water at 20° C.; and about 25% by weight of hydroxypropyl methylcellulose having a viscosity of about 75 mPA seconds to about 120 mPA seconds when present in an amount of about 2% in water at 20° C.

In some embodiments, the pharmaceutical composition herein comprises about 0.03 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments, the pharmaceutical composition herein comprises about 0.05 mg of Compound 1; about 25 mg of hydroxypropyl methylcellulose having a viscosity of about 2300 mPA seconds to about 3800 mPA seconds when present in an amount of about 2% In water at 20° C.; and about 25 mg of hydroxypropyl methylcellulose having a viscosity of about 75 mPA seconds to about 120 mPA seconds when present in an amount of about 2% in water at 20° C.

In some embodiments, the pharmaceutical composition herein comprises about 0.1 mg of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments, the pharmaceutical composition herein comprises an amount equivalent to about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg of Compound 1; about 5 mg to about 45 mg, such as about 10 mg, about 15 mg, about 20 mg, about 25 mg, about 30 mg, about 35 mg, or about 40 mg, of hydroxypropyl methylcellulose having a viscosity of about 2300 mPA seconds to about 3800 mPA seconds when present in an amount of about 2% in water at 20° C.; and about 5 mg to about 45 mg, such as about 10 mg, about 15 mg, about 20 mg, about 25 mg, about 30 mg, about 35 mg, or about 40 mg, of hydroxypropyl methylcellulose having a viscosity of about 75 mPA seconds to about 120 mPA seconds when present in an amount of about 2% in water at 20° C.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 008 mg, such as about 0.06 mg, of Compound 1; about 25 mg of hydroxypropyl methylcellulose having a viscosity of about 2300 mPA seconds to about 3800 mPA seconds when present in an amount of about 2% in water at 20° C.; and about 25 mg of hydroxypropyl methylcellulose having a viscosity of about 75 mPA seconds to about 120 mPA seconds when present in an amount of about 2% in water at 20° C.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg of Compound 1, about 25 mg of Methocel™ K4M Premium CR; and about 25 mg of Methocel™ K100 Premium LVCR.

In some embodiments, the pharmaceutical composition herein comprises Compound 1; Poloxamer 188; and food grade glycerol monostearate; the composition comprising about 0.0066% to about 0.666% of Compound 1 as a % by weight of the composition.

In some embodiments, the pharmaceutical composition herein comprises Compound 1; Poloxamer 188; and food grade glycerol monostearate; the composition comprising about 0.0066% to about 0.4% of Compound 1 as a % by weight of the composition.

In some embodiments, the pharmaceutical composition herein comprises Compound 1; Poloxamer 188; and food grade glycerol monostearate; the composition comprising about 0.0133% to about 0.2% of Compound 1 as a % by weight of the composition.

In some embodiments, the pharmaceutical composition herein comprises Compound 1; Poloxamer 188; and food grade glycerol monostearate; the composition comprising about 0.02% to about 0.133% of Compound 1 as a % by weight of the composition.

In some embodiments, the pharmaceutical composition herein comprises Compound 1; Poloxamer 188; and food grade glycerol monostearate; the composition comprising about 0.0266% to about 0.066% of Compound 1 as a % by weight of the composition.

In some embodiments, the pharmaceutical composition herein comprises Compound 1; Poloxamer 188; and food grade glycerol monostearate; the composition comprising about 0.0333% to about 0.066% of Compound 1 as a % by weight of the composition.

In some embodiments, the pharmaceutical composition herein comprises Compound 1; Poloxamer 188; and food grade glycerol monostearate; the composition comprising about 0.04% of Compound 1 as a % by weight of the composition.

In some embodiments, the pharmaceutical composition herein comprises Compound 1; Poloxamer 188; and glycerol monostearate having a monoester content of at least about 90%; the composition comprising about 0.0066% to about 0.666% of Compound 1 as a % by weight of the composition.

In some embodiments, the pharmaceutical composition herein comprises Compound 1; Poloxamer 188; and glycerol monostearate having a monoester content of at least about 90%: the composition comprising about 0.0066% to about 0.4% of Compound 1 as a % by weight of the composition.

In some embodiments, the pharmaceutical composition herein comprises Compound 1; Poloxamer 188; and glycerol monostearate having a monoester content of at least about 90%; the composition comprising about 0.0133% to about 0.2% of Compound 1 as a ° Jo by weight of the composition.

In some embodiments, the pharmaceutical composition herein comprises Compound 1; Poloxamer 188; and glycerol monostearate having a monoester content of at least about 90%; the composition comprising about 0.02% to about 0.133% of Compound 1 as a % by weight of the composition.

In some embodiments, the pharmaceutical composition herein comprises Compound 1; Poloxamer 188; and glycerol monostearate having a monoester content of at least about 90%; the composition comprising about 0.0266% to about 0.066% of Compound 1 as a % by weight of the composition.

In some embodiments, the pharmaceutical composition herein comprises Compound 1; Poloxamer 188; and glycerol monostearate having a monoester content of at least about 90%; the composition comprising about 0.0333% to about 0.066% of Compound 1 as a % by weight of the composition.

In some embodiments, the pharmaceutical composition herein comprises Compound 1; Poloxamer 188; and glycerol monostearate having a monoester content of at least about 90%; the composition comprising about 0.04% of Compound 1 as a % by weight of the composition.

In some embodiments the pharmaceutical composition herein comprises Compound 1; Poloxamer 188; and glycerol monostearate having a monoester content of at least about 95%; the composition comprising about 0.0066% to about 0.666% of Compound 1 as a ° Jo by weight of the composition.

In some embodiments, the pharmaceutical composition herein comprises Compound 1; Poloxamer 188; and glycerol monostearate having a monoester content of at least about 95%; the composition comprising about 0.0066% to about 0.4% of Compound 1 as a % by weight of the composition.

In some embodiments, the pharmaceutical composition herein comprises Compound 1; Poloxamer 188; and glycerol monostearate having a monoester content of at least about 95%; the composition comprising about 0.0133% to about 0.2% of Compound 1 as a % by weight of the composition.

In some embodiments, the pharmaceutical composition herein comprises Compound 1; Poloxamer 188, and glycerol monostearate having a monoester content of at least about 95%; the composition comprising about 0.02% to about 0.133% of Compound 1 as a % by weight of the composition.

In some embodiments, the pharmaceutical composition herein comprises Compound 1; Poloxamer 188; and glycerol monostearate having a monoester content of at least about 95%; the composition comprising about 0.0266% to about 0.066% of Compound 1 as a % by weight of the composition.

In some embodiments, the pharmaceutical composition herein comprises Compound 1; Poloxamer 188; and glycerol monostearate having a monoester content of at least about 95%; the composition comprising about 0.0333% to about 0.066% of Compound 1 as a % by weight of the composition.

In some embodiments, the pharmaceutical composition herein comprises Compound 1; Poloxamer 188; and glycerol monostearate having a monoester content of at least about 95%; the composition comprising about 0.04% of Compound 1 as a % by weight of the composition.

In some embodiments, the pharmaceutical composition herein comprises an amount equivalent to about 0.01 mg to about 0.6 g, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 45 mg to about 135 mg, such as about 45 mg, about 60 mg, about 75 mg, about 90 mg, about 105 mg, about 120 mg, or about 135 mg, of food grade GMS; and about 105 mg to about 15 mg, such as about 105 mg, about 90 mg, about 75 mg, about 60 mg, about 45 mg, about 30 mg, or about 15 mg, of Poloxamer 188. In some embodiments, the composition herein comprises about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.12 mg, about 0.2 mg, about 0.3 mg, or about 0.5 mg, or about 0.6 mg, of Compound 1; about 45 mg to about 135 mg, such as about 60 mg, about 75 mg, about 90 mg, about 105 mg, about 120 mg, or about 135 mg, of food grade GMS; and about 105 mg to about 15 mg, such as about 105 mg, about 90 mg, about 75 mg, about 60 mg, about 45 mg, about 30 mg, or about 15 mg, of Poloxamer 188.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 75 mg of Poloxamer 188; and about 75 mg of food grade glycerol monostearate.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 45 mg of Poloxamer 188; and about 105 mg of food grade glycerol monostearate.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 105 mg of Poloxamer 188; and about 45 mg of food grade glycerol monostearate.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg of Compound 1; about 75 mg of Poloxamer 188; and about 75 mg of glycerol monostearate having a monoester content of at least about 90%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 45 mg of Poloxamer 188; and about 105 mg of glycerol monostearate having a monoester content of at least about 90%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound about 105 mg of Poloxamer 188; and about 45 mg of glycerol monostearate having a monoester content of at least about 90%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 75 mg of Poloxamer 188; and about 75 mg of glycerol monostearate having a monoester content of at least about 95%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 45 mg of Poloxamer 188; and about 105 mg of glycerol monostearate having a monoester content of at least about 95%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 105 mg of Poloxamer 188; and about 45 mg of glycerol monostearate having a monoester content of at least about 95%.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg such as about 0.04 to about 0.1 mg, such as about 0.05 to about 0.08 mg, such as about 0.06 mg, of Compound 1; about 75 mg of Poloxamer 188; and about 75 mg of Myverol™ 18-04 K.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 45 mg of Poloxamer 188; and about 105 mg of Myverol™ 18-04 K.

In some embodiments, the pharmaceutical composition herein comprises about 0.01 mg to about 0.6 mg, such as about 0.02 to about 0.3 mg, such as about 0.03 to about 0.2 mg, such as about 0.04 to about 0.12 mg, such as about 0.04 to about 0.1 mg, such as about 0.05 to about 0.08 mg, such as about 0.06 mg, of Compound 1; about 105 mg of Poloxamer 188; and about 45 rug of Myverol™ 18-04 K.

In some embodiments, the pharmaceutical composition herein comprises about 0.03 mg of Compound 1; about 75 mg of Poloxamer 188; and about 75 mg of food grade glycerol monostearate.

In some embodiments, the pharmaceutical composition herein comprises about 0.03 mg of Compound 1; about 45 mg of Poloxamer 188; and about 105 mg of food grade glycerol monostearate.

In some embodiments, the pharmaceutical composition herein comprises about 0.03 mg of Compound 1; about 105 mg of Poloxamer 188; and about 45 mg of food grade glycerol monostearate.

In some embodiments, the pharmaceutical composition herein comprises about 0.03 mg of Compound 1; about 75 mg of Poloxamer 188; and about 75 mg of glycerol monostearate having a monoester content of at least about 90%.

In some embodiments, the pharmaceutical composition herein comprises about 0.03 mg of Compound 1; about 45 mg of Poloxamer 188; and about 105 mg of glycerol monostearate having a monoester content of at least about 90%.

In some embodiments, the pharmaceutical composition herein comprises about 0.03 mg of Compound 1; about 105 mg of Poloxamer 188; and about 45 mg of glycerol monostearate having a monoester content of at least about 90%.

In some embodiments, the pharmaceutical composition herein comprises about 0.03 mg of Compound 1; about 75 mg of Poloxamer 188; and about 75 mg of glycerol monostearate having a monoester content of at least about 95%.

In some embodiments, the pharmaceutical composition herein comprises about 0.03 mg of Compound 1; about 45 mg of Poloxamer 188; and about 105 mg of glycerol monostearate having a monoester content of at least about 95%.

In some embodiments, the pharmaceutical composition herein comprises about 0.03 mg of Compound 1, about 105 mg of Poloxamer 188; and about 45 mg of glycerol monostearate having a monoester content of at least about 95%.

In some embodiments, the pharmaceutical composition herein comprises about 0.03 mg of Compound 1; about 75 mg of Poloxamer 188; and about 75 mg of Myverol™ 18-04 K.

In some embodiments, the pharmaceutical composition herein comprises about 0.03 mg of Compound 1; about 45 mg of Poloxamer 188; and about 105 mg of Myverol™ 18-04 K.

In some embodiments, the pharmaceutical composition herein comprises about 0.03 mg of Compound 1; about 105 mg of Poloxamer 188; and about 45 mg of Myverol™ 18-04 K.

In some embodiments, the pharmaceutical composition herein comprises about 0.5 mg of Compound 1; about 75 mg of Poloxamer 188; and about 75 mg of food grade glycerol monostearate.

In some embodiments, the pharmaceutical composition herein comprises about 0.5 mg of Compound 1; about 45 mg of Poloxamer 188; and about 105 mg of food grade glycerol monostearate.

In some embodiments, the pharmaceutical composition herein comprises about 0.5 mg of Compound 1; about 105 mg of Poloxamer 188; and about 45 mg of food grade glycerol monostearate.

In some embodiments, the pharmaceutical composition herein comprises about 0.5 mg of Compound 1; about 75 mg of Poloxamer 188; and about 75 mg of glycerol monostearate having a monoester content of at least about 90%.

In some embodiments, the pharmaceutical composition herein comprises about 0.5 mg of Compound 1; about 45 mg of Poloxamer 188; and about 105 mg of glycerol monostearate having a monoester content of at least about 90%.

In some embodiments, the pharmaceutical composition herein comprises about 0.5 mg of Compound 1; about 105 mg of Poloxamer 188; and about 45 mg of glycerol monostearate having a monoester content of at least about 90%.

In some embodiments, the pharmaceutical composition herein comprises about 0.5 mg of Compound 1; about 75 mg of Poloxamer 188; and about 75 mg of glycerol monostearate having a monoester content of at least about 95%.

In some embodiments, the pharmaceutical composition herein comprises about 0.5 mg of Compound 1; about 45 mg of Poloxamer 188; and about 105 mg of glycerol monostearate having a monoester content of at least about 95%.

In some embodiments, the pharmaceutical composition herein comprises about 0.5 mg of Compound 1; about 105 mg of Poloxamer 188; and about 45 mg of glycerol monostearate having a monoester content of at least about 95%.

In some embodiments, the pharmaceutical composition herein comprises about 0.5 mg of Compound 1; about 75 mg of Poloxamer 188; and about 75 mg of Myverol™ 18-04 K.

In some embodiments, the pharmaceutical composition herein comprises about 0.5 mg of Compound 1; about 45 mg of Poloxamer 188; and about 105 mg of Myverol™ 18-04 K.

In some embodiments, the pharmaceutical composition herein comprises about 0.5 mg of Compound 1; about 105 mg of Poloxamer 188; and about 45 mg of Myverol™ 18-04 K.

In some embodiments, the pharmaceutical composition herein comprises about 0.12 mg of Compound 1; about 75 mg of Poloxamer 188; and about 75 mg of food grade glycerol monostearate.

In some embodiments, the pharmaceutical composition herein comprises about 0.12 mg of Compound 1; about 45 mg of Poloxamer 188; and about 105 mg of food grade glycerol monostearate.

In some embodiments, the pharmaceutical composition herein comprises about 0.12 mg of Compound 1; about 105 mg of Poloxamer 188; and about 45 mg of food grade glycerol monostearate.

In some embodiments, the pharmaceutical composition herein comprises about 0.12 mg of Compound 1; about 75 mg of Poloxamer 188; and about 75 mg of glycerol monostearate having a monoester content of at least about 90%.

In some embodiments, the pharmaceutical composition herein comprises about 0.12 mg of Compound 1; about 45 mg of Poloxamer 188; and about 105 mg of glycerol monostearate having a monoester content of at least about 90%.

In some embodiments, the pharmaceutical composition herein comprises about 0.12 mg of Compound 1; about 105 mg of Poloxamer 188; and about 45 mg of glycerol monostearate having a monoester content of at least about 90%.

In some embodiments, the pharmaceutical composition herein comprises about 0.12 mg of Compound 1; about 75 mg of Poloxamer 188; and about 75 mg of glycerol monostearate having a monoester content of at least about 95%.

In some embodiments, the pharmaceutical composition herein comprises about 0.12 mg of Compound 1; about 45 mg of Poloxamer 188; and about 105 mg of glycerol monostearate having a monoester content of at least about 95%.

In some embodiments, the pharmaceutical composition herein comprises about 0.12 mg of Compound 1; about 105 mg of Poloxamer 188; and about 45 mg of glycerol monostearate having a monoester content of at least about 95%.

In some embodiments, the pharmaceutical composition herein comprises about 0.12 mg of Compound 1; about 75 mg of Poloxamer 188; and about 75 mg of Myverol™ 18-04 K.

In some embodiments, the pharmaceutical composition herein comprises about 0.12 mg of Compound 1; about 45 mg of Poloxamer 188; and about 105 mg of Myverol™ 18-04 K.

In some embodiments, the pharmaceutical composition herein comprises about 0.12 mg of Compound 1; about 105 mg of Poloxamer 188; and about 45 mg of Myverol™ 18-04 K.

In any of the embodiments wherein the composition comprises glycerol monostearate having a monoester content of at least about 95%, the glycerol monostearate may have a monoester content that is at least about 96%, such as at least about 97%, such as at least about 98%, such as at least about 99%.

In some embodiments, provided herein is a pharmaceutical composition having a release rate by weight of the compound in an aqueous medium that is one or more of the release rates (a), (b) and/or (c) disclosed herein, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the ratio by weight of the first excipient to the second excipient is about 50:50, wherein the release rate is the release rate measured with USP Apparatus 1 (baskets) at 100 rpm in 500 mL of an aqueous medium at a temperature of 37° C.±0.5° C. at a pH of about 6.8, wherein the aqueous medium comprises sodium phosphate at a concentration of 0.05 M.

In some embodiments, provided herein is a pharmaceutical composition having a release rate by weight of the compound in an aqueous medium that is one or more of the release rates (a), (b) and/or (c) disclosed herein, wherein the composition comprises a first excipient and a second excipient, wherein the first excipient comprises hydroxypropyl methylcellulose having a viscosity of about 2300 mPA seconds to about 3800 mPA seconds when present in an amount of about 2% in water at 20° C. and the second excipient comprises hydroxypropyl methylcellulose having a viscosity of about 75 mPA seconds to about 120 mPA seconds when present in an amount of about 2% in water at 20° C., wherein the first excipient is present in an amount equal to about 25% by weight and the second excipient is present in an amount equal to about 25% by weight, wherein the release rate is the release rate measured with USP Apparatus 1 (baskets) at 100 rpm in 500 mL of an aqueous medium at a temperature of 37° C.±0.5° C. at a pH of about 6.8, wherein the aqueous medium comprises sodium phosphate at a concentration of 0.05 M.

In some embodiments, provided herein is a pharmaceutical composition having a release rate by weight of Compound 1 in an aqueous medium that is one or more of release rates (a), (b) and (c) herein, wherein the composition comprises a first excipient and a second excipient, wherein the first excipient is Poloxamer 188 and the second excipient is glycerol monostearate and has a monoester content of at least about 95%, wherein the ratio by weight of the first excipient to the second excipient is about 30:70, wherein the release rate is the release rate measured with USP Apparatus 2 (paddle) at 50 rpm in 500 mL of an aqueous medium at a temperature of 37° C.±0.5° C. at a pH of about 6.8. In some embodiments, the aqueous medium is an aqueous medium comprising sodium phosphate at a concentration of 0.05 M.

In some embodiments, the present invention is directed to a process for the preparation of a pharmaceutical composition comprising Compound 1. The process in one embodiment comprises:

mixing a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof with a first excipient as disclosed herein, a second excipient as disclosed herein, and optionally an additional pharmaceutically acceptable excipient, to form the pharmaceutical composition.

In some embodiments, the pharmaceutical compositions herein are in the form of a capsule. In some embodiments, the pharmaceutical compositions herein are in the form of a tablet.

In some embodiments of the pharmaceutical compositions and/or the processes disclosed herein, the mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient as disclosed herein, and a second excipient as disclosed herein, may be formed in any order. For example, in some embodiments, formation of the mixture of the compound and the two excipients may comprise mixing the two excipients to form an initial mixture. The mixing of the two excipients may comprise melting the two excipients together. The mixture may be subsequently mixed with the compound to form the mixture of the compound and the two excipients.

In some embodiments provided herein is a pharmaceutical composition prepared by the process comprising:

curing a mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain and (c) a second polyoxyethylene chain bonded to the poly(propylene oxide) chain, and the second excipient comprises an ester of a polyalcohol and a fatty acid, to form the composition.

In some embodiments provided herein is a process for preparing a pharmaceutical composition, the process comprising:

curing a mixture comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the polypropylene oxide) chain, and the second excipient comprises an ester of a polyalcohol and a fatty acid, to form the composition.

In some embodiments of the pharmaceutical composition and/or the process disclosed herein, curing a mixture is performed at a temperature of about 40° C. to about 70° C., such as about 45° C. to about 70° C., such as about 45° C. to about 65° C., such as about 45° C. to about 60° C., such as about 45° C. to about 55° C., such as about 50° C. to about 55° C., such as about 45° C., about 46° C., about 47° C., about 48° C., about 49° C., about 50° C., about 51° C., about 52° C., about 53° C., about 54° C., or about 55° C. The temperature at which curing the mixture is performed is also referred to as the curing temperature. The time for which curing the mixture at the curing temperature is performed is also referred to as the curing time. In some embodiments curing the mixture is performed for about 10 hours to about one week, in some embodiments curing the mixture is performed for about 10 hours to about 48 hours, such as for about 12 hours to about 36 hours, such as for about 16 hours to about 24 hours, such as for about 18 hours. In some embodiments curing the mixture is performed at a temperature of about 40° C. to about 70° C., such as about 50° C. to about 60° C., such as about 50° C. or about 55° C., for about 10 hours to about 48 hours, such as for about 12 hours to about 36 hours, such as for about 16 hours to about 24 hours, such as for about 18 hours. In some embodiments curing the mixture is performed at a temperature of about 50° C. for about 18 hours. In some embodiments curing the mixture is performed at a temperature of about 55° C. for about 36 hours. In some embodiments curing the mixture is performed at a temperature of about 50° C. to about 60° C., such as about 50° C. or about 55° C., for about 10 hours to about 48 hours, such as for about 12 hours to about 36 hours, such as for about 16 hours to about 24 hours, such as for about 18 hours. In some embodiments curing the mixture is performed at a temperature of about 50° C. for about 18 hours, in some embodiments curing the mixture is performed at a temperature of about 55° C. for about 36 hours.

In some embodiments of the pharmaceutical compositions disclosed herein, at least one of the first excipient and the second excipient has a melting point of about 45° C. to about 70° C. In some embodiments of the pharmaceutical compositions disclosed herein, at least one of the first excipient and the second excipient has a melting point of about 45° C. to about 65° C. In some embodiments of the pharmaceutical compositions disclosed herein, at least one of the first excipient and the second excipient has a melting point of about 45° C. to about 60° C. In some embodiments of the pharmaceutical compositions disclosed herein, at least one of the first excipient and the second excipient has a melting point of about 45° C. to about 55° C. In some embodiments of the pharmaceutical compositions disclosed herein, at least one of the first excipient and the second excipient has a melting point of about 50° C. to about 60° C. In some embodiments of the pharmaceutical compositions disclosed herein, at least one of the first excipient and the second excipient has a melting point of about 50° C. to about 55° C. In some embodiments of the pharmaceutical compositions disclosed herein, at least one of the first excipient and the second excipient has a melting point that is about 45° C., about 46° C., about 47° C., about 48° C., about 49° C., about 50° C., about 51° C. about 52° C., about 53° C., about 54° C., about 55° C., about 56° C., about 57° C., about 58° C., about 59° C., or about 60° C. In some embodiments, the first excipient and the second excipient each have a melting point that is independently about 45° C., about 46° C., about 47° C., about 48° C., about 49° C., about 50° C., about 51° C., about 52° C., about 53° C., about 54° C., or about 55° C.

In some embodiments of the pharmaceutical compositions disclosed herein, the composition is a cured composition. In some embodiments, the cured composition is a composition in which the compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, the first excipient, and the second excipient are cured together at a curing temperature as disclosed herein. In some embodiments, the cured composition is prepared by a process comprising curing the mixture as disclosed herein.

In some embodiments, curing the mixture results in a change in the Powder X-Ray Diffraction (PXRD) spectrum. In some embodiments, the pharmaceutical composition comprises the compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof; Poloxamer 188; and glycerol monostearate; wherein the composition exhibits peaks in the PXRD spectrum having the following 2☐ values: 19.7, 20.2°, 20.7°, 21.6°, 22.6°, 23.1° and 23.7°. In some embodiments, the composition exhibits peaks in the PXRD spectrum having the following 2☐ values: 19.7°, 20.2°, 20.7°, 22.6°, 23.1° and 23.7°. Each of the PXRD peak values reported above values may vary by ±0.2 2☐. In some embodiments of the composition having peaks in the PXRD spectrum as disclosed herein, the composition comprises glycerol monostearate having a monoester content of at least about 90%, such as at least about 95%. In some embodiments of the composition having peaks in the PXRD spectrum as disclosed herein, the composition comprises Poloxamer 188 and glycerol monostearate having a monoester content of at least about 90%, such as at least about 95%, in a ratio of Poloxamer 188:glycerol monostearate by weight that is about 70:30 to 10:90, such as 60:40 to about 20:80, such as about 50:50 to about 30:70, such as about 50:50, such as about 40:60, such as about 30:70.

In some embodiments, wherein the first excipient comprises a copolymer comprising (a) a first polyoxyethylene chain, (b) a poly(propylene oxide) chain bonded to the first polyoxyethylene chain; and (c) a second polyoxyethylene chain bonded to the poly(propylene oxide) chain, the first excipient consists essentially of the copolymer.

In some embodiments, wherein the first excipient comprises Poloxamer 188, the first excipient consists essentially of Poloxamer 188.

In some embodiments, wherein the first excipient comprises a copolymer as defined herein, the first excipient is the copolymer.

In some embodiments, wherein the first excipient comprises Poloxamer 188, the first excipient is Poloxamer 188.

In some embodiments, wherein the second excipient comprises glycerol monostearate, the second excipient consists essentially of glycerol monostearate. For example, in some embodiments wherein the second excipient comprises glycerol monostearate and has a monoester content of at least about 50%, the second excipient consists essentially of glycerol monostearate and has a monoester content of at least about 50%. For example, in some embodiments wherein the second excipient comprises glycerol monostearate and has a monoester content of at least about 60%, such as at least about 70%, such as at least about 75%, such as at least about 80%, such as at least about 90%, such as at least about 95%, such as at least about 96%, such as at least about 97%, such as at least about 98%, such as at least about 99%, the second excipient consists essentially of glycerol monostearate and has a monoester content of at least about 60%, such as at least about 70%, such as at least about 75%, such as at least about 80%, such as at least about 90%, such as at least about 95%, such as at least about 96%, such as at least about 97%, such as at least about 98%, such as at least about 99%.

In some embodiments, wherein the second excipient comprises glycerol monostearate, the second excipient is glycerol monostearate. For example, in some embodiments wherein the second excipient comprises glycerol monostearate and has a monoester content of at least about 50%, the second excipient is glycerol monostearate having a monoester content of at least about 50%. For example, in some embodiments wherein the second excipient comprises glycerol monostearate and has a monoester content of at least about 60%, such as at least about 70%, such as at least about 75%, such as at least about 80%, such as at least about 90%, such as at least about 95%, such as at least about 96%, such as at least about 97%, such as at least about 98%, such as at least about 99%, the second excipient is glycerol monostearate having a monoester content of at least about 60%, such as at least about 70%, such as at least about 75%, such as at least about 80%, such as at least about 90%, such as at least about 95%, such as at least about 96%, such as at least about 97%, such as at least about 98%, such as at least about 99%.

In some embodiments provided herein is a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, a first excipient, and a second excipient, wherein the first excipient comprises a copolymer comprising (a) a first polyoxyethylene chain; (b) a poly(propylene oxide) chain bonded to the first polyoxyethylene chain; and (c) a second polyoxyethylene chain bonded to the poly(propylene oxide) chain, and the second excipient comprises an ester of a polyalcohol and a fatty acid.

In some embodiments the present invention relates to a storage-stable pharmaceutical composition comprising compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof, as disclosed herein. "Storage-stable" as used herein means that the release rate of the compound is substantially the same after storage of the composition at 40° C. and 75% RH. In some embodiments of the storage-stable composition, the release rate of the compound is substantially the same after storage at 40° C. and 75% RH for at least about one month. In some embodiments of the storage-stable composition, the release rate of the compound is substantially the same after storage at 40° C. and 75% RH for at least about six months. In some embodiments of the storage-stable composition, the release rate of the compound is substantially the same after storage at 2.5° C. and 60% RH for at least about two years.

In some embodiments, the release rate of the compound after storage of the composition at 40° C. and 75% RH for at least about one month does not vary at any given dissolution time point by more than about 20% of the release rate of the compound prior to storage. In some embodiments, the release rate of the compound after storage of the composition at 40° C. and 75% RH for at least about one month does not vary at any given dissolution time point by more than about 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about one month does not vary at any given dissolution time point equal or greater than 2 hours by more than about 20% of the release rate of the compound prior to storage, wherein the release rate after storage and prior to storage are each measured with USP Apparatus 1 (baskets) at 100 rpm in 500 ml, of an aqueous medium at a pH of 6.8 at a temperature of 37° CT 0.5° C., wherein the aqueous medium comprises sodium phosphate at a concentration of 0.05 M. In some embodiments, the release rate of the compound after storage of the composition at 40° C. and 75% RH for at least about one month does not vary at any given dissolution time point equal or greater than 2 hours by more than about 10% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of composition at 40° C. and 75% RH for at least about one month does not vary at any given dissolution time point by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about one month does not vary at any given dissolution time point equal or greater than 2 hours by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M, in some embodiments, the release rate of the compound after storage of the composition at 40° C. and 75% RH for at least about one month does not vary at any given dissolution time point equal or greater than 2 hours by more than about 10% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M.

In some embodiments, the release rate of the compound after storage of the composition at 40° C. and 75% RH for at least about six months does not vary at any given dissolution time point by more than about 20% of die release rate of the compound prior to storage. In some embodiments, the release rate of the compound after storage of the composition at 40° C. and 75% RH for at least about six months does not vary at any given dissolution time point by more than about 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about six months does not vary at any given dissolution time point equal or greater than 2 hours by more than about 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° CT 0.5° C., wherein the aqueous medium comprises sodium phosphate at a concentration of 0.05 M. In some embodiments, the release rate of the compound after storage of the composition at 40° C. and 75% RH for at least about six months does not vary at any given dissolution time point equal or greater than 2 hours by more than about 10% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about six months does not vary at any given dissolution time point by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about six months does not vary at any given dissolution time point equal or greater than 2 hours by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 40° C. and 75% RH for at least about six months does not vary at any given dissolution time point equal or greater than 2 hours by more than about 10% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M.

In some embodiments, the release rate of the compound after storage of the composition at 25° C. and 60 RH for at least about two years does not vary at any given dissolution time point by more than about 20% of the release rate of the compound prior to storage. In some embodiments, the release rate of the compound after storage of the composition at 25° C. and 60 RH for at least about two years does not vary at any given dissolution time point by more than about 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 25° C. and 60 RH for at least about two years does not vary at any given dissolution time point equal or greater than 2 hours by more than about 10% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 25° C. and 60 RH for at least about two years does not vary at any given dissolution time point equal or greater than 2 hours by more than about 10% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 25° C. and 60 RH for at least about two years does not vary at any given dissolution time point by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 25° C. and 60 RH for at least about two years does not vary at any given dissolution time point equal or greater than 2 hours by more than about 20% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M. In some embodiments, the release rate of the compound after storage of the composition at 25° C. and 60 RH for at least about two years does not vary at any given dissolution time point equal or greater than 2 hours by more than about 10% of the release rate of the compound prior to storage, wherein the release rate after storage and prior to storage are each measured with USP Apparatus 2 (paddle) at 50 rpm in 500 mL of an aqueous medium at a pH of 6.8 at a temperature of 37° C.±0.5° C., wherein the aqueous medium comprises sodium phosphate at a concentration of 0.05 M.

In some embodiments, the release rates disclosed herein are release rates as determined by HPLC.

In some embodiments, provided herein is a composition which is any of the tablet formulations disclosed herein, such as the tablet formulations disclosed in Table 4.

In some embodiments provided herein is an ester of Compound 1. In some embodiments provided herein is 2-(((1r,4r)-(((4-chlorophenyl)(phenyl)carbamoyloxy)methyl)cyclohexyl)methoxy)acetic acid, ethanol ester. In some embodiments provided herein is 2-(((1r,4r)-(((4-chlorophenyl)(phenyl)carbamoyloxy)methyl)cyclohexyl)methoxy)acetic acid, ethylene glycol ester. In some embodiments provided herein is 2-(((1r,4r)-(((4-chlorophenyl)(phenyl)carbamoyloxy)methyl)cyclohexyl)methoxy)acetic acid, glycerol ester. In some embodiments provided herein is 2-(((1r,4r)-(((4-chlorophenyl)(phenyl)carbamoyloxy)methyl)cyclohexyl)methoxy)acetic acid, polyethylene glycol ester. In some embodiments provided herein is 2-(((1r,4r)-(((4-chlorophenyl)(phenyl)carbamoyloxy)methyl)cyclohexyl)methoxy)acetic acid, propylene glycol ester.

Figure 2:
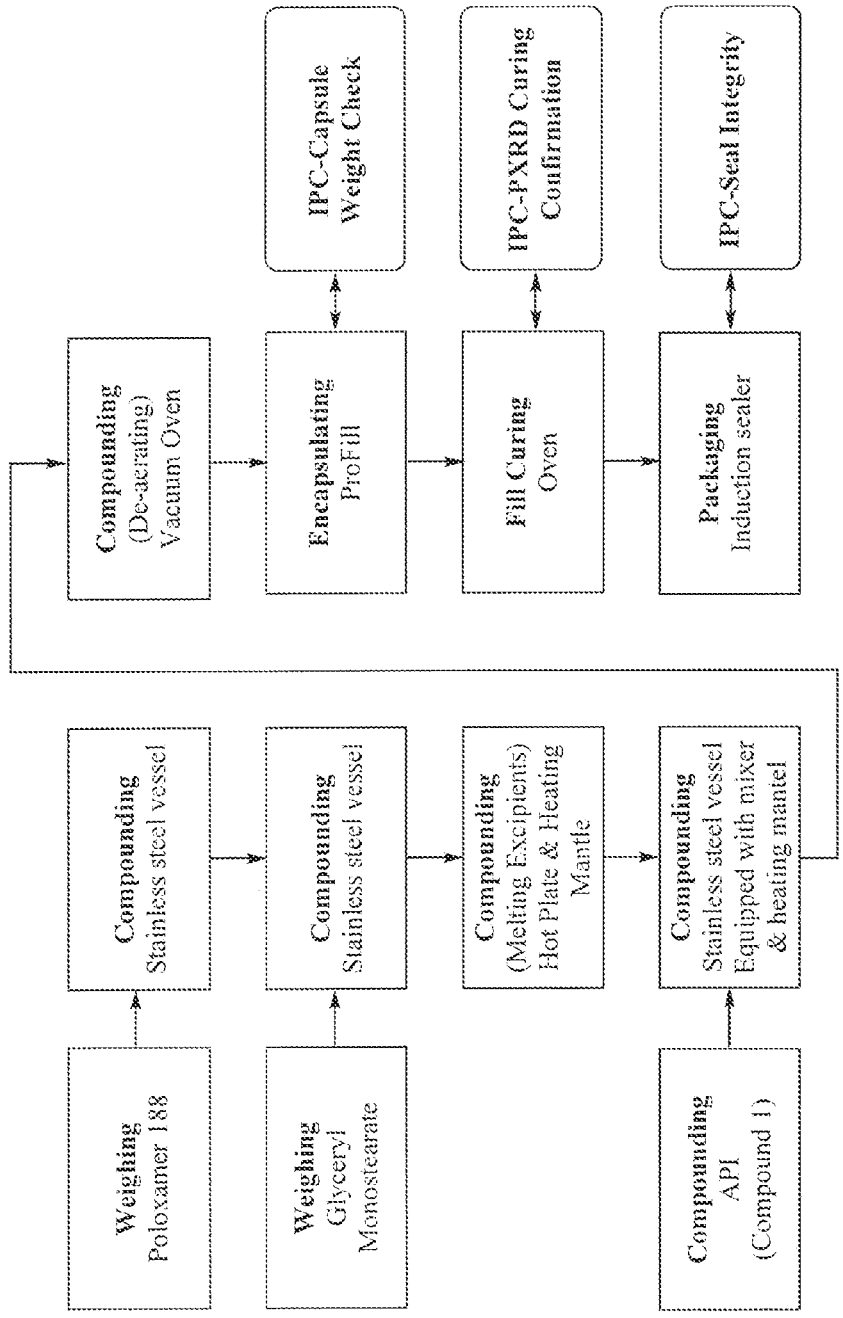
FIG. 2 shows a flowchart of an example of process for manufacturing a modified-release pharmaceutical composition comprising Compound 1 ("API" in the flowchart).

An example of a manufacturing process suitable for the pharmaceutical compositions disclosed herein is shown in FIG. 2.

A compound or composition provided herein can be formulated into pharmaceutical compositions using techniques well known to those in the art. Suitable pharmaceutically-acceptable carriers, outside those mentioned herein, are known in the art, for example, see Remington, *The Science and Practice of Pharmacy*, 20$^{th}$ Edition, 2000, Lippincott Williams & (Editors: Gennaro et al.).

Certain compounds described herein can be asymmetric (e.g, having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active stalling materials are known in the art, such as by resolution of racemic mixtures or by stereoselective synthesis.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, tnandelic acid, malic acid, lactic acid or the various optically active camphorsulfonic acids such as β-camphorsulfonic acid. Other resolving agents suitable for fractional crystallization methods include stereoisomerically pure forms of β-inethylbenzyl amine (e.g. S and R forms, or diastereomerically pure forms), 2-phenylglycinol, norephedrine, ephedrine, N-methylephedrine, cyclohcxylethylamine, 1,2-diaminocyclohexane, and the like.

Resolution of racemic mixtures can also be carried out by elution on a column packed with an optically active resolving agent (e.g, dinitrobenzoylphenylglycine). Suitable elution solvent composition can be determined by one skilled in the art.

Compounds described herein can also include all isotopes of atoms occurring in the intermediates or final compounds. Isotopes include those atoms having the same atomic number but different mass numbers. For example, isotopes of hydrogen include tritium and deuterium.

Compounds described herein can also include tautomeric forms, such as keto-enol tautomers. Tautomeric forms can be in equilibrium or sterically locked into one form by appropriate substitution.

It is appreciated that certain features disclosed herein, which are, for clarity, described in the context of separate embodiments, may also be provided in combination in a single embodiment. Conversely, various features which are, for brevity, described in the context of a single embodiment, may also be provided separately or in any suitable subcombination.

Indications and Methods of Treatment

The compositions disclosed herein are useful in the treatment of diseases and disorders related to modulation of PGI2 receptor activity, and in the amelioration of symptoms thereof. Accordingly, some embodiments of the present invention relate to a method of modulating the activity of a PGI2 receptor by contacting the receptor with a composition according to any of the embodiments described herein.

In some embodiments provided herein is a method of agonizing a PGI2 receptor by contacting the receptor with composition according to any of the embodiments described herein.

In some embodiments provided herein is a method for the treatment of a PGI2 receptor mediated disorder in an individual, comprising administering to the individual in need thereof, a composition according to any of the embodiments described herein.

In some embodiments provided herein is a composition according to any of the embodiments described herein, for use in a method of treatment of the human or animal body by therapy.

In some embodiments provided herein is a composition according to any of the embodiments described herein, for use in a method of modulating the activity of a PGI2 receptor.

In some embodiments provided herein is a composition according to any of the embodiments described herein, for use in a method of agonizing a PGI2 receptor.

In some embodiments provided herein is a composition according to any of the embodiments described herein, for use in a method of treatment of a PGI2 receptor mediated disorder.

The compositions disclosed herein are useful in the treatment of other diseases and disorders related to modulation of PGI2 receptor activity, and in the amelioration of symptoms thereof, without limitation, these include the following:

1. Pulmonary Arterial Hypertension (PAH)

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al, J. Am. Coll. Cardiol, 2004, 43:13S-24S.)

The pharmaceutical compositions of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary tutorial hypertension: idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HIV infection, PAH associated with drugs or toxins, or PAH associated with Other; and PAH associated with significant venous or capillary involvement.

Idiopathic PAH Refers to PAH of Undetermined Cause.

Familial PAH refers to PAH for which hereditary transmission is suspected or documented.

PAH associated with collagen vascular disease shall be understood to encompass PAH associated with scleroderma. PAH associated with CREST (calcinosis cutis, Raynaud's phenomenon, esophageal dysfunction, sclerodactyly, and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g, PAH associated with ingestion of fenfluramine or PAH associated with ingestion of dexfenfluramine), PAH associated with ingestion of certain toxic oils (e.g, PAH associated with ingestion of rapeseed oil), PAH associated with ingestion of pyrrolizidine alkaloids (e.g, PAH associated with ingestion of bush tea) and PAH associated with ingestion of monocrotaline.

PAH associated with Other shall be understood to encompass PAH associated with a thyroid disorder, PAH associated with glycogen storage disease, PAR associated with Gaucher disease, PAH associated with hereditary hemorrhagic telangiectasia, PAH associated with a hemoglobinopathy, PAH associated with a myeloproliferative disorder, and PAH associated with splenectomy.

PAH associated with significant venous or capillary involvement shall be understood to encompass PAH associated with pulmonary vena-occlusive disease (PVOD) and PAH associated with pulmonary capillary hemangiomatosis (PCH).

(See, e.g, Simonneau et al, J. Am. Coll. Cardiol, 2004, 43:5S-12S; McGoon et al, Chest, 2004, 126:14S-34S; Rabinovitch, Annu. Rev. Pathol, Mech, Dis, 2007, 2:369-399; McLaughlin et al, Circulation, 2006, 114:1417-1431; Strauss et al, Clin, Chest, Med, 2007, 28:127-142; Taichman et al, Clin. Chest. Med, 2007, 28:1-22.)

Evidence for the association of PAH with scleroderma and the beneficial effect of an agonist of the PGI2 receptor on PAH is given by Badesch et al. (Badesch et al, Ann. Intern. Med, 2000, 132:425-434). Evidence for the association of PAH with the collagen vascular diseases mixed connective tissue disease (MCTD), systemic lupus erythematosus (SLE), Sjögren's syndrome and CREST syndrome and the beneficial effect of an agonist of the PGI2 receptor on PAH is given by Humbert et al, (Eur. Respir. J, 1999, 13:1351-1356). Evidence for the association of PAH with CREST syndrome and the beneficial effect of an agonist of the PGI2 receptor on PAH is given by Miwa et al. (Int. Heart J, 2007, 48:417-422). Evidence for the association of PAH with SLE and the beneficial effect of an agonist of the PGI2 receptor on PAH is given by Robbins et al. (Chest, 2000, 117:14-18). Evidence for the association of PAH with HIV infection and the beneficial of an agonist of the PGI2 receptor on PAH is given by Aguilar et al. (Am. J. Respir. Crit. Care Med, 2000, 162:1846-1850). Evidence for the association of PAH with congenital heart defects (including ASD, VSD and patent ductus arteriosus) and the beneficial effect of an agonist of the PGI2 receptor on PAH is given by Rosenzweig et al. (Circulation, 1999, 99:1858-1865). Evidence for the association of PAH with fenfluramine and with dexfenfluramine, anorexigens, is given by Archer et al. (Am. J. Respir. Crit. Care Med, 1998, 1.58:1061-1067), Evidence for the association of PAH with hereditary hemorrhagic telangiectasia is given by McGoon et al. (Chest, 2004, 126:14-34), Evidence for the association of PAH with splenectomy is given by Hoeper et al. (Ann. Intern. Med, 1999, 130:506-509). Evidence for the association of PAH with portal hypertension and the beneficial effect of an agonist of the PGI2 receptor on PAH is given by Hoeper et al. (Eur. Respir. J, 2005, 25:502-508).

Symptoms of PAH include dyspnea, angina, syncope and edema (McLaughlin et al, Circulation, 2006, 114:1417-1431). The pharmaceutical compositions of the present invention disclosed herein are useful in the treatment of symptoms of PAH.

In some embodiments provided herein is a method for the treatment of pulmonary arterial hypertension (PAH) in an individual, comprising administering to the individual in need thereof, a composition according to any of the embodiments described herein.

In some embodiments provided herein is a method for the treatment of idiopathic PAH in an individual, comprising administering to the individual in need thereof, a composition according to any of the embodiments described herein.

In some embodiments provided herein is a method for the treatment of familial PAH in an individual, comprising administering to the individual in need thereof, a composition according to any of the embodiments described herein.

In some embodiments provided herein is a method for the treatment of PAH associated with a collagen vascular disease in an individual, comprising administering to the individual in need thereof, a composition according to any of the embodiments described herein.

In some embodiments provided herein is a method for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis in an individual, comprising administering to the individual in need thereof, a composition according to any of the embodiments described herein.

In some embodiments provided herein is a method for the treatment of PAH associated with a congenital heart disease in an individual, comprising administering to the individual in need thereof, a composition according to any of the embodiments described herein.

In some embodiments provided herein is a method for the treatment of PAH associated with a congenital heart disease selected from: atrial septic defect (ASD), ventricular septic defect (VSD) and patent ductus arteriosus in an individual, comprising administering to the individual in need thereof, a composition according to any of the embodiments described herein.

In some embodiments provided herein is a method for the treatment of PAH associated with portal hypertension in an individual, comprising administering to the individual in need thereof, a composition according to any of the embodiments described herein.

In some embodiments provided herein is a method for the treatment of PAH associated with HIV infection in an individual, comprising administering to the individual in need thereof, a composition according to any of the embodiments described herein.

In some embodiments provided herein is a method for the treatment of PAH associated with ingestion of a drug or toxin in an individual, comprising administering to the individual in need thereof, a composition according to any of the embodiments described herein.

In some embodiments provided herein is a method for the treatment of PAH associated with hereditary hemorrhagic telangiectasia in an individual, comprising administering to the individual in need thereof, a composition according to any of the embodiments described herein.

In some embodiments provided herein is a method for the treatment of PAH associated with splenectomy in an individual, comprising administering to the individual in need thereof, a composition according to any of the embodiments described herein.

In some embodiments provided herein is a method for the treatment of PAH associated with significant venous or capillary involvement in an individual, comprising administering to the individual in need thereof, a composition according to any of the embodiments described herein.

In some embodiments provided herein is a method for the treatment of PAH associated with pulmonary veno-occlusive disease (PVOD) in an individual, comprising administering to the individual in need thereof, a composition according to any of the embodiments described herein.

In some embodiments provided herein is a method for the treatment of PAH associated with pulmonary capillary hemangiomatosis (PCH) in an individual, comprising administering to the individual in need thereof, a composition according to any of the embodiments described herein.

In some embodiments provided herein is a composition according to any of the embodiments described herein, for use in a method of treatment of PAH.

In some embodiments provided herein is a composition according to any of the embodiments described herein, for use in a method of treatment of idiopathic PAH.

In some embodiments provided herein is a composition according to any of the embodiments described herein, for use in a method of treatment of familial PAH.

In some embodiments provided herein is a composition according to any of the embodiments described herein, for use in a method of treatment of PAH associated with a collagen vascular disease.

In some embodiments provided herein is a composition according to any of the embodiments described herein, for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

In some embodiments provided herein is a composition according to any of the embodiments described herein, for use in a method of treatment of PAH associated with a congenital heart disease.

In some embodiments provided herein is a composition according to any of the embodiments described herein, for use in a method of treatment of PAH associated with a congenital heart disease selected from: atrial septic defect (ASD), ventricular septic defect (VSD) and patent ductus arteriosus.

In some embodiments provided herein is a composition according to any of the embodiments described herein, for use in a method of treatment of PAH associated with portal hypertension.

In some embodiments provided herein is a composition according to any of the embodiments described herein, for use in a method of treatment of PAH associated with HIV infection.

In some embodiments provided herein is a composition according to any of the embodiments described herein, for use in a method of treatment of PAH associated with ingestion of a drug or toxin.

In some embodiments provided herein is a composition according to any of the embodiments described herein, for use in a method of treatment of PAH associated with hereditary hemorrhagic telangiectasia.

In some embodiments provided herein is a composition according to any of the embodiments described herein, for use in a method of treatment of PAH associated with splenectomy.

In some embodiments provided herein is a composition according to any of the embodiments described herein, for use in a method of treatment of PAH associated with significant venous or capillary involvement.

In some embodiments provided herein is a composition according to any of the embodiments described herein, for use in a method of treatment of PAH associated with pulmonary veno-occlusive disease (PVOD).

In some embodiments provided herein is a composition according to any of the embodiments described herein, for use in a method of treatment of PAH associated with pulmonary capillary hemangiomatosis (PCH).

2. Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction ("MI" or "heart attack"), the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart, in patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that a PGI2 receptor agonist will inhibit platelet aggregation and thus be a potential treatment as an antiplatelet therapy (see, e. g, Moncada et al, Lancet, 1977, 1:18-20). It has been shown that genetic deficiency of the PGI2 receptor in mice leads to an increased propensity towards thrombosis (Murata et al, Nature, 1997, 388:678-682).

PGI2 receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g, Fetalvero et al, Prostaglandins Other Lipid Mediat, 2007, 82:109-118; Arehart et al, Curr. Med. Chem, 2007, 14:2161-2169; Davi et al, N. Engl. J. Med, 2007, 357:2482-2494; Fetalvero et al, Am. J. Physiol. Heart. Circ. Physiol, 2006, 290:H1337-1-11346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans, 2007, 35:910-911; Arehart et al, Circ. Res, 2008. March 6 Epub ahead of print.)

PGI2 receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. PGI2 receptor agonists can also be used in antiplatelet therapies in combination with, for example, alpha-tocopherol (vitamin E), echistatin disintegrin) or, in states of hypercoagulability, heparin. (See, e.g, Chan, J. Nutr, 1998, 128:1593-1596; Mardla et al, Platelets, 2004, 15:319-324, Bernabei et al, Ann. Thorac. Surg, 1995, 59:149-153; Gainza et al, J. Nephrol, 2006, 19:(748-655.)

The PGI2 receptor agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein.

In further embodiments, the present invention provides methods for reducing risk of blood clot formation in an angioplasty or coronary bypass surgery patient, or a patient suffering from atrial fibrillation, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein at a time where such risk exists.

In some embodiments provided herein is a method for the treatment of platelet aggregation in an individual, comprising administering to the individual in need thereof, a composition according to any of the embodiments described herein.

In some embodiments provided herein is a method for the treatment of: coronary artery disease, myocardial infarction, transient ischemic attack, angina, stroke, ischemia-reperfusion injury, restenosis or atrial fibrillation in an individual, comprising administering to the individual in need thereof, a composition according to any of the embodiments described herein.

In some embodiments provided herein is a method for reducing the risk of blood clot formation in an angioplasty or coronary bypass surgery individual comprising administering to the individual in need thereof, a composition according to any of the embodiments described herein.

In some embodiments provided herein is a method for reducing the risk of blood clot formation in an individual suffering from atrial fibrillation comprising administering to the individual in need thereof, a composition according to any of the embodiments described herein.

In some embodiments provided herein is a composition according to any of the embodiments described herein, for use in a method of treatment of platelet aggregation.

In some embodiments provided herein is a composition according to any of the embodiments described herein, for use in a method of treatment of: coronary artery disease, myocardial infarction, transient ischemic attack, angina stroke, ischemia-reperfusion injury, restenosis or atrial fibrillation.

In some embodiments provided herein is a composition according to any of the embodiments described herein, for use in a method for the treatment of blood clot formation in an angioplasty or coronary bypass surgery individual.

In some embodiments provided herein is a composition according to any of the embodiments described herein, for use in a method for the treatment of blood clot formation in an individual suffering from atrial fibrillation.

3. Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the PGI2 receptor can confer protection from atherosclerosis, such as from atherothrombosis (Arehart et al, Curr. Med. Chem, 2007, 1.4:2161-2169; Stitham et al, Prostaglandins Other Lipid Mediat, 2007, 82:95-108; Fries et al, Hematology Am. Soc. Hematol, Educ, Program, 2005, 445-451; Egan et al, Science, 2004, 306:19544957, Kobayashi et al, J. Clin. Invest, 2004, 114:784-794; Arehart et al, Circ. Res, 2008, March 6 Epub ahead of print).

It has been shown that defective PGI2 receptor signaling appears to accelerate atherothrombosis in humans, i.e. that an agonist of the PGI2 receptor can confer protection from atherothrombosis in humans (Arehart et al, Circ. Res. 2008. March 6 Epub ahead of print).

The pharmaceutical compositions of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein. In further embodiments, methods are provided for treating a symptom of atherosclerosis in a patient in need of the treatment, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein.

In some embodiments provided herein is a method for the treatment of atherosclerosis in an individual, comprising administering to the individual in need thereof, a composition according to any of the embodiments described herein.

In some embodiments provided herein is a method for the treatment of atherothrombosis in an individual, comprising administering to the individual in need thereof, a composition according to any of the embodiments described herein.

In some embodiments provided herein is a composition according to any of the embodiments described herein, for use in a method of treatment of atherosclerosis.

In some embodiments provided herein is a composition according to any of the embodiments described herein, for use in a method of treatment of atherothrombosis.

4. Asthma

Asthma is a lymphocyte-mediated inflammatory airway disorder characterized by airway eosinophilia, increased mucus production by goblet cells, and structural remodeling of the airway wall. The prevalence of asthma has dramatically increased worldwide in recent decades, it has been shown that genetic deficiency of the PGI2 receptor in mice augments allergic airway inflammation (Takahashi et al, Br J Pharmacol, 2002, 137:315-322). It has been shown that an agonist of the PGI2 receptor can suppress not only the development of asthma when given during the sensitization phase, but also the cardinal features of experimental asthma when given during the challenge phase (idzko et al, J. Clin. Invest, 2007, 117:464-472; Nagao et al, Am. J. Respir. Cell Mol. Biol. 2003, 29:314-320), at least in part through markedly interfering with the function of antigen-presenting dendritic cells within the airways (Idzko et al, J. Clin. Invest, 2007, 117:464-472; Zhou et al, J. Immunol, 2007, 178:702-

710; Jaffar et al, J. Immunol, 2007, 179:6193-6203; Jozefowski et al, Int. Immunopharmacol, 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al, J. Exp. Med, 2005, 201:981-991). It has also been shown that an agonist of the PGI2 receptor can inhibit proinflammatory cytokine secretion by human alveolar macrophages (Raychaudhuri et al, J. Biol. Chem, 2002, 277:33344-33348). The pharmaceutical compositions of the present invention disclosed herein are useful in the treatment of asthma, and the treatment of the symptoms thereof. Accordingly, in some embodiments, the present invention provides methods for treating asthma in a patient in need of the treatment, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein. In further embodiments, methods are provided for treating a symptom of asthma in a patient in need of the treatment, comprising administering to the patient a pharmaceutical composition comprising a compound selected from 2-(((1r,4r)-(((4-chlorophenyl)(phenyl)carbamoyloxy)methyl)cyclohexyl)methoxy)acetic acid (Compound 1) and pharmaceutically acceptable salts, solvates, and hydrates thereof as disclosed herein. In some embodiments provided herein is a method for the treatment of asthma in an individual, comprising administering to the individual in need thereof, a composition according to any of the embodiments described herein.

In some embodiments provided herein is a method for the treatment of a symptom of asthma in an individual, comprising administering to the individual in need thereof, a composition according to any of the embodiments described herein.

In some embodiments provided herein is a composition according to any of the embodiments described herein, for use in a method of treatment of asthma.

In some embodiments provided herein is a composition according to any of the embodiments described herein, for use in a method of treatment of a symptom of asthma.

5. Diabetic-Related Pathologies

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al, Naunyn Schmiedebergs Arch. Pharmacol, 2003, 367:607-614). Agonists of the PGI2 receptor promote vasodilation and inhibit platelet aggregation. Improving microvascular blood flow is able to benefit diabetic complications (Cameron. Diabetologia, 2001, 44:1973-1988).

It has been shown that an agonist of the PGI2 receptor can prevent and reverse motor and sensory peripheral nerve conduction abnormalities in streptozotocin-diabetic rats (Cotter et al, Naunyn Schmiedebergs Arch. Pharmacol, 1993, 347:534-540). Further evidence for the beneficial effect of an agonist of the PGI2 receptor in the treatment of diabetic peripheral neuropathy is given by Hotta et al. (Diabetes, 1996, 45:361-366), Ueno et al. (Jpn. J. Pharmacol, 1996, 70:177-182), Ueno et al. (Life Sci, 1996, 59:PL105-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J, 2003, 17:779-781). Evidence for the beneficial effect of an agonist of the PGI2 receptor in the treatment of diabetic nephropathy is given by Owada et al, (Nephron, 2002, 92:788-796) and Yamashita et al. (Diabetes Res, Clin, Pract, 2002, 57:149-161), Evidence for the beneficial effect of an agonist of the PGI2 receptor in the treatment of diabetic retinopathy is given by Yamagishi et al. (Mol. Med, 2002, 8:546-550), Burnette et al. (Exp. Eye Res, 2006, 83:1359-1365), and Hotta et al. (Diabetes, 1996, 45:361-366). It has been shown that an agonist of the PGI2 receptor can reduce increased tumor necrosis factor-α (INF-α) levels in diabetic patients, implying that an agonist of the PGI2 receptor may contribute to the prevention of progression in diabetic complications (Fujiwara et al, Exp. Clin. Endocrinol. Diabetes, 2004, 112:390-394).

In some embodiments provided herein is a method for the treatment of a diabetic-related disorder in an individual, comprising administering to the individual in need thereof, a composition according to any of the embodiments described herein.

In some embodiments provided herein is a method for the treatment of diabetic peripheral neuropathy in an individual, comprising administering to the individual in need thereof, a composition according to any of the embodiments described herein.

In some embodiments provided herein is a method for the treatment of diabetic nephropathy in an individual, comprising administering to the individual in need thereof, a composition according to any of the embodiments described herein.

In some embodiments provided herein is a method for the treatment of diabetic retinopathy in an individual, comprising administering to the individual in need thereof a composition according to any of the embodiments described herein.

In some embodiments provided herein is a composition according to any of the embodiments described herein, for use in a method of treatment of a diabetic-related disorder.

In some embodiments provided herein is a composition according to any of the embodiments described herein, for use in a method of treatment of diabetic peripheral neuropathy.

In some embodiments provided herein is a composition according to any of the embodiments described herein, for use in a method of treatment of diabetic nephropathy.

In some embodiments provided herein is a composition according to any of the embodiments described herein, for use in a method of treatment of diabetic retinopathy.

6. Glaucoma

Evidence that topical administration of an agonist of the PGI2 receptor can result in a decrease in intraocular pressure (IOP) in rabbits and dogs and thereby have beneficial effect in the treatment of glaucoma is given by Hoyng et al. (Hoyng et al. Invest. Ophthalmol. Vis. Sci, 1987, 28:470-476).

In some embodiments provided herein is a method for the treatment of glaucoma or other disease of the eye with abnormal intraocular pressure in an individual, comprising administering to the individual in need thereof, a composition according to any of the embodiments described herein.

In some embodiments provided herein is a composition according to any of the embodiments described herein, for use in a method of treatment of glaucoma or other disease of the eye with abnormal intraocular pressure.

7. Hypertension

Agonists of the PGI2 receptor have been shown to have activity for regulation of vascular tone, for vasodilation, and for amelioration of pulmonary hypertension (see, e.g, Strauss et al, Clin Chest Med, 2007, 28:127-142; Driscoll et al, Expert Opin. Pharmacother, 2008, 9:65-81). Evidence for a beneficial effect of an agonist of the PGI2 receptor in the treatment of hypertension is given by Yamada et al. (Peptides, 2008, 29:412-418). Evidence that an agonist of the PGI2 receptor can protect against cerebral ischemia is given by Dogan et al, (Gun. Pharmacol, 1996, 27:1163-1166) and Fang et al. (J. Cereb. Blood Flow Metab, 2006, 26:491-501).

In some embodiments provided herein is a method for the treatment of hypertension in an individual, comprising administering to the individual in need thereof, a composition according to any of the embodiments described herein.

In some embodiments provided herein is a method for the treatment of hypertension intended to confer protection against cerebral ischemia in an individual, comprising administering to the individual in need thereof, a composition according to any of the embodiments described herein.

In some embodiments provided herein is a composition according to any of the embodiments described herein, for use in a method of treatment of hypertension.

In some embodiments provided herein is a composition according to any of the embodiments described herein, for use in a method of treatment of hypertension intended to confer protection against cerebral ischemia.

8. Anti-Inflammation Therapies

Anti-inflammation agents are prescribed for a variety of conditions. For example, in an inflammatory disease they are used to interfere with and thereby reduce an underlying deleterious There is evidence that a PGI2 receptor agonist can inhibit inflammation and thus be a potential treatment as an anti-inflammation therapy. It has been shown that an agonist of the PGI2 receptor can inhibit pro-inflammatory cytokine and chemokine (interleukin-12 (IL-12), tumor necrosis factor-α (TNF-α), IL-1α, IL-6, macrophage inflamatory protein-1 alpha (MIP-1α), monocyte chemoattractant protein-1 (MCP-1)) production and T cell stimulatory function of dendritic cells (Jozefowski et al, Int. Immunopharmacol, 2003, 865-878; Zhou et al, J. Immunol, 2007, 178:702-710; Nagao et al, Am. J. Respir. Cell Mol. Biol. 2003, 29:314-320; Idzko et al, J. Clin. Invest, 2007, 117: 464-472). It has been shown that an agonist of the PGI2 receptor can inhibit pro-inflammatory cytokine (TNF-α, IL-1β, IL-6, granulocyte macrophage stimulating factor (GM-CSF)) production by macrophages (Raychaudhuri et al, J. Biol. Chem, 2002, 277:33344-33348; Czeslick et al, Eur. J. Clin. Invest, 2003, 33:1013-1017; Di Renzo et al, Prostaglandin Leukot. Essent. Fatty Acids, 2005, 73:405-410; Shinomiya et al, Biochem. Pharmacol, 2001, 61:1153-1160). It has been shown that an agonist of the PGI2 receptor can stimulate anti-inflammatory cytokine (IL-10) production by dendritic cells (Jozefowski et al, Int. Immunopharmacol, 2003, 865-878; Zhou et al, J. Immunol, 2007, 178:702-710), it has been shown that an agonist of the PGI2 receptor can stimulate anti-inflammatory cytokine (IL-10) production by macrophages (Shinomiya et al, Biochem. Pharmacol, 2001, 61:1153-1160). It has been shown that an agonist of the PGI2 receptor can inhibit a chemokine (CCL17)-induced chemotaxis of leukocytes ($CD4^+$ Th2 T cells) (Jaffar et al, J. Immunol, 2007, 179:6193-6203). It has been shown that an agonist of the PGI2 receptor can confer protection from atherosclerosis, such as from atherothrombosis (Arehart et al. Curr. Med. Chem, 2007, 14:2161-2169; Stitham at al Prostaglandins Other Lipid Mediat, 2007, 82:95-108; Fries et at, Hematology Am. Soc. Hematol, Educ. Program, 2005, 445451; Egan et al. Science, 2004, 306:1954-1957; Kobayashi et al. J. Clin. Invest. 2004, 114:784-794; Arehart et al. Circ. Res, 2008, March 6 Epub ahead of print). It has been shown that an agonist of the PGI2 receptor can attenuate asthma (Idzko et al, J. Clin. Invest, 2007, 117:464-472; Jaffar at al, Immunol. 2007, 179:6193-6203; Nagao et al, Am. J. Respir. Cell. Mol. Biol, 2003, 29:314-320). It has been shown that an agonist of the PGI2 receptor can decrease INF-α production in type 2 diabetes patients (Fujiwara et al. Exp. Clin. Endocrinol. Diabetes, 2004, 112:390-394; Goya et al, Metabolism, 2003, 52:192-198). It has been shown that an agonist of the PGI2 receptor can inhibit ischemia-reperfusion injury (Xiao et al, Circulation, 2001, 104:2210-2215). It has been shown that an agonist of the PGI2 receptor can inhibit restenosis (Cheng et al, Science, 2002, 296:539-541). It has been shown that an agonist of the PGI2 receptor can attenuate pulmonary vascular injury and shock in a rat model of septic shock (Harada et al. Shock, 2008, February 21 Epub ahead of print). It has been shown that an agonist of the PGI2 receptor can reduce the serum levels of TNF-α in vivo in patients with rheumatoid arthritis, and this is associated with improvement in the clinical course of the disease (Gao et al, Rheumatol. Int, 2002, 22:45-51; Boehme et al, Rheumatol. Int, 2006, 26:340-347).

The pharmaceutical compositions of the present invention disclosed herein provide beneficial reduction of inflammation. The pharmaceutical compositions of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a pharmaceutical composition as disclosed herein. In some embodiments, the present invention provides methods for decreasing IL-12, TNF-α, IL-1α, IL-1β, MIP-1α or MCP-1 production in a patient in need thereof, comprising administering to the patient a pharmaceutical composition as disclosed herein. In some embodiments, the present invention provides methods for decreasing TNF-α production in a patient in need thereof, comprising administering to the patient a pharmaceutical composition as disclosed herein. In some embodiments, the present invention provides methods for increasing IL-10 production in a patient in need thereof, comprising administering to the patient a pharmaceutical composition as disclosed herein. In some embodiments, the present invention provides methods for reducing a deleterious inflammatory response associated with an inflammatory disease in a patient in need thereof, comprising administering to the patient a pharmaceutical composition as disclosed herein. In some embodiments, the present invention provides methods for treating an inflammatory disease or a symptom thereof in a patient in need of the treatment comprising administering to the patient a pharmaceutical composition as disclosed herein. In some embodiments, the present invention provides methods for treating an inflammatory disease or a symptom thereof in a patient in need of the treatment comprising administering to the patient a pharmaceutical composition as disclosed herein. In some embodiments, the present invention provides methods for treating an inflammatory disease or a symptom thereof in a patient in need of the treatment comprising administering to the patient a pharmaceutical composition as disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

In some embodiments provided herein is a method for the treatment of inflammation in an individual, comprising administering to the individual in need thereof, a composition according to any of the embodiments described herein.

In some embodiments provided herein is a method for the treatment of an inflammatory disease in an individual, comprising administering to the individual in need thereof, a composition according to any of the embodiments described herein.

In some embodiments provided herein is a method for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma in an individual, comprising administering to the individual in need thereof, a composition according to any of the embodiments described herein.

In some embodiments provided herein is a composition according to any of the embodiments described herein, for use in a method of treatment of inflammation.

In some embodiments provided herein is a composition according to any of the embodiments described herein, for use in a method of treatment of an inflammatory disease.

In some embodiments provided herein is a composition according to any of the embodiments described herein, for use in a method of treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

The dose when using the compositions of the present invention can vary within wide limits and as is customary and is known to the physician, it is to be tailored to the individual conditions in each individual case, it depends, for example, on the nature and severity of the illness to be treated, on the condition of the patient, on the compound employed or on whether an acute or chronic disease state is treated or prophylaxis conducted or on whether further active compounds are administered in addition to the pharmaceutical composition as disclosed herein. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician, in general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g, into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily close indicated.

The pharmaceutical preparations are preferably in unit dosage forms. In such form, the preparation is subdivided into unit doses containing appropriate quantities of the active component. The unit dosage form can be a packaged preparation, the package containing discrete quantities of preparation.

The compositions disclosed herein are not intended for use in humans only, but in non-human mammals as well. Recent advances in the area of animal health-care mandate that consideration be given for the use of active agents, such as Compound 1 for the treatment of a PGI2-receptor associated disease or disorder in companionship animals (e.g, cats, dogs, etc.) and in livestock animals (e.g, horses, cows, etc.). Those of ordinary skill in the art are readily credited with understanding the utility of such compounds in such settings.

Combination Therapy

In some embodiments, the at least one compound according to any of the compound embodiments disclosed herein is administered in combination with at least one known pharmaceutical agent. Administration of the at least one compound and the at least one known pharmaceutical agent can occur simultaneously or sequentially by the same or different routes of administration.

In some embodiments, the at least one known pharmaceutical agent is administered to the patient prior to initiation of the administration of the at least one compound. In some embodiments, the at least one known pharmaceutical agent is administered for at least one week, or at least two weeks, or at least three weeks, or at least one month, or at least two months, or at least three months prior to initiation of the administration of the at least one compound.

The suitability of a particular route of administration employed for a particular known pharmaceutical agent will depend on the known pharmaceutical agent itself (e.g., whether it can be administered orally or topically without decomposition prior to entering the blood stream) and the subject being treated. Particular routes of administration for the known pharmaceutical agents or ingredients are known to those of ordinary skill in the art.

The amount of known pharmaceutical agent administered can be determined based on the specific agent used, the subject being treated, the severity and stage of disease and the amount(s) of the at least one compound and any optional additional known pharmaceutical agents concurrently administered to the patient. The at least one known pharmaceutical agent, when employed in combination with at least one compound according to any of the compounds embodiment disclosed herein, may be used, for example, in those amounts indicated in the Physicians' Desk Reference (PDR) or as otherwise determined by one of ordinary skill in the art.

In some embodiments, the dose of the at least one known pharmaceutical agent is reduced when used in combination with the at least one compound according to any of the compound embodiments disclosed herein. In some embodiments, the dose is not reduced.

Some embodiments of the present invention include a method of producing a pharmaceutical composition for "combination therapy" comprising admixing at least one compound according to any of the compound embodiments disclosed herein together with at least one known pharmaceutical agent as described herein and a pharmaceutically acceptable carrier.

In some embodiments, the at least one known pharmaceutical agent is an oral disease-specific PAH therapy. In some embodiments, the oral disease-specific PAH therapy is chosen from an ERA and/or an agent acting on the NO pathway including the following: a PDE-5 inhibitor and a sGC stimulator.

In some embodiments, the subject had been receiving a stable dose of oral disease-specific PAH therapy for least three months prior to initiation of administration of the at least one compound described herein.

In some embodiments, the at least one known pharmaceutical agent is chosen from vasodilators (including calcium channel blockers), digoxin, spironolactone, and L-arginine supplementation. In some embodiments, the subject had been receiving a stable dose of the at least one known pharmaceutical agent for least one month prior to initiation of administration of the at least one compound described herein. In some embodiments, the dose of the spironolactone and/or the digoxin were held or reduced.

In some embodiments, the at least one known pharmaceutical is a diuretic.

In some embodiments, the at least one known pharmaceutical agent is a PDE-5 inhibitor.

In some embodiments, the at least one known pharmaceutical agent is for supportive therapy, such as diuretics, antihypertensives, antithrombotic agents, beta blocking agents, and cardiac medications.

In some embodiments, the at least one known pharmaceutical agent is a PAH disease-specific medication chosen from ambrisentan, bosentan, macitentan, riociguat, sildenafil sildenafil citrate, and tadalafil.

In some embodiments, the at least one known pharmaceutical agent is an antithrombotic agent chosen from acenocournarol, acetylsalicylic acid, warfarin, enoxaparin sodium, apixaban, dalteparin, heparin sodium, nadroparin calcium, sulodexide, and ticagrelor.

In some embodiments, the at least one known pharmaceutical agent is an agent acting on the renin-angiotensin system chosen from enalapril, lisinopril, valsartan, hyzaar, perindopril arginine, ramipril, and zestoretic.

In some embodiments, the at least one known pharmaceutical agent is a beta blocking agent chosen from bisoprolol, nebivolol, bisoprolol fumarate, metoprolol, metoprolol succinate, and nadolol.

In some embodiments, the at least one known pharmaceutical agent is a calcium channel blocker chosen from nifedipine, felodipine, verapamil, amlodipine, amlodipine hesitate, and diltiazem.

In some embodiments, the at least one known pharmaceutical agent is an agent for cardiac therapy chosen from digoxin, ivabradine, norepinephrine, amiodarone, amiodarone hydrochloride, atropine, dobutamine, epinephrine, trimetazidine, and trimetazidine hydrochloride.

In some embodiments, the at least one compound according to any of the compound embodiments disclosed herein is not administered in combination with intravenous inotropes.

In some embodiments, the at least one compound according to any of the compound embodiments disclosed herein is not administered in combination the chronic administration (such as >30 days) of a prostacyclin or prostacyclin analogue.

In some embodiments, the at least one known pharmaceutical agent is not a cAMP-elevating agent, or a cGMP-elevating agent, such as a soluble guanylate cyclase (sGC) stimulators such as riociguat.

In some embodiments, the at least one known pharmaceutical agent is not riociguat, vericiguat, ataciguat, nelociguat, lificiguat, IW-1701, IW-1973, IWP-051, IWP-121, IWP-427, IWP-953, BAY-60-2770, A-344905, A-350619, A-778935, BI-684067, BI-703704, BAY-41-2272, or BAY-41-8543.

In some embodiments, the at least one known pharmaceutical agent is not a prostanoid, such as treprostinil or iloprost.

In some embodiments, the at least one known pharmaceutical agent is not a prostacyclin receptor agonist.

Hydrates and Solvates

The term "hydrate" as used herein means a compound or a salt thereof, that further includes a stoichiometric or non-stoichiometric amount of water bound by non-covalent intermolecular forces. The term "solvate" as used herein means a compound or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to salts described herein, it embraces pharmaceutically acceptable solvates and/or hydrates of such salts.

It will be apparent to those skilled in the art that the compositions described herein may comprise, as the active component, either a compound described herein or a pharmaceutically acceptable salt or as a pharmaceutically acceptable solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc, New York, 1999. Accordingly, one aspect of the present invention is directed to methods of administering pharmaceutical composition comprising hydrates and solvates of compounds described herein and/or their pharmaceutical acceptable salts, that can be isolated and characterized by methods known in the art, such as, thermogravimetric analysis (TGA). TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, DE), Avantium Technologies (Amsterdam) and Aptuit (Greenwich. CT).

Crystalline Forms

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily and may be thermodynamically favored over anhydrous polymorphs.

By way of example, Stahly recently published a polymorph screen of 245 compounds consisting of a "wide variety of structural types" that revealed about 90% of the compounds exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates (G. P. Stahly, Crystal Growth & Design (2007), 7(6), 1007-1026).

Crystalline forms can be identified by their unique solid state signatures with respect to, for example, differential scanning calorimetry (DSC), X-ray powder diffraction (PXRD), and other solid state methods. Further characterization with respect to water or solvent content of the crystalline forms of the present invention can be gauged by any of the following methods for example, thermogravimetric analysis (TGA). DSC and the like. For DSC, it is known that the temperatures corresponding to thermal events observed will depend upon sample purity, the rate of temperature change, as well as sample preparation technique and the particular instrument employed.

A crystalline form of Compound 1 and of certain salts thereof is disclosed in WO 2009/117095 (incorporated by reference herein in its entirety). In some embodiments, the pharmaceutical compositions disclosed herein comprise Compound 1 in a crystalline form having a PXRD spectrum with 2☐ peak values as disclosed in WO 2009/117095.

PXRD may also be used to analyze the effect of curing on the pharmaceutical compositions disclosed herein. PXRD spectra disclosed herein were obtained with a Phillips X'Pert PRO MPD powder diffractometer using Cu-Kα radiation. For PXRD purposes, the composition is reduced to powder using a razor blade. The powder was then loaded onto a sample plate and smoothed flat using weighing paper and a spatula.

Figure 7A:
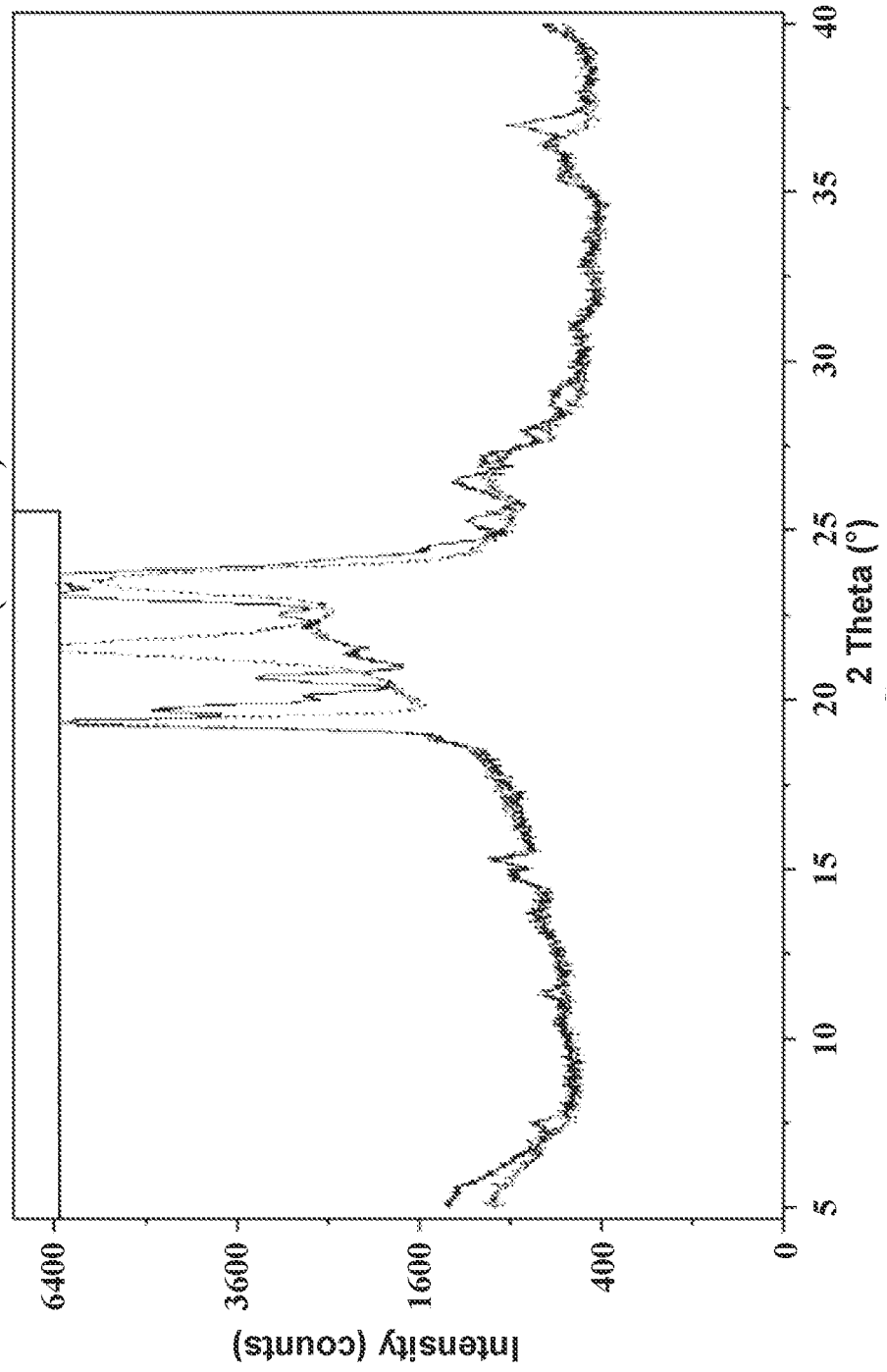
FIG. 7A shows a comparison of Powder X-Ray Diffraction (PXRD) spectra of a capsule containing Poloxamer 188 and food grade GMS in a 50:50 ratio by weight (i) before curing, and (ii) after curing at 50° C. for 18 hours. The solid line in FIG. 7A relates to 0.04 mg of Compound 1 in 50:50 Poloxamer-GMS, 18 hrs, 50° C.; and the dashed line in FIG. 7A relates to 0.04 mg of Compound 1 in 50:50 Poloxamer-GMS, T=0.

FIG. 7a discloses a Powder X-Ray Diffraction spectra of a capsule comprising Poloxamer 188 and food grade GMS in a 50:50 ratio by weight (i) before curing, and (ii) after curing at 50° C. for 18 hours. Prior to curing, the Poloxamer 188 PXRD spectrum includes peaks at 2☐ values of about 19.3° and about 23.5°, while the food grade GMS PXRD spectrum includes a broad peak at a 2☐ value of about 21.6°. The PXRD spectrum of the pharmaceutical composition after curing for 18 hours shows (a) a 21.6°2 ☐ peak of reduced intensity relative to prior to curing, and (b) peaks at 2☐ values of 19.7°, 20.2°, 20.7°, 22.6°, 23.1° and 23.7° peaks. Each of the PXRD peak values reported above values may vary by ±0.2 2☐.

Figure 7B:
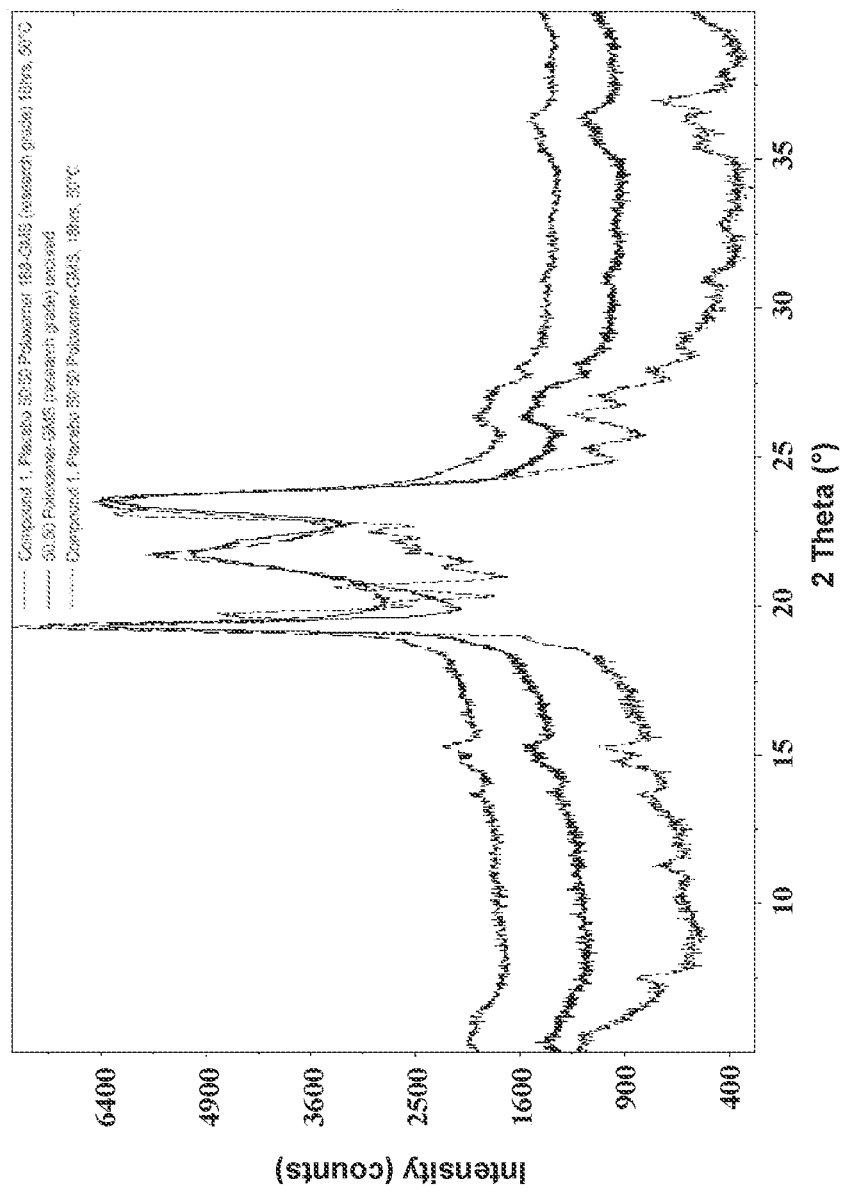
FIG. 7B shows a Powder X-Ray Diffraction spectrum of a capsule comprising Poloxamer 188 and research grade GMS in a 50:50 ratio by weight (i) before curing, and (ii) after curing at 50° C. for 18 hours. Powder X-Ray Diffraction spectrum of a capsule comprising Poloxamer 188 and research grade GMS in a 50:50 ratio by weight (i) before curing, and (ii) after curing at 50° C. for 18 hours. Also shown for comparison is (iii) a PXRD spectrum of a capsule comprising Poloxamer 188 and food grade GMS in a 50:50 ratio by weight after curing at 50° C. for 18 hours.

FIG. 7b shows a Powder X-Ray Diffraction spectra of a capsule comprising Poloxamer 188 and research grade GMS in a 50:50 ratio by weight (1) before curing, and (ii) after curing at 50° C. for 18 hours. The 2☐ values of the PXRD peaks of the pharmaceutical composition after curing for 18 hours do not substantially differ from the 2☐ values of the Poloxamer 188 PXRD and of the research grade GMS PXRD prior to curing.

Under certain conditions, curing is partial, as indicated by the resulting PXRD, FIG. 7c shows three Powder X-Ray Diffraction spectra of capsules comprising Poloxamer 188 and research grade GMS in a 50:50 ratio by weight (i) before curing ("uncured"), (ii) after partial curing at 47.5° C. for 10 hours ("partially cured"), and (iii) after curing at 50° C. for 18 hours ("fully cured"). Referring to (ii), following partial curing, peaks at 2☐ values of 20.2°, 20.7° appear. A peak at a 2☐ value of 21.6°, also present in (i), is still visible in (ii).

Other Utilities

Other uses of the disclosed compositions will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

The pharmaceutical compositions disclosed herein and their preparation are further illustrated by the following examples. The following examples are provided to further define the invention without, however, limiting the invention to the particulars of these examples. The compounds described herein, supra and infra, are named according to the CS Chem Draw Ultra Version 7.0.1, AutoNom version 2.2, CS ChemDraw Ultra Version 9.0.7, or CS ChemDraw Ultra Version 12.0. In certain instances, common names are used and it is understood that these common names would be recognized by those skilled in the art.

Preparation of Liquid-Filled Hard-Gelatin Capsules.

In selecting excipients for Compound 1, several factors were taken into consideration with the ultimate goal of choosing excipients suitable for later-stage formulation development. Criteria based on solubility, compatibility, viscosity, and stability are outlined below. In addition, selected excipients should preferably have proven safety profiles and USP/NF monographs to allow for compendial release testing. Furthermore, these excipients should have precedence in being commercially used in other products and be produced in quantities sufficient for late-stage clinical trials and commercialization.

Comparative Example 1

Immediate-Release Formulation

Immediate-release formulations may be prepared, for example, in a manner analogous to that described in FIG. 2. A suitable excipient for immediate-release (IR) formulations is Kolliphor® RH40. An immediate-release (IR) formulation containing Kolliphor® RH40 in which Compound 1 is present in the amounts of 0.01 mg, 0.02 mg, 0.03 mg, 0.04 mg, or 0.1 mg is described in the following Table 1:

TABLE 1

| Component | Grade | Function | 0.01 mg | 0.02 mg | 0.03 mg | 0.04 mg | 0.1 mg |
|---|---|---|---|---|---|---|---|
| | | | mg/capsule | | | | |
| Compound 1 | | Drug substance | 0.01 | 0.02 | 0.03 | 0.04 | 0.10 |
| Polyoxyl 40 hydrogenated castor oil (Kolliphor ® RH40) | USP/NF | Excipient | 148.46 | 148.45 | 148.44 | 148.43 | 148.37 |
| Butylated hydroxytoluene (BHT) | USP/NF | Antioxidant | 0.03 | 0.03 | 0.03 | 0.03 | 0.03 |
| Colloidal silicon dioxide | USP/NF | Thickening agent | 1.50 | 1.50 | 1.50 | 1.50 | 1.50 |
| Fill weight | | | 150.00 | 150.00 | 150.00 | 150.00 | 150.00 |
| Hard-gelatin capsule[a] (white, Licaps ®) | Capsugel ® internal | Capsule shell | 38.00 | 38.00 | 38.00 | 38.00 | 38.00 |
| Total capsule target weight[b] | | | 188.00 | 188.00 | 188.00 | 188.00 | 188.00 |

[a]Approximate weight. Based on capsule specification.
[b]Theoretical total weight calculated by combining fill and empty capsule weights together.

FIG. 1 shows a release profile for an immediate release capsule having 0.5 mg of Compound 1; 0.03 mg BHT; 1.50 mg silicon dioxide; and 147.97 mg Kolliphor® RH-140.

Example 1

Modified-Release Compositions—Capsules

A desirable feature of a modified-release composition is a stable release profile, i.e, in which the release rate of the drug does not vary substantially over time. For example, a desirable feature is a release rate that does not vary substantially over a time period during which the drug is in storage. Accordingly, various combinations of excipients were tested with the goal of obtaining a composition having a release rate of Compound 1 that would be stable over time.

An example of a suitable composition is a composition in the form of a capsule. An example of hard-gelatin capsule is shown in Table 2.

TABLE 2

| Size 2 Licaps ® Specifications | |
|---|---|
| Weight (mg) | 61 ± 4 |
| Capacity (mL) | 0.33 |
| Length of capsule body (mm) | 15.27 ± 0.46 |
| Length of capsule cap (mm) | 8.94 ± 0.46 |
| External diameter of capsule body (mm) | 6.07 |
| External diameter of capsule cap (mm) | 6.35 |
| Overall closed length (mm) | 18.0 ± 0.3 |

Example 2

Preparation of Capsules Containing Modified Release Compositions Containing Gelucire® 50/13

Gelucire® 50/13, having a melting point of about 50° C. and hydrophilic-lipophilic balance of 13 (also known as Stearoyl polyoxyl-32 glycerides, hydrogenated palm oil PEG-32 esters, PEG glyceryl stearate, and stearoyl polyoxylglycerides) is an excipient prepared via the reaction of hydrogenated palm oil with PEG 1500. Its composition is about 20% mono-, di- & tri-glycerides, about 72% mono- and di-fatty acid esters of PEG 1500, and about 8% PEG 1500, wherein PEG 1500 as used herein refers to the following:

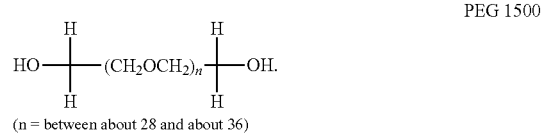

PEG 1500
(n = between about 28 and about 36)

Modified-release compositions containing Gelucire® 50/13 that were tested were analogous to the one described in Table 1 of comparative Example 1, except that in this Example 2, (a) Gelucire® 50/13 was used, in increasing amounts, in addition to Kolliphor® RH40, and (b) colloidal silicon dioxide was not required as a thickening agent in the compositions of this Example. Colloidal silicon dioxide was present at a level of about 1% w/w in the composition of Table 1 to minimize the potential of capsule leakage for the Kolliphor® 81140 capsules. Since Gelucire® 50/13 is a wax at ambient temperatures, the use of colloidal silicon dioxide was not required in the modified-release compositions of this Example 2.

Figure 3:
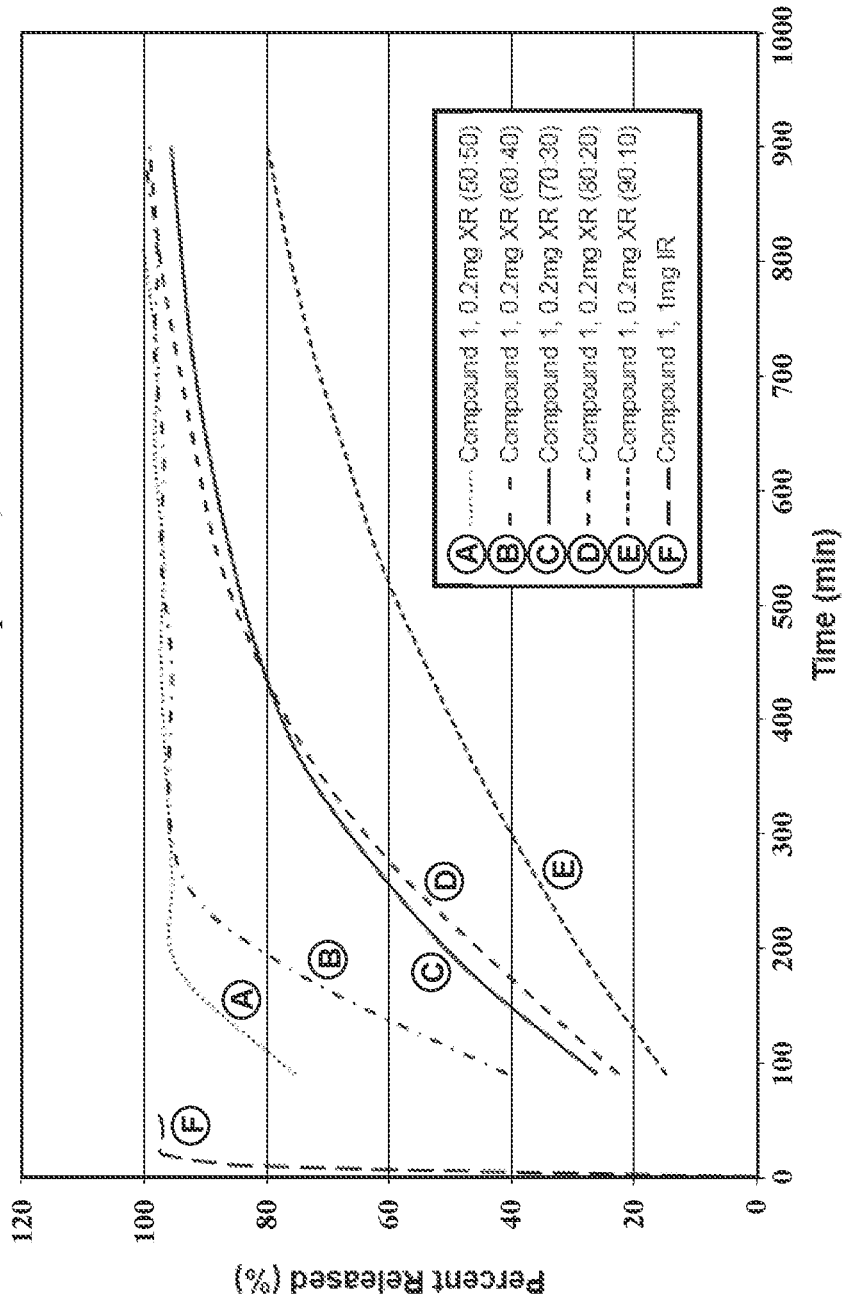
FIG. 3 shows dissolution profiles for a capsule containing Compound 1 with varying ratios of Gelucire® 50/13:Kolliphor® RI-140. An immediate release (IR) composition profile (left-most plot) is also shown for comparison.

The resulting release profiles are shown in FIG. 3, Unless otherwise specified, the release profiles for capsules were measured using USP Apparatus 2 (paddle). As FIG. 3 clearly shows. Gelucire® 50/13 modifies the release rate of Compound 1 relative an immediate release composition. In particular, the release rates were substantially reduced from an immediate release composition (left-most plot in FIG. 3) to the composition having a 50:50 ratio of Gelucire® 50/13 to Kolliphor® RH40 (second plot from the left in FIG. 3 data points are indicated with circles). The release rate was further reduced from the composition having a 80:20 ratio of Gelucire® 50/13 to Kolliphor® RH40 to the composition having a 90:10 ratio (for the latter data points are indicated with squares in FIG. 3).

Figure 4:
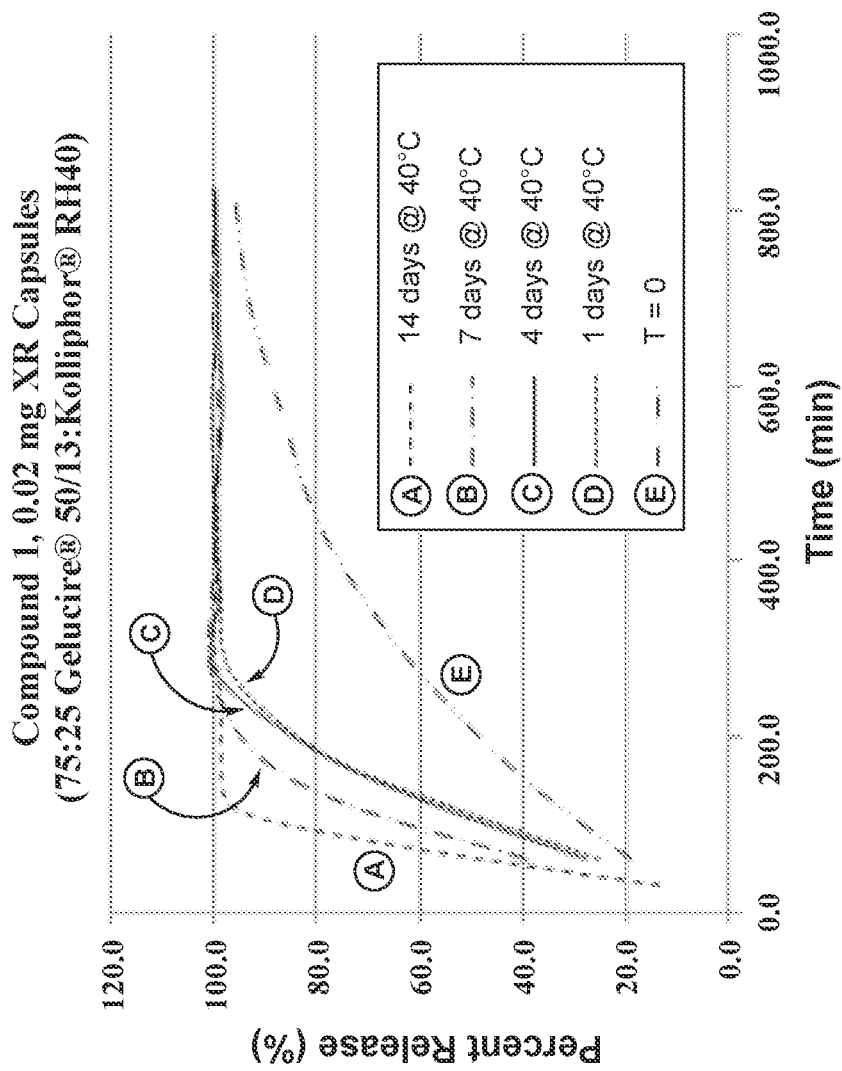
FIG. 4 shows dissolution profiles for a capsule containing Compound 1 with Gelucire® 50/13:Kolliphor® RH40 in a 75:25 ratio at various storage times.
Figure 5A:
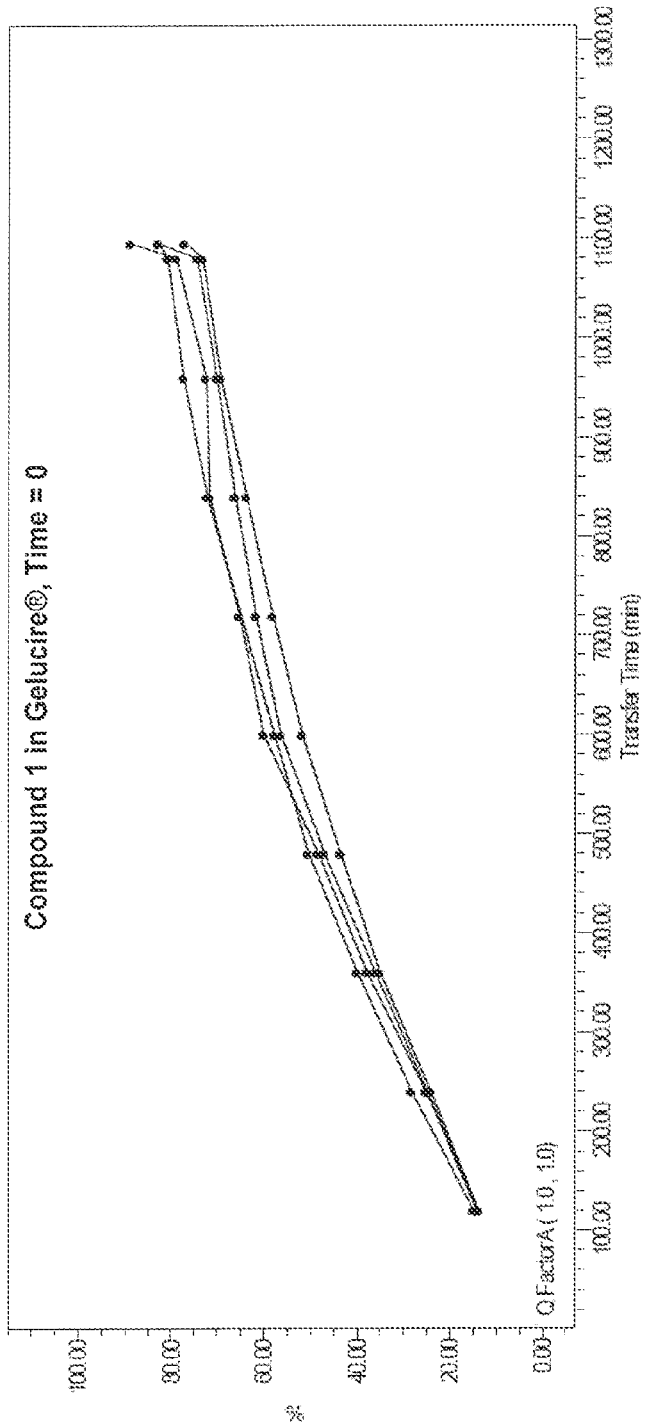
FIGS. 5A, 5B, and 5C shows a dissolution profiles for a 0.04 mg capsule of Compound 1 in Gelucire® 50/13, (i) initially (time=0), FIG. 5A; (ii) after curing for 18 hours at 40° C., FIG. 5B; and (iii) after storage at 40° C. and 75% RH for two weeks, FIG. 5C.
Figure 5B:
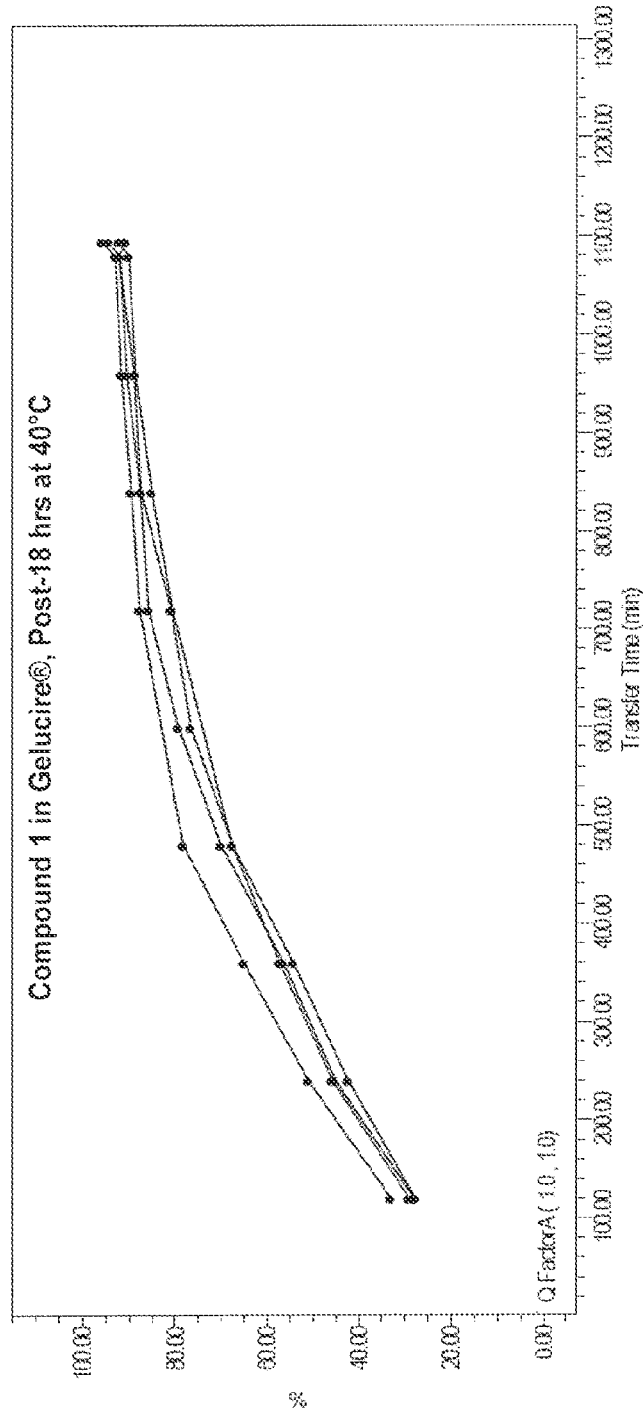
Figure 5C:
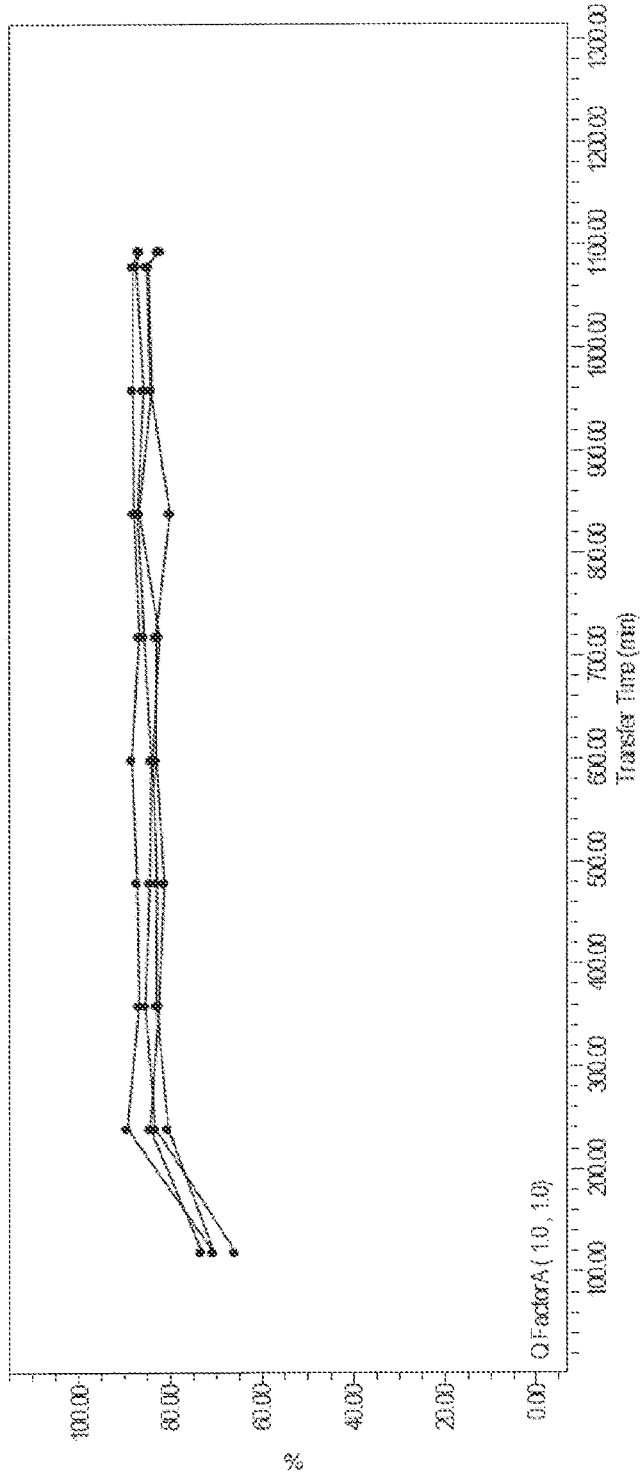

The release profile was found to change following storage over time. In particular, as shown in FIG. 4, the release rate of Compound 1 significantly increased alter storage at 40° C. and 75% RH over time. Similarly, a composition of 0.04 mg of Compound 1 in Gelucire® 50/13 exhibited a rapid increase in release rate of Compound 1 after storage at 40° C. and 75% RH for two weeks, as shown in FIG. 5.

In view of the change in the release profile of the composition over time various factors were considered in an attempt to stabilize the release rate of compositions containing Gelucire® 50/13. These included:
 improving the mixing of the components of the composition;
 adding Gelucire® 50/13 directly as a solid to melted Kolliphor RH40;
 utilizing only previously unheated raw materials;
 evaluating the impact of the following additives upon dissolution: BHT, SiO₂, TiO₂, Talc, & HMPC;
 evaluating the effect of varying cure time & temperature;
 preheating the fill medium of the capsule at 70 to 80° C. to eliminate any "trace" solids None of these attempts were successful in overcoming the problem of the increase in the release rate of Compound 1 after storage.

The following excipients were then evaluated for their release properties and stability of the release rate over time:
 Poloxamer 188
 PEG6000
 HPMC 135
 Gelucire 44/14
 Gelucire 43/01
 HMPC K4M
 Compritol 888 ATO
 Precirol ATO 5
 HPMC E50
 Geleol
 Glycerol Monostearate (GMS)
 Stearic Acid
 Beeswax
 Cetyl Alcohol
 Stearyl Alcohol
 Poloxamer 407
 Poloxamer 338
 Cetostearyl Alcohol
 Carboxymethylcellulose (CMC)

Following this evaluation, Poloxamer 188 and GMS were chosen for further study.

Example 3

Preparation and Testing of Capsules Containing Modified-Release Compositions Containing Poloxamer 188 and Food Grade GMS Table 3a below shows three exemplary embodiments of the composition, Capsules A, B and C. The capsules differ in the ratios of the two excipients Poloxamer 188 and food grade GMS. Capsule A has a Poloxamer 188:food grade GMS ratio of 70:30. Capsule B has a Poloxamer 188:food grade GMS ratio of 50:50. Capsule C has a Poloxamer 188:food grade GMS ratio of 30:70.

TABLE 3a

| | | | mg/capsule | | |
| --- | --- | --- | --- | --- | --- |
| Component | Grade | Function | Capsule A | Capsule B | Capsule C |
| Compound 1 | | Drug substance | 0.030 | 0.030 | 0.030 |
| Glycerol Monostearate (GMS) | Food Grade | Excipient | 104.979 | 74.985 | 44.991 |
| Poloxamer 188 | NF | Excipient | 44.991 | 74.985 | 104.979 |
| | | Fill weight | 150.000 | 150.000 | 150.000 |
| Hard-gelatin capsule[a] (white, Licaps ®) | Capsugel ® internal | Capsule shell | 38.00 | 38.00 | 38.00 |
| | Total capsule target weight[b] | | 188.00 | 188.00 | 188.00 |

[a]Approximate weight. Based on capsule specification.
[b]Theoretical total weight calculated by combining fill and empty capsule weights together.

The pharmaceutical composition was in a size 4 gelatin capsule without sealing. No additional coatings were applied. No silicon dioxide was added to the composition. Since the composition was a hard wax at room temperature, it was not necessary to take measures to avoid leaking such as adding silicon dioxide and/or performing band-sealing. The capsules of Table 3a were prepared according to a manufacturing process as disclosed herein, such as the process schematically shown in FIG. 2. Similarly, capsules analogous to the capsule of Table 3a, having a total of fill weight of 150.000 mg, may be prepared analogously according to a manufacturing process as disclosed herein. In such capsules the weight of Compound 1 may be, for example, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, 0.12 mg, about 0.2 mg, about 0.3 mg, or about 0.5 mg, or about 0.6 mg of Compound 1, and the Poloxamer 188:glycerol monostearate ratio by weight is about 70:30 to 10:90, such as 60:40 to about 20:80, such as about 50:50 to about 30:70, such as about 50:50, such as about 40:60, such as about 30:70.

An exemplary preparation of a capsule containing 0.12 mg of Compound 1 is as follows:

419.66 g of Myverol™ 18-04 K and 179.86 g of Poloxamer 188 are weighed into a 1 L stainless steel beaker. The beaker is placed onto a hot plate stirrer and covered with a heating mantle and foil. An overhead stirrer with a 2" 4 blade impeller is placed into the stainless steel beaker approximately 1 cm from the bottom of the beaker. The hotplate is set for 90° C. and the hotplate and heating mantle are adjusted until a constant temperature of 90±5° C. is maintained. The beaker is purged with nitrogen gas. Purging and heating are maintained overnight to melt the mixture. The overhead stirrer is set to 270 rpm and stirring is initiated. The hotplate temperature is adjusted to a constant temperature of 72.5±2.5° C. 0.4800 g of Compound 1 are weighed in a tare boat and added directly into the vortex of the stainless steel beaker to form a mixture. The 1 L stainless steel beaker is purged with nitrogen gas and covered with aluminum foil. The overhead stirrer is set to 270 rpm and the contents are stirred for a minimum of 30 minutes. A vacuum oven (previously left overnight to reach the desired temperature) is adjusted to a temperature of 72.5° C.±2.5° C. The stainless-steel beaker is transferred into the oven. The mixture is de-gassed for a minimum of 2 hours.

The beaker is placed back onto the hot plate stirrer, purged with nitrogen and stirred at 270 rpm adjusting the hotplate temperature to a constant value of 72.5±2.5°. Based on a trial weighing, the volume of an Autorep E pipette is set to dispense 150 mg of the mixture. The mixture is transferred from the beaker to a size 4, white opaque capsule using the Autorep pipette and a pre-warmed, primed Teflon-wrapped pipette tip. The transfer is repeated until the desired number of capsules is filled. Once the mixture in each capsule is congealed, each capsule cap is pressed onto the body of the capsule until it locks into place.

A zip lock bag containing the capsules is transferred into an oven pre-set at 50° C. The capsules are laid flat and spread evenly and kept in the oven for 36 hours-38 hours.

Capsules containing various ratios of Poloxamer 188 to food grade GMS by weight ere found to be cured in separate runs at the following conditions: Composition containing Poloxamer 188 and food grade GMS in a 70:30 ratio by weight

| Run | Temperature | Time(s) |
| --- | --- | --- |
| 1 | 47.5° C. | 18 hrs |
| 2 | 50° C. | 27 hrs |
| 3a | 52.5° C. | 18 hrs |
| 3b | 52.5° C. | 39 hrs |
| 3c | 52.5° C | 10 hrs |
| 4a | 55° C. | 27 hrs |
| 4b | 55° C. | 10 hrs |

Composition containing Poloxamer 188 and food grade GMS in a 50:50 ratio by weight

| Run | Temperature | Time(s) |
| --- | --- | --- |
| 1 | 40° C. | 1 week |
| 2a | 50° C. | 18 hrs |
| 2b | 50° C. | 39 hrs |
| 3 | 52.5° C. | 27 hrs |
| 4a | 55° C. | 18 hrs |
| 4b | 55° C. | 39 hrs |

Composition containing Poloxamer 188 and food grade GMS in a 30:70 ratio by weight

| Run | Temperature | Time(s) |
| --- | --- | --- |
| 1 | 50° C. | 27 hrs |
| 7a | 52.5° C. | 18 hrs |
| 7b | 52.5° C. | 39 hrs |
| 2c | 52.5° C. | 10 hrs |
| 3a | 55° C. | 27 hrs |
| 3b | 55° C. | 10 hrs |

Figure 6:
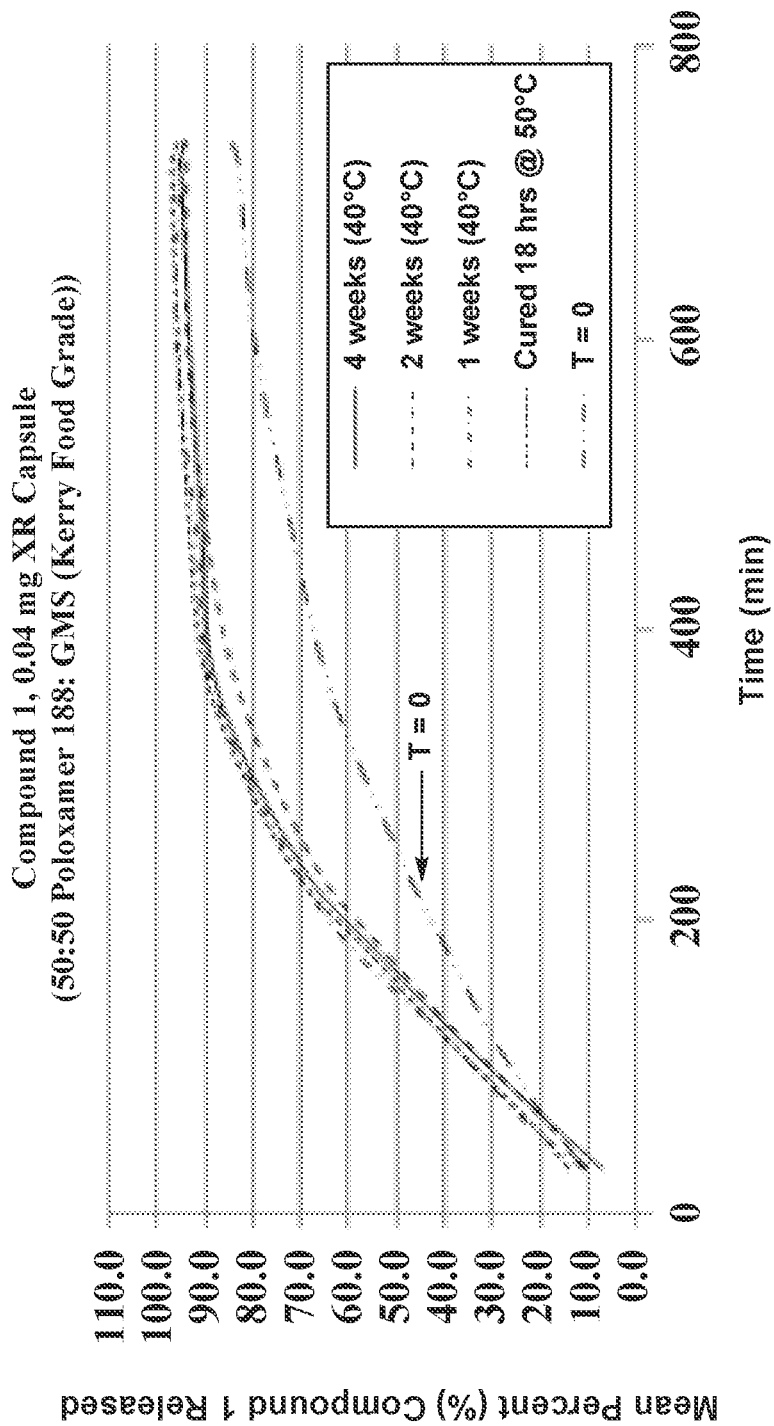
FIG. 6 shows a dissolution profile for a capsule containing Compound 1 in 50:50 Poloxamer 188:food grade CMS (i) uncured (T=0), (ii) after curing at 50° C. for 18 hours, (iii) after storage at 40° C. and 75% RH for one week post-curing, (iv) after storage at 40° C. and 75% RH for two weeks post-curing, and (v) after storage at 40° C. and 75% RH for four weeks post-curing.

FIG. 6 shows release profiles for 0.04 mg of Compound 1 in a capsule containing Poloxamer 188 and food grade GMS in a 50:50 ratio by weight. Curing the pharmaceutical composition stabilized the release profile, as shown by the fact that the release profile following curing for 8 hours was different from the initial release profile (lowest plot in the figure) and remained substantially the same at one week, two weeks, and four weeks post-curing (FIG. 6, remaining four plots in the figure). This is also shown in the following Table 3b. The table shows that the % of Compound 1 released remained substantially the same for compositions following curing for 18 hours and compositions stored subsequently over varying periods of time.

TABLE 3b

Release rate (percentage of Compound 1 released over time) at T = 0 (pre-curing), 18 hrs (curing), 1 week (storage), 2 weeks (storage) and 4 weeks (storage)

| Time (min) | T = 0 | 18 hrs (50° C.) | 1 wk (40° C.) | 2 wks (40° C.) | 4 wks (40° C.) |
| --- | --- | --- | --- | --- | --- |
| 30 | 11.0 | 14.3 | 11.1 | 10.8 | 7.3 |
| 60 | 18.3 | 21.8 | 22.6 | 18.3 | 17.7 |
| 120 | 30.1 | 39.9 | 40.1 | 36.8 | 37.4 |
| 180 | 39.6 | 56.3 | 59.7 | 52.9 | 54.6 |
| 240 | 48.8 | 72.6 | 71.8 | 67.4 | 70.3 |
| 360 | 64.1 | 89.2 | 88.4 | 83.3 | 87.5 |
| 480 | 72.7 | 93.5 | 92.2 | 90.3 | 90.9 |
| 600 | 79.8 | 95.7 | 96.7 | 93.8 | 93.2 |
| 720 | 83.1 | 96.9 | 95.3 | 93.7 | 95.0 |
| 735 | 84.6 | 95.6 | 96.1 | 94.3 | 94.3 |

For the curing to be effective in stabilizing the release profile, food grade glycerol monostearate (food grade GMS) was found to be suitable. When research grade GMS, which has a lower monoester content, was used, curing was not as effective in stabilizing the release profile.

Figure 8:
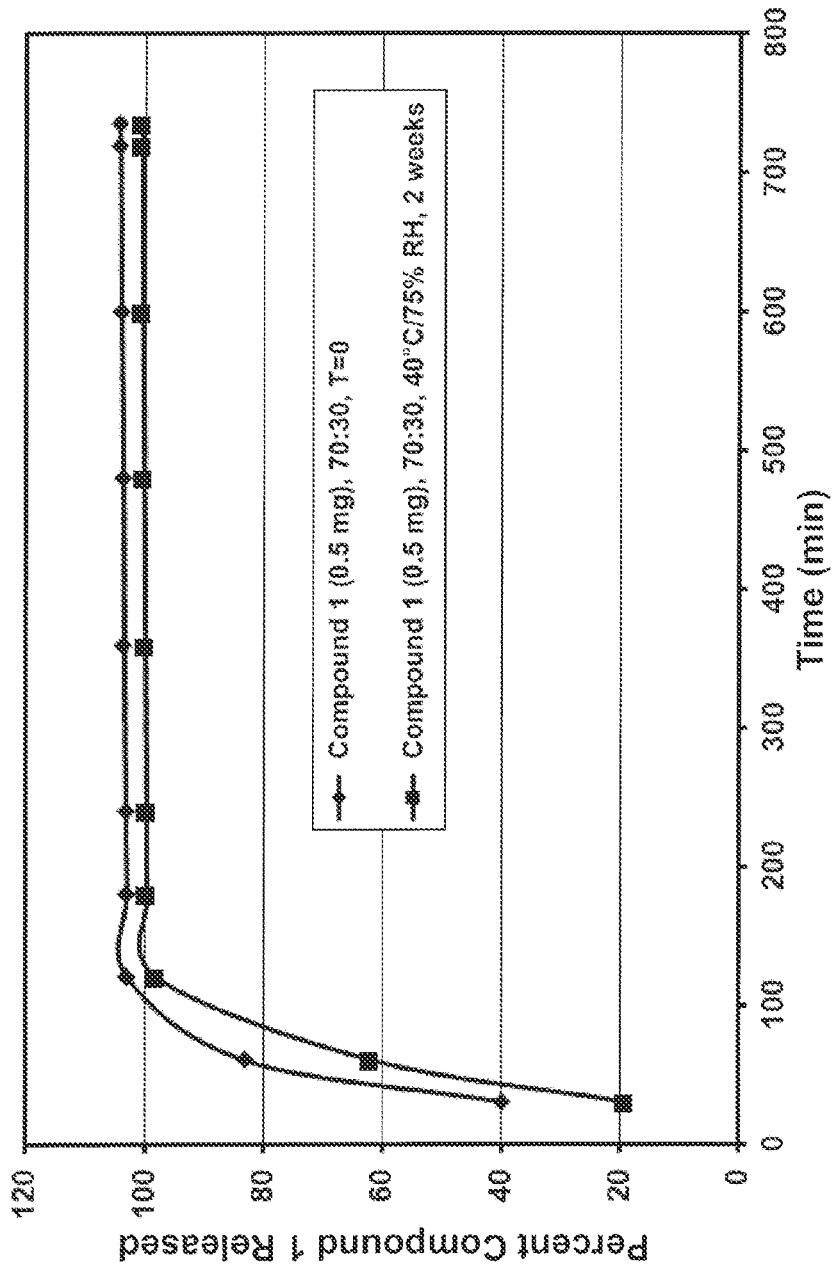
FIG. 8 shows release profiles of a pharmaceutical composition containing Poloxamer 188 and food grade GMS in a 70:30 ratio by weight, and 0.5 mg of Compound 1.
Figure 9:
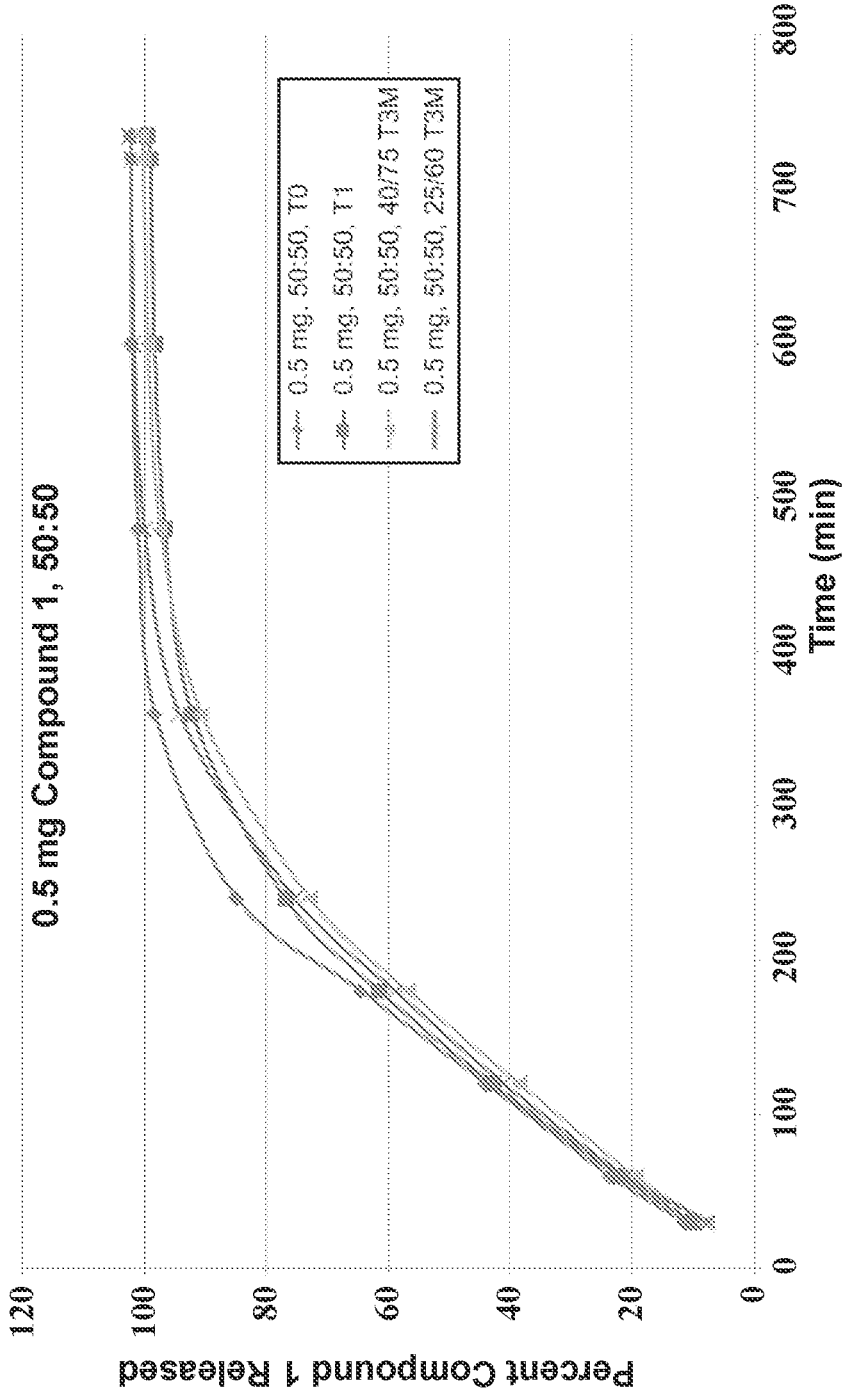
FIG. 9 shows release profiles of a pharmaceutical composition containing Poloxamer 88 and food grade GMS in a 50:50 ratio by weight, and 0.5 mg of Compound 1.
Figure 10:
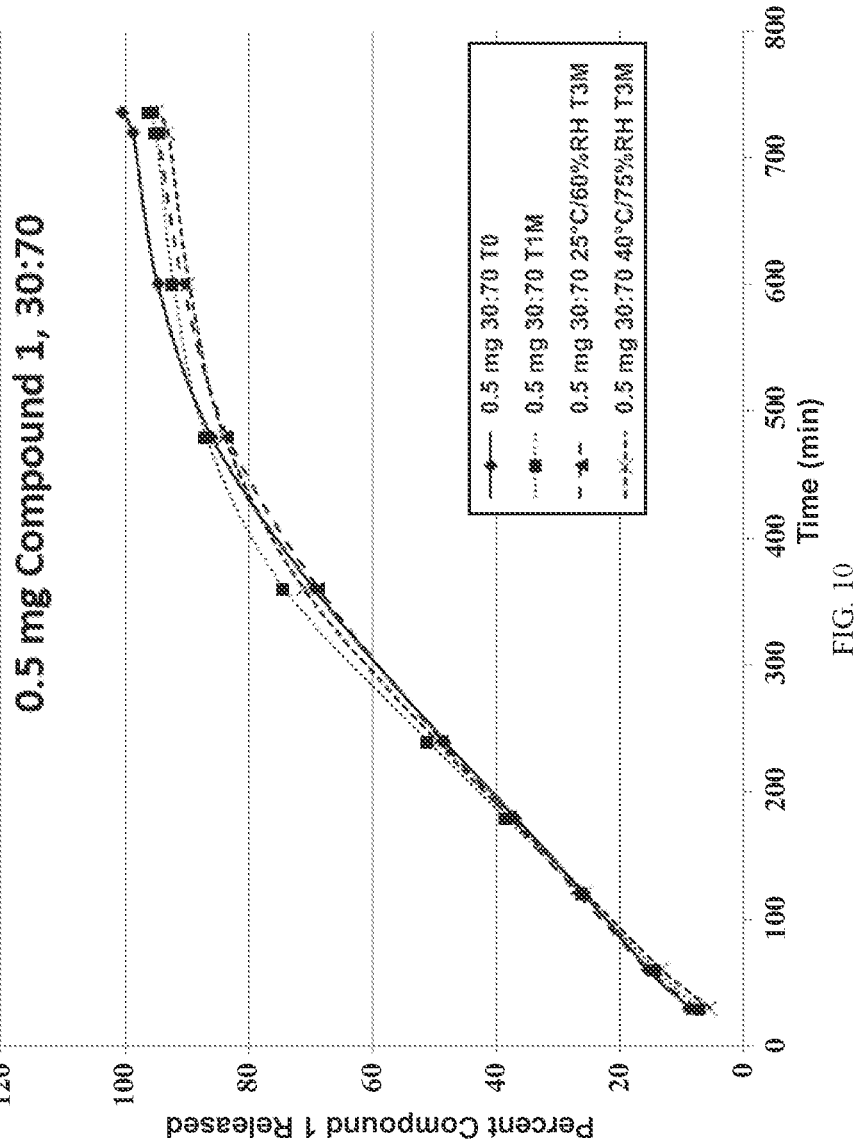
FIG. 10 shows release profiles of a pharmaceutical composition containing Poloxamer 188 and food grade GMS in a 30:70 ratio by weight, and 0.5 mg of Compound 1.
Figure 11A:
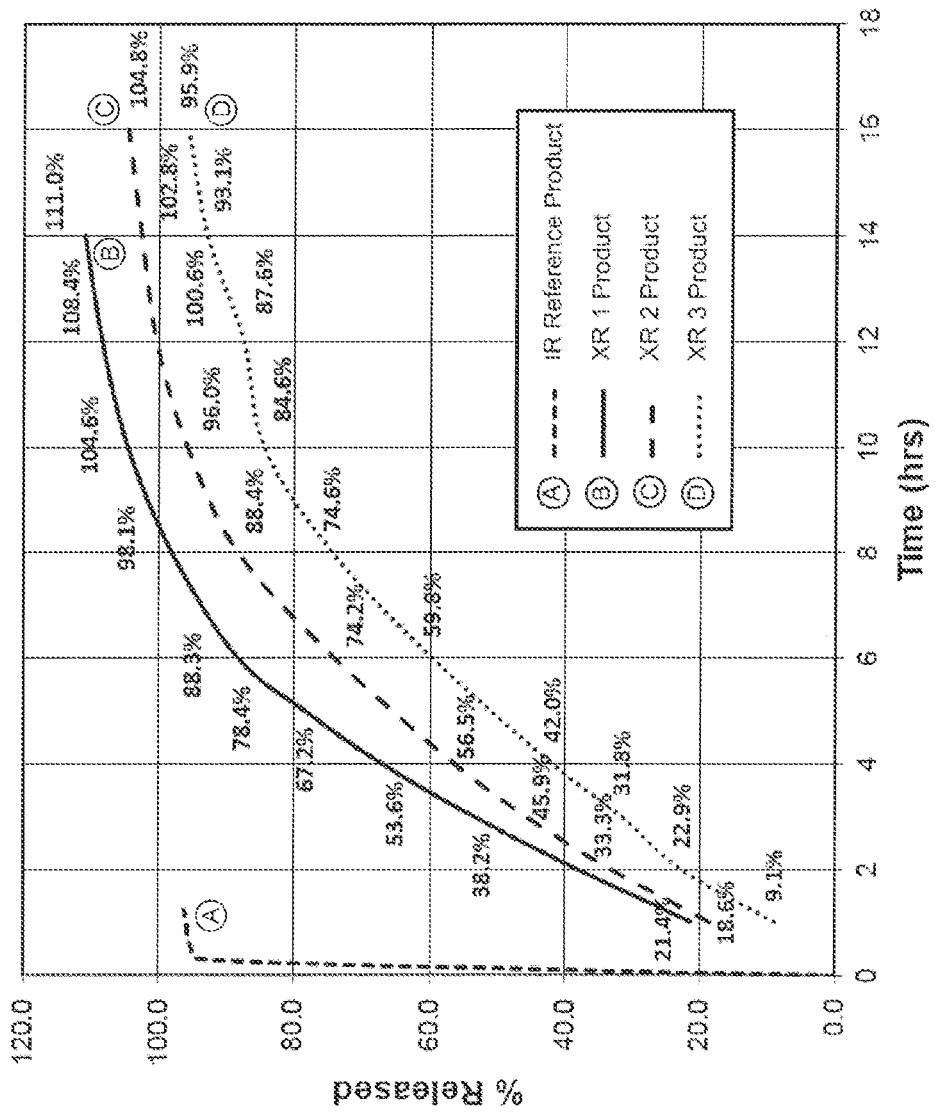
FIG. 11A shows release profiles of the following compositions: (A) Immediate release composition containing 0.03 mg of Compound 1; (B) Composition containing Poloxamer 188 and food grade GMS in a 50:50 ratio by weight, and 0.03 mg of Compound 1; (C) Composition containing Poloxamer 188 and food grade GMS in a 40:60 ratio by weight, and 0.03 mg of Compound 1; (D) Composition containing Poloxamer 188 and food grade GMS in a 30:70 ratio by weight, and 0.03 mg of Compound 1.
Figure 11B:
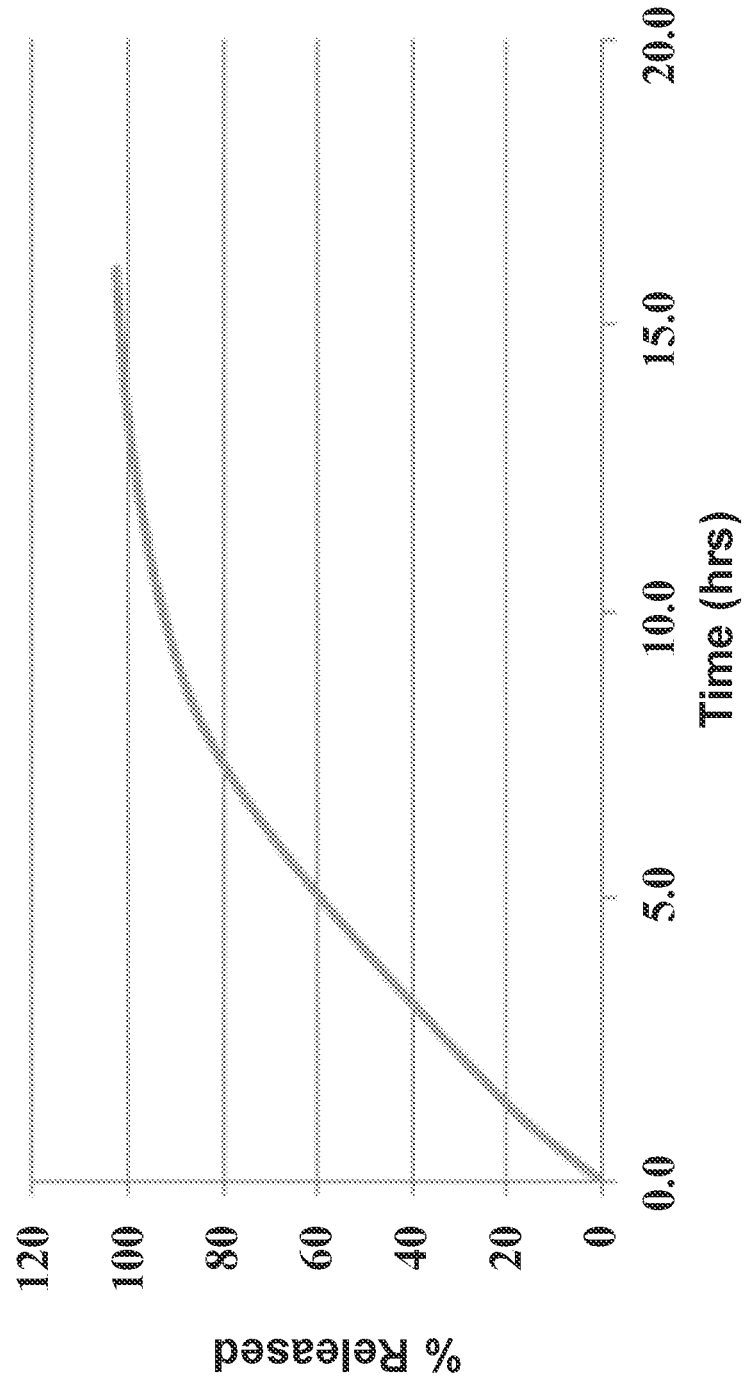
FIG. 11B shows a release profile for a composition containing Poloxamer 188 and food grade GMS in a 30:70 ratio by weight, and 0.12 mg of Compound 1.

The release profiles of pharmaceutical compositions containing Poloxamer 188 and food grade GMS in a 70:30 ratio, a 50:50 ratio, and a 30:70 ratio by weight, each with 0.5 mg of Compound 1, are shown in FIGS. 8, 9, and 10, respectively. FIGS. 8-10 shows that the respective compositions provided a release of Compound 1 at a slower rate than the immediate-release composition shown in FIG. 1 in the left-most plot of FIG. 3. The compositions of FIGS. 8-10 also provided a release of Compound 1 at a rate that was substantially the same after storage at 40° C. and 75% RH for about one month, unlike the modified-release compositions of FIGS. 4 and 5.

Further examples of release rates (% by weight) are shown in Tables 3c-3p. All release profiles disclosed in Tables 3c-3p were measured with USP Apparatus 2 (paddle) at 50 rpm in 500 mL, of aqueous sodium phosphate at a concentration of 0.05 M (pH=6.8). The values in a given table relate to capsules obtained from the same batch. Values shown represent mean values over a number of dissolution tests ("n" in each table) in each case.

TABLE 3c

% of Compound 1 that is released for size 4 capsule containing 0.03 mg of Compound 1 and Poloxamer 188:food grade GMS 70:30 (ratio by weight)—total weight of Poloxamer 188 plus food grade GMS = 149.97 mg

|  | 20* | 30* | 45* | 60* | 90* | 120* |
|---|---|---|---|---|---|---|
| mean value (n = 6) of % of Compound 1 released | 14.8 | 36.1 | 65.4 | 83.8 | 95.5 | 98.4 |
| % RSD** |  | 44.8 | 38.3 | 29.7 | 24.4 | 15.8 | 9.6 |

*time in minutes
**RSD as a percentage of mean value of % of Compound 1 released

TABLE 3d

% of Compound 1 that is released for size 4 capsule containing 0.5 mg of Compound 1 and Poloxamer 188:food grade GMS 70:30 (ratio by weight)-total weight of Poloxamer 188 plus food grade GMS = 149.5 mg

|  | 30* | 60* | 120* |
|---|---|---|---|
| mean value (n = 4) of % of Compound 1 released | 13.8 | 60.2 | 92.1 |
| % RSD** | 42.4 | 8.5 | 8.5 |

*time, in minutes
**RSD as a percentage of mean value of % of Compound 1 released

TABLE 3e

% of Compound 1 that is released for size 4 capsule containing 0.5 mg of Compound 1 and Poloxamer 188:food grade GMS 70:30 (ratio by weight)-total weight of Poloxamer 188 plus food grade GMS = 149.5 mg

|  | 30* | 60* | 120* |
|---|---|---|---|
| mean value (n = 4) of % of Compound 1 released | 17.7 | 56.9 | 95.1 |
| % RSD** | 79.1 | 31.5 | 6.7 |

*time in minutes
**RSD as a percentage of mean value of % of Compound 1 released

TABLE 3f

% of Compound 1 that is released for size 4 capsule containing 0.5 mg of Compound 1 and Poloxamer 188:food grade GMS 70:30 (ratio by weight)-total weight of Poloxamer 188 plus food grade GMS = 149.5 mg

|  | 30* | 60* | 120* |
|---|---|---|---|
| mean value (n = 4) of % of Compound 1 released | 19.3 | 61.9 | 98.1 |
| % RSD** | 74.7 | 42.7 | 7.5 |

*time in minutes
**RSD as a percentage of mean value of % of Compound 1 released

TABLE 3g-1

Storage Time = 0: % of Compound 1 that is released for size 4 capsule containing 0.5 mg of Compound 1 and Poloxamer 188:food grade GMS 70:30 (ratio by weight)-total weight of Poloxamer 188 plus food grade GMS = 149.5 mg

|  | 30* | 45* | 60* |
|---|---|---|---|
| mean value (n =4) of % of Compound 1 released | 33.0 | 64.2 | 86.0 |
| % RSD** | 56.4 | 32.4 | 19.6 |

*time in minutes
**RSD as a percentage of mean value of % of Compound 1 released

TABLE 3g-2

Storage Time = 2 weeks: % of Compound 1 that is released for size 4 capsule containing 0.5 mg of Compound 1 and Poloxamer 188:food grade GMS 70:30 (ratio by weight)-total weight of Poloxamer 188 plus food grade GMS = 149.5 mg

|  | 30* | 45* | 60* |
|---|---|---|---|
| mean value (n = 41) of % of Compound 1 released | 33.0 | 64.2 | 86.0 |
| % RSD** | 56.4 | 32.4 | 19.6 |
| mean value (n = 4) of % of Compound 1 released | 34.8 | 67.9 | 89.4 |
| % RSD** | 52.3 | 24.6 | 9.2 |

TABLE 3h

% of Compound 1 that is released for size 4 capsule containing 0.03 mg of Compound 1 and Poloxamer 188:food grade GMS 50:50 (ratio by weight)—total weight of Poloxamer188 plus food grade GMS = 149.97 mg

|  | 60* | 120* | 180* | 240* | 300* | 360* | 480* |
|---|---|---|---|---|---|---|---|
| mean value (n = 6) of % of Compound 1 released | 17.9 | 35.9 | 51.7 | 67.9 | 83.6 | 92.3 | 98.1 |
| % RSD** | 11.7 | 7.1 | 6.8 | 5.0 | 6.2 | 6.3 | 4.3 |

*time in in mutes
**RSD as a percentage of mean value of % of Compound 1 released

TABLE 3i

% of Compound 1 that is released for size 4 capsule containing 0.5 mg of Compound 1 and Poloxamer 188:food grade GMS 50:50 (ratio by weight)—total weight of Poloxamer 188 plus food grade GMS = 149.5 mg

|  | 30* | 60* | 120* | 180* | 240* | 360* | 480* |
|---|---|---|---|---|---|---|---|
| mean value (n = 4) of % of Compound 1 released | 7.5 | 21.1 | 41.1 | 58.9 | 75.3 | 94.3 | 100.0 |
| % RSD** | 256 | 8.1 | 5.7 | 5.3 | 5.0 | 3.7 | 1.0 |

*time in minutes
**RSD as a percentage of mean value of % of Compound 1 released

TABLE 3j

% of Compound 1 that is released for size 4 capsule containing 0.5 mg of Compound 1 and Poloxamer 188:food grade GMS 50:50 (ratio by weight)—total weight of Poloxamer 188 plus food grade GMS = 149.5 mg

|  | 30* | 60* | 120* | 180* | 240* | 360* | 480* |
|---|---|---|---|---|---|---|---|
| mean value (n = 4) of % of Compound 1 released | 7.8 | 19.5 | 38.6 | 56.8 | 72.9 | 90.7 | 97.4 |
| % RSD** | 17.1 | 8.3 | 7.5 | 5.3 | 3.6 | 2.0 | 1.7 |

*time in minutes
**RSD as a percentage of meana of % of Compound 1 released

TABLE 3k

% of Compound 1 that is released for size 4 capsule containing 0.03 mg of Compound 1 and Poloxamer 188: food grade GMS 50:50 (ratio by weight)-total weight of Poloxamer 188 plus food grade GMS = 149.97 mg

|  | 30* | 60* | 120* | 180* | 240* | 360* | 480* |
|---|---|---|---|---|---|---|---|
| mean value (n = 6) of % of Compound 1 released | 8.5 | 18.0 | 39.3 | 58.6 | 75.2 | 91.4 | 98.3 |
| % RSD** | 80.5 | 11.1 | 10.1 | 7.3 | 5.2 | 2.5 | 3.8 |

*time in minutes
**RSD as a percentage of mean value of % Compound 1 released

TABLE 3l

% of Compound 1 that is released for size 4 capsule containing 0.5 mg of Compound 1 and Poloxamer 188: food grade GMS 50:50 (ratio by weight)-total weight of Poloxamer 188 plus food grade GMS = 149.5 mg

|  | 30* | 60* | 120* | 180* | 240* | 360* | 480* |
|---|---|---|---|---|---|---|---|
| mean value (n = 4) of % of Compound 1 released | 9.9 | 22.2 | 42.9 | 61.5 | 76.9 | 92.2 | 96.7 |
| % RSD** | 12.4 | 8.6 | 10.5 | 8.9 | 5.9 | 4.0 | 2.1 |

*time in minutes
**RSD as a percentage of mean value of % of Compound 1 released

TABLE 3m

% of Compound 1 that is released for size 4 capsule containing 0.03 mg of Compound 1 and Poloxamer 188: food grade GMS 30:70 (ratio by weight)-total weight of Poloxamer 188 plus food grade GMS = 149.97 mg

|  | 60* | 120* | 180* | 240* | 360* | 480* | 600* | 720* | 840* |
|---|---|---|---|---|---|---|---|---|---|
| mean value (n = 6) of % of Compound 1 released | 15.3 | 27.4 | 38.4 | 49.0 | 70.1 | 85.9 | 93.5 | 97.6 | 99.0 |
| % RSD** | 8.8 | 8.7 | 3.5 | 4.0 | 3.5 | 2.2 | 1.9 | 0.9 | 1.0 |

*time in minutes
**RSD as a percentage of mean value of % Compound 1 released

TABLE 3n

% of Compound 1 that is released for size 4 capsule containing 0.5 mg of Compound 1 and Poloxamer 188: food grade GMS 30:70 (ratio by weight)-total weight of Poloxamer 188 plus food grade GMS = 149.5 mg

|  | 30* | 60* | 120* | 180* | 240* | 360* | 480* | 600* | 720* | 735* |
|---|---|---|---|---|---|---|---|---|---|---|
| mean value (n = 4) of % of Compound 1 released | 7.9 | 15.5 | 26.9 | 37.9 | 48.8 | 68.7 | 83.4 | 90.6 | 94.7 | 95.7 |
| % RSD** | 14.7 | 5.1 | 5.6 | 5.7 | 6.0 | 5.2 | 2.6 | 2.0 | 1.9 | 1.5 |

*time in minutes
**RSD as a percentage of mean value of % Compound 1 released

TABLE 3o

% of Compound 1 that is released for size 4 capsule containing 0.5 mg of Compound 1 and Poloxamer 188: food grade GMS 30:70 (ratio by weight)-total weight of Poloxamer 188 plus food grade GMS = 149.5 mg

|  | 30* | 60* | 120* | 180* | 240* | 360* | 480* | 600* | 720* | 735* |
|---|---|---|---|---|---|---|---|---|---|---|
| mean value (n = 4) of % of Compound 1 released | 5.6 | 13.3 | 25.5 | 37.7 | 49.7 | 71.2 | 84.0 | 89.7 | 93.1 | 94.8 |
| % RSD** | 17.5 | 6.7 | 7.4 | 5.9 | 4.7 | 3.4 | 1.2 | 0.7 | 0.8 | 1.2 |

*time in minutes
**RSD as a percentage of mean value of % of Compound 1 released

TABLE 3p

% of Compound 1 that is released for size 4 capsule containing 0.5 mg of Compound 1 and Poloxamer 188: food grade GMS 30:70 (ratio by weight)-total weight of Poloxamer 188 plus food grade GMS = 149.5 mg

|  | 30* | 60* | 120* | 180* | 240* | 360* | 480* | 600* | 720* | 735* |
|---|---|---|---|---|---|---|---|---|---|---|
| mean value (n = 4) of % of Compound 1 released | 7.3 | 14.3 | 26.1 | 38.5 | 51.1 | 74.3 | 87.0 | 92.3 | 95.0 | 96.1 |
| % RSD** | 7.7 | 8.1 | 5.4 | 5.2 | 7.4 | 10.0 | 7.7 | 4.9 | 2.9 | 2.2 |

*time in minutes
**RSD as a percentage of mean value of % of Compound 1 released

TABLE 3q

% of Compound 1 that is released for size 4 capsule containing 0.5 mg of Compound 1 and Poloxamer 188: food grade GMS 30:70 (ratio by weight)-total weight of Poloxamer 188 plus food grade GMS = 149.5 mg

|  | 30* | 60* | 120* | 180* | 240* | 360* | 480* | 600* | 720* | 735* |
|---|---|---|---|---|---|---|---|---|---|---|
| mean value (n = 4) of % of Compound 1 released | 6.2 | 13.7 | 27.3 | 40.3 | 52.5 | 74.2 | 85.5 | 91.5 | 93.4 | 94.5 |
| % RSD** | 18.6 | 9.6 | 6.7 | 9.2 | 9.8 | 10.7 | 7.7 | 6.4 | 4.3 | 3.5 |

*time in minutes
**RSD as a percentage of mean value of % of Compound 1 released

TABLE 3r

% of Compound 1 that is released for size 4 capsule containing 0.03 mg of Compound 1 and Poloxamer 188: food grade GMS 30:70 (ratio by weight)-total weight of Poloxamer 188 plus food grade GMS = 149.97 mg

|  | 60* | 120* | 180* | 240* | 360* | 480* | 600* | 720* | 840* |
|---|---|---|---|---|---|---|---|---|---|
| mean value (n = 6) of % of Compound 1 released | 11 | 23 | 33 | 43 | 62 | 77 | 87 | 91 | 95 |
| % RSD** | 2.4 | 1.7 | 1.9 | 2.3 | 2.8 | 3.5 | 2.8 | 3.6 | 2.7 |

*time in minutes
**RSD as a percentage of mean value of % of Compound 1 released

TABLE 3s-1

Storage time = 0: % of Compound 1 that is released for size 4 capsule containing 0.03 mg of Compound 1 and Poloxamer 188: food grade GMS 30:70 (ratio by weight)-total weight of Poloxamer 188 plus food grade GMS = 149.97 mg

|  | 60* | 120* | 180* | 240* | 360* | 480* | 600* |
|---|---|---|---|---|---|---|---|
| mean value (n = 6) of % of Compound 1 released | 16.7 | 27.5 | 38.3 | 50.3 | 72.3 | 88.7 | 96.0 |
| % RSD** | 5.5 | 5.8 | 5.8 | 5.5 | 6.2 | 4.3 | 3.2 |

TABLE 3s-2

Storage time = 2 weeks: % of Compound 1 that is released for size 4 capsule containing 0.03 mg of Compound 1 and Poloxamer 188: food grade GMS 30:70 (ratio by weight)- total weight of Poloxamer 188 plus food grade GMS = 149.97 mg

|  | 60* | 120* | 180* | 240* | 360* | 480* | 600* |
|---|---|---|---|---|---|---|---|
| mean value (n = 6) of % of Compound 1 released | 16.0 | 27.7 | 39.7 | 52.2 | 74.6 | 89.4 | 96.7 |
| % RSD** | 2.3 | 4.6 | 3.6 | 4.3 | 4.0 | 3.0 | 2.1 |

Example 4

Modified-Release Compositions—Tablets

An example of a suitable composition is a composition in the form of a tablet. Examples of modified-release tablets at various doses of Compound 1 are shown 41 Table 4.

TABLE 4

| Ingredient | % (w/w) | mg/tablet | % (w/w) | mg/tablet | % (w/w) | mg/tablet |
|---|---|---|---|---|---|---|
| Compound 1 | 0.00 | 0.00 | 0.05 | 0.05 | 0.10 | 0.10 |
| HPMC (Methocel K4M Premium CR) | 25.00 | 25.00 | 25.00 | 25.00 | 25.00 | 25.00 |
| HPMC (Methocel K100 Premium LVCR) | 25.00 | 25.00 | 25.00 | 25.00 | 25.00 | 25.00 |
| Microcrystalline cellulose (Avicel PH102) | 30.00 | 30.00 | 30.00 | 30.00 | 30.00 | 30.00 |
| Mannitol (Pearlitol 100SD) | 18.75 | 18.75 | 18.70 | 18.70 | 18.65 | 18.65 |
| Silicon dioxide | 0.25 | 0.25 | 0.25 | 0.25 | 0.25 | 0.25 |
| Magnesium stearate | 1.00 | 1.00 | 1.00 | 1.00 | 1.00 | 1.00 |
| Total (core tablet) | 100.00 | 100.00 | 100.00 | 100.00 | 100.00 | 100.00 |
| Ethanol for preparing wet granulation liquid *a* | 15.00 | — | 15.00 | — | 15.00 | — |
| Ethanol for rinsing the container *a* | 5.00 | — | 5.00 | — | 5.00 | — |
| Total amount of ethanol used | 20.00 | — | 20.00 | — | 20.00 | — |
| Opadry II Orange 89F130009 | — | 4.00 | — | 4.00 | — | 4.00 |

*a* Essentially removed during processing

| Ingredient | % (w/w) | mg/tablet | % (w/w) | mg/tablet |
|---|---|---|---|---|
| Compound 1 | 0.20 | 0.20 | 0.50 | 0.50 |
| HPMC (Methocel K4M Premium CR) | 25.00 | 25.00 | 25.00 | 25.00 |
| HPMC (Methocel K100 Premium LVCR) | 25.00 | 25.00 | 25.00 | 25.00 |
| Microcrystalline cellulose (Avicel PH102) | 30.00 | 30.00 | 30.00 | 30.00 |
| Mannitol (Pearlitol 100SD) | 18.55 | 18.55 | 18.25 | 18.25 |
| Silicon dioxide | 0.25 | 0.25 | 0.25 | 0.25 |
| Magnesium stearate | 1.00 | 1.00 | 1.00 | 1.00 |
| Total (core tablet) | 100.00 | 100.00 | 100.00 | 100.00 |
| Ethanol for preparing wet granulation liquid *a* | 15.00 | — | 15.00 | — |
| Ethanol for rinsing the container *a* | 5.00 | — | 5.00 | — |
| Total amount of ethanol used | 20.00 | — | 20.00 | — |
| Opadry II Orange 89F130009 |  | 4.00 |  | 4.00 |

*a* Essentially removed during processing

| Component | Grade | Function | Unit Formula (mg) | | |
|---|---|---|---|---|---|
|  |  |  | 0.05 mg active | 0.25 mg active | 0.40 mg active |
| Core |  |  |  |  |  |
| Compound 1 |  | Drug substance | 0.05 | 0.25 | 0.40 |
| Ethyl Alcohol*a* | USP | Vehicle | 0.00 | 0.00 | 0.00 |
| Hydroxypropyl methylcellulose K4M CR | Ph. Eur./USP | Release modifier | 25.00 | 25.00 | 25.00 |
| Hydroxypropyl methylcellulose K100 LVCR | Ph. Eur./USP | Release modifier | 25.00 | 25.00 | 25.00 |
| Microcrystalline cellulose (Avicel PH102) | Ph. Eur./USP | Filler | 30.00 | 30.00 | 30.00 |

TABLE 4-continued

| | | | | | |
|---|---|---|---|---|---|
| Mannitol (Pearlitol 100 SD) | Ph. Eur./USP | Filler | 18.70 | 18.50 | 18.35 |
| Colloidal silicon dioxide | Ph. Eur./USP | Glidant | 0.25 | 0.25 | 0.25 |
| Magnesium stearate | Ph. Eur./USP | Lubricant | 1.00 | 1.00 | 1.00 |
| | Tablet core | | 100.00 | 100.00 | 100.0 |
| | Film coating | | | | |
| Opadry ® II Orange 89F130009[b] | Colorcon specification | Color film coat | 4.00 | 4.00 | 4.00 |
| Purified water[a] | USP | Processing aid/solvent | 0.00 | 0.00 | 0.00 |
| | Film coating | | 4.00 | 4.00 | 4.00 |
| | Total | | 104.00 | 104.00 | 104.00 |

[a]Wet granulation fluid, essentially removed during processing.
[b]Manufactured by Colorcon, refer to Section 3.2.P.4 and DMF 721 for detailed information and qualitative composition.

Suppliers and grades for various components of the tablet are shown in Table 5.

TABLE 5

| Component | Manufacturer | Supplier Grade |
|---|---|---|
| Compound 1 | Arena | Internal |
| Ethanol | Pharma-Aaper | 200 Proof |
| Hydroxypropyl Methylcellulose | The Dow Company | Methocel K4M Premium CR |
| Hydroxypropyl Methylcellulose | The Dow Company | Methocel K100 Premium LVCR |
| Microcrystalline Cellulose | FMC Biopolymer | Avicel PH102 |
| Mannitol | Roquette | Peartitol 100SD |
| Silicon dioxide | Evonik | Aerosil ® 200 Pharma |
| Magnesium stearate | Mallinckrodt | Hyqual 5712 vegetable |
| Opadry II Orange | Coloreon | 89F130009 |

Example 5

Preparation of Modified-Release Tablets

An exemplary process for the preparation of modified-release tablets is as follows.

A wet granulation liquid is prepared as follows. Ethanol is weighed out and added into a beaker. A 4-blade propeller is attached to an IKA RW20 overhead mixer and lowered into the beaker. Compound 1 is weighed out and slowly added to the beaker, mixing until dissolved.

Granulation is prepared as follows. Hydroxypropyl methylcellulose (Methocel K4M CR) is weighed out and sieved through a Comil with 8045 screen. Sieved powder is added to the processing bowl of the high shear mixer. The impeller speed is set to 100 rpm. Mixing is started and the wet granulation liquid is immediately poured through the top port within 1-2 min. Mixing speed is increased to 250 rpm and continue mixing for 2 min after addition was complete. Half of rinse ethanol is weighed out to rinse the beaker used for preparing the wet granulation liquid. The impeller speed is set to 250 rpm and the chopper speed to 1000 rpm. Mixing is started and the rinse liquid is immediately poured through the top port within 1 min. Mixing is continued for 2 min after addition is complete. The remaining half of rinse ethanol is weighed out to rinse the beaker used for preparing the wet granulation liquid for the 2" time. The impeller speed is set to 250 rpm and the chopper speed to 1000 rpm. Mixing is started and the rinse liquid is immediately poured through the top port within 1 min. Mixing is continued for 2 m in after addition is complete. Wet granules are discharged.

Drying is performed in an oven overnight at 40° C. (±5° C.). In-process testing is performed to determine residual ethanol level.

Milling, blending and lubrication are performed as follows. The ingredients are sieved through the Comil with R045 screen & round-bar impeller at 1500 rpm by the following order: Mannitol. Methocel K100 LVCR dried granules, silicon dioxide, and microcrystalline cellulose. Milled granules and excipients are added into a V-blender. The V-blender is set to 24 rpm and blending is performed for 10 min. The powder blend is discharged and sieving through the Comil again is performed again. Sieved powder blend is added back into the \r-blender. The V-blender is set to 24 rpm and blending is performed for 10 min. Magnesium stearate is sieved through a 20-mesh screen, Magnesium stearate is added into the V-blender. The V-blender is set to 24 rpm and blending is performed for 5 min. The final powder blend is discharged.

Compression of the final blend is performed on a rotary tablet press using ¼ plain, round concave tooling to achieve target tablet weight of 100 mg and target hardness of 7 kp. Color film coating is performed as follows. Purified water is added to a beaker. Opadry II Orange is added and mixing is performed for approximately 45 minutes until the solids are homogeneously dispersed. Coating suspension is applied until the predetermined amount of suspension is sprayed.

Examples of preparations of modified-release tablets are as follows:

(a) A 0.5 kg blend of Compound 1 0.5 mg with 40% HPMC K4M CR was prepared. Twelve tablets were compressed at 100-mg target tablet size and 7-kP target hardness and the release profile was determined. The release rate of the tablets was found to be faster than that of the modified-release capsule.

(b) A 0.5 kg batch of Compound 1 powder blend with 40% HPMC K4M and 10% HPMC K100 LVCR by wet granulation was prepared. Twelve tablets at 100-mg target tablet size and 7-kp target hardness were compressed and the release profile was determined. The release rate of the tablets was found to be faster than that of the modified-release capsule at time points <6 hrs but slower than that of the modified-release capsule at time points ≥6 hrs.

(c) A 0.5 kg batch of Compound 1 powder blend with 30% HPIVIC K411/I and 20% HPMC K100 LVCR by wet granulation was prepared. Twelve tablets at 100-mg target tablet size and 7-kp target hardness were compressed and the release profile was determined. The release rate of the tablets was found to be slightly faster than that of the modified-release capsule.

(d) Compound 1 0.5 mg XR orange film-coated tablets were manufactured. Powder blend with 30% FIPMC K4M and 25% HPMC K100 LVCR was prepared by wet granulation using ethanol as the wet granulation solvent at 0.5-g scale. The powder blend was compressed to produce 100-mg core tablets. Core tablets were film-coated with Opadry II Orange 89F130009 to achieve a weight gain of ≥4%. The composition and amounts dispensed are shown in the table below:

| Ingredient | % (w/w) | Amount per Tablet (mg) | Target Amount In Powder blend (g) | Amount Dispensed (g) | Stages added |
|---|---|---|---|---|---|
| Compound 1 | 0.50 | 0.50 | 2.50 | 2.50 | Wet |
| HPMC K4M CR | 30.00 | 30.00 | 150.00 | 150.00 | granulation |
| HPMC K100 LVCR | 25.00 | 25.00 | 125.00 | 125.00 | Milling & |
| Microcrystalline cellulose | 30.00 | 30.00 | 150.00 | 150.00 | blending |
| Mannitol (Pearlitol 100SD) | 13.25 | 13.25 | 66.25 | 66.25 | with dried |
| Silicon dioxide | 0.25 | 0.25 | 1.25 | 1.25 | granules |
| Magnesium stearate | 1.00 | 1.00 | 5.00 | 5.00 | Lubrication |
| Total (core tablet) | 100.00 | 100.00 | 500.00 | 500.00 | — |
| EtOH for preparing API | 15.00 | — | 75.00 | 75.00 | Wet |
| EtOH for insing the container* | 5.00 | — | 25.00 | 25.10 | granulation |
| Total amount of EtOH used | 20.00 | — | 100.00 | 100.10 | |

*Essentially removed during processing (e) An analogous procedure to d) was used to manufacture tablets having 0.05 mg Compound 1 (the amount of mannitol used was 0.45 mg more than in d)). The composition and amounts dispensed are shown in the table below:

| Ingredient | % (w/w) | Amount per Tablet (mg) | Target Amount In Powder blend (g) | Amount Dispensed (g) | Stages added |
|---|---|---|---|---|---|
| Compound 1 | 0.05 | 0.05 | 0.25 | 0.25 | Wet |
| HPMC K4M CR | 30.00 | 30.00 | 150.00 | 150.00 | granulation |
| HPMC K100 LVCR | 25.00 | 25.00 | 125.00 | 125.00 | Milling & |
| Microcrystalline cellulose | 30.00 | 30.00 | 150.00 | 150.00 | blending |
| Mannitol (Pearlitol 100SD) | 13.70 | 13.70 | 68.50 | 68.50 | with dried |
| Silicon dioxide | 0.25 | 0.25 | 1.75 | 1.25 | granules |
| Magnesium stearate | 1.00 | 1.00 | 5.00 | 5.00 | Lubrication |
| Total (core tablet) | 100.00 | 100.00 | 500.00 | 500.00 | — |
| EtOH for preparing API | 15.00 | — | 75.00 | 75.00 | Wet |
| EtOH for rinsing the container | 5.00 | — | 25.00 | 25.38 | granulation |
| Total amount of EtOH used | 20.00 | — | 100.00 | 100.38 | |

*Essentially removed during processing (f) Compound 1 0.05 mg XR orange film-coated tablets were manufactured. Powder blend was prepared by wet granulation using ethanol as the wet granulation solvent at 0.5-kg scale. The powder blend was compressed to produce 100-mg core tablets at target 7 kp hardness. Approximately 380 g of 100-mg core tablets were produced. Core tablets were film-coated with Opadry II Orange 89F130009, resulting in an actual weight gain of 4.43%.

The composition and amounts dispensed are shown in the table below:

| Ingredient | % (w/w) | Amount per Tablet (mg) | Target Amount In Powder blend (g) | Amount Dispensed (g) | Stages added |
|---|---|---|---|---|---|
| Compound 1 | 0.05 | 0.05 | 0.25 | 0.25 | Wet |
| HPMC K4M CR | 25.00 | 25.00 | 125.00 | 125.00 | granulation |
| HPMC K100 LVCR | 25.00 | 25.00 | 125.00 | 125.00 | Milling & |
| Microcrystalline cellulose | 30.00 | 30.00 | 150.00 | 150.00 | blending |
| Mannitol (Pearlitol 100SD) | 18.70 | 18.70 | 93.50 | 93.50 | with dried |
| Silicon dioxide | 0.25 | 0.25 | 1.25 | 1.25 | granules |
| Magnesium stearate | 1.00 | 1.00 | 5.00 | 5.00 | Lubrication |
| Total (core tablet) | 100.00 | 100.00 | 500.00 | | — |

-continued

| Ingredient | % (w/w) | Amount per Tablet (mg) | Target Amount In Powder blend (g) | Amount Dispensed (g) | Stages added |
|---|---|---|---|---|---|
| EtOH for preparing API | 15.00 | — | 75.00 | 75.00 | Wet granulation |
| EtOH for rinsing the container* | 5.00 | — | 25.00 | 25.00 | |
| Total amount of EtOH used | 20.00 | — | 100.00 | 100.00 | |

*Essentially removed during processing (g) An analogous procedure to f) was used to manufacture tablets having 0.5 mg Compound 1 (the amount of mannitol used was 0.45 mg less than in f)): The composition and amounts dispensed are shown in the table below:

| Ingredient | % (w/w) | Amount per Tablet (mg) | Target Amount In Powder blend (g) | Amount Dispensed (g) | Stages added |
|---|---|---|---|---|---|
| Compound 1 | 0.50 | 0.50 | 2.50 | 2.50 | Wet granulation |
| HPMC K4M CR | 25.00 | 25.00 | 125.00 | 125.00 | |
| HPMC K100 LVCR | 25.00 | 25.00 | 175.00 | 125.00 | Milling & blending with dried granules |
| Microcrystaltine cellulose (Avicel PH102) | 30.00 | 30.00 | 150.00 | 150.00 | |
| Mannitol (Pearlitol 100SD) | 18.25 | 18.25 | 91.25 | 91.30 | |
| Silicon dioxide | 0.75 | 0.25 | 1.25 | 1.25 | |
| Magnesium stearate | 1.00 | 1.00 | 5.00 | 5.00 | Lubrication |
| Total (core tablet) | 100.00 | 100.00 | 500.00 | | — |
| EtOH for preparing API solution* | 15.00 | — | 75.00 | 75.00 | Wet granulation |
| EtOH for rinsing the container* | 5.00 | — | 25.00 | 25.00 | |
| Total amount of EtOH used | 20.00 | — | 100.00 | 100.00 | |

*Essentially removed during processing

Example 6

Release Profiles

The release profiles for modified-release tablets were measured using USP Apparatus 1 (baskets).

Figure 12:
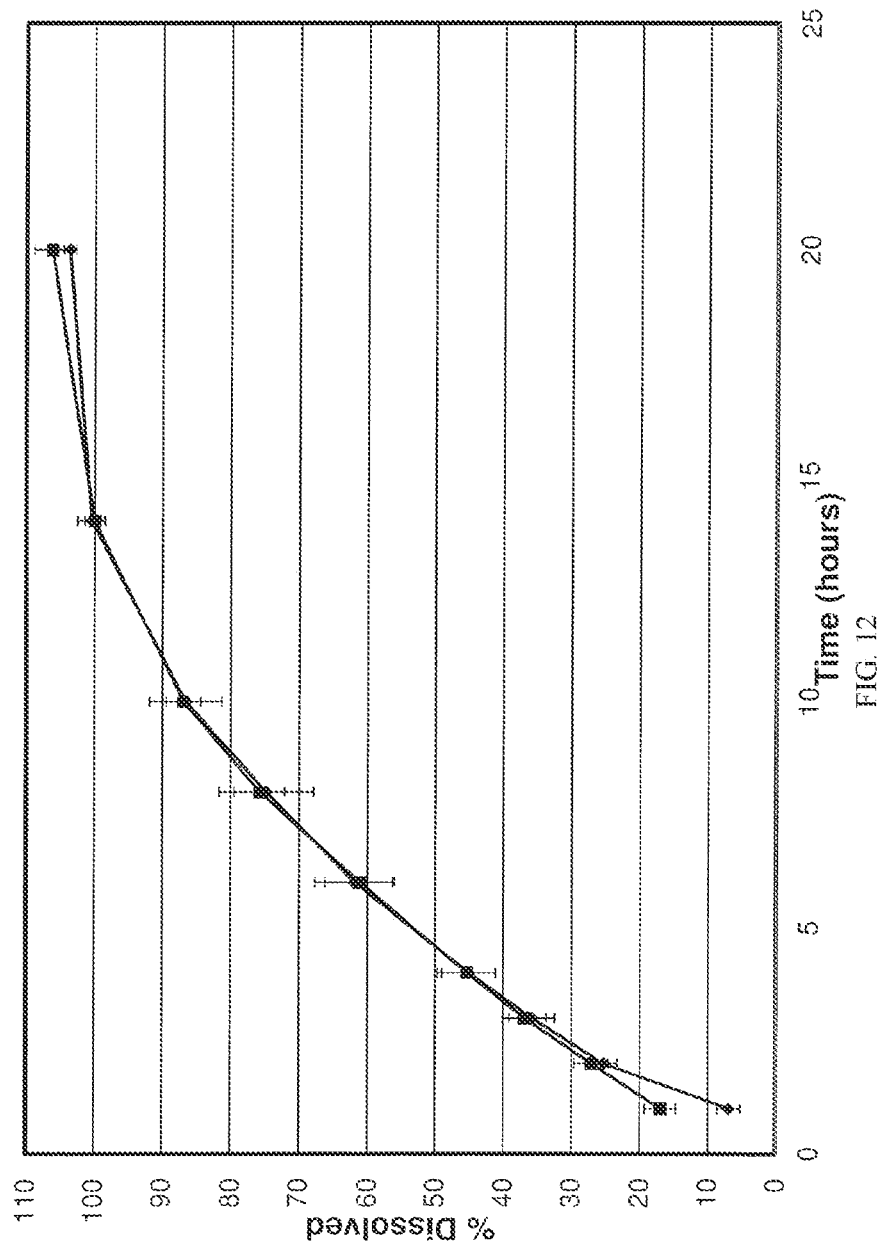
FIG. 12 shows dissolution profiles for a tablet comprising Compound 1 (0.05 mg), Methocel K4M Premium CR (25 mg), and Methocel 100 Premium LVCR (25 mg). The points for each plot represent mean values; (a) diamonds: initial dissolution profile; (b) squares: profile after storage at 40° C. and 75% RH for 6 months.
Figure 13:
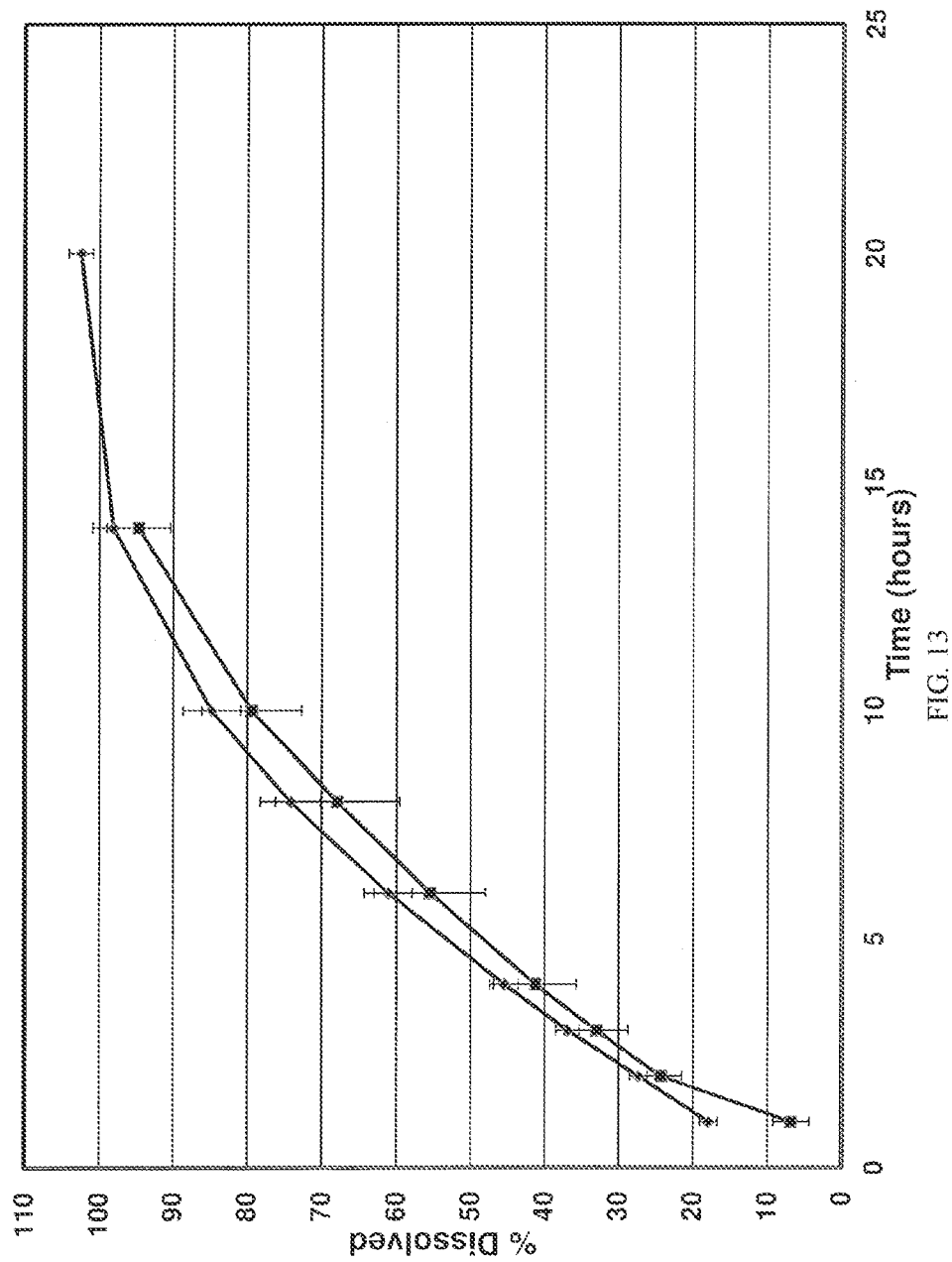
FIG. 13 shows dissolution profiles for a tablet comprising Compound 1 (0.5 mg), Methocel K4M Premium CR (25 mg), and Methocel 100 Premium LVCR (25 mg). The points for each plot represent mean values; (a) diamonds: initial dissolution profile; (b) squares: profile after storage at 40° C. and 75% RH for 6 months.
Figure 14:
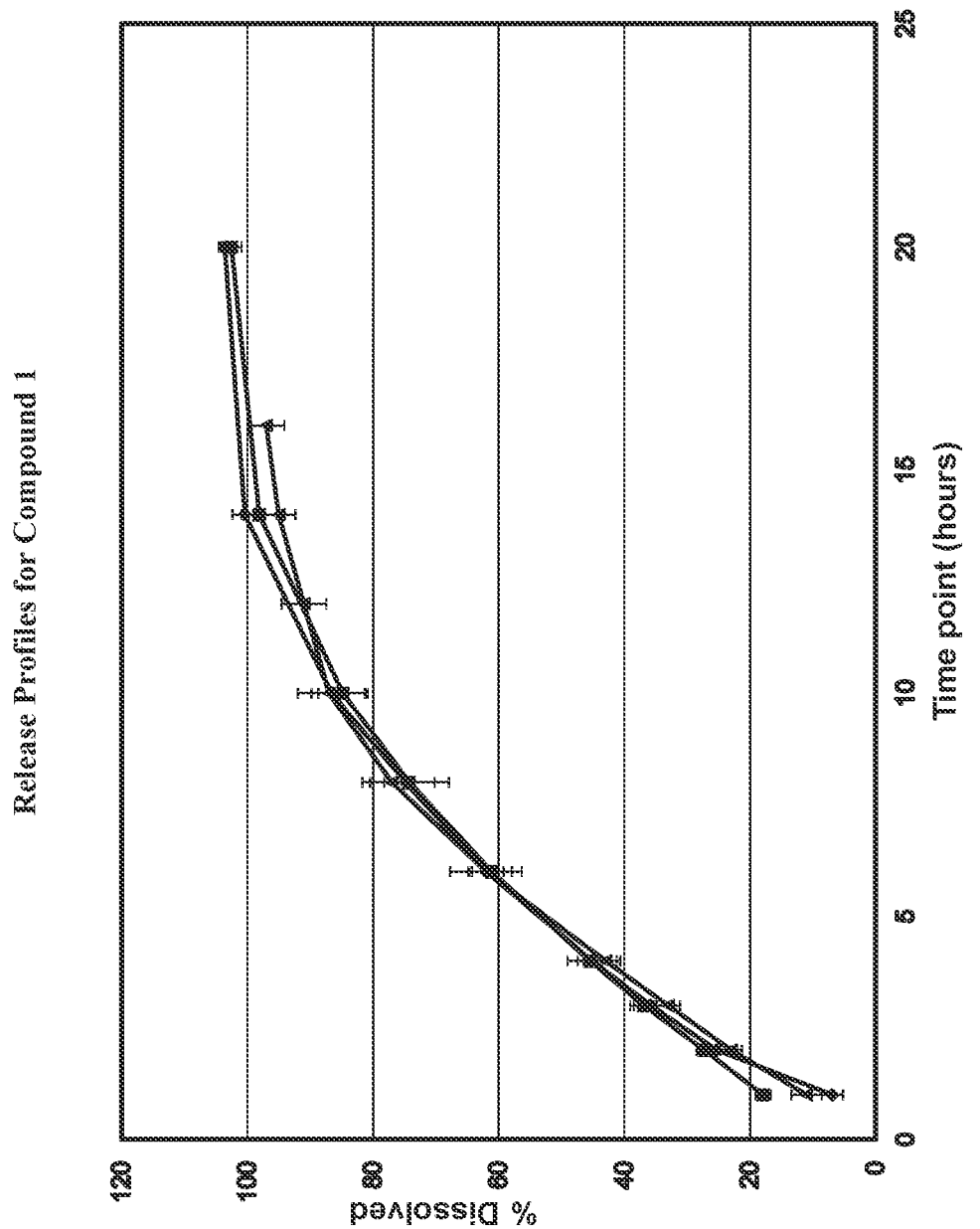
FIG. 14 shows dissolution profiles for: (a) (diamonds) a tablet comprising Compound 1 (0.05 mg), Methocel K4M Premium CR (25 mg), and Methocel 100 Premium LVCR (25 mg); (b) (squares) a tablet comprising Compound 1 (0.5 mg), Methocel K4M Premium CR (25 mg), and Methocel 100 Premium LVCR (25 mg); and (c) (triangles) a capsule comprising Compound 1 (0.03 mg), and Poloxamer 188 and food grade GMS in a ratio of 30:70 of Poloxamer 188 to food grade GMS. The points for each plot represent mean values. All three dissolution profiles were determined after storage at 40° C. and 75% RH for 6 months. Profiles (a) and (b) were determined using USP 1 (Baskets) at 100 rpm. Profile (c) was determined using USP 2 (Paddles) at 50 rpm.

Exemplary release profiles are shown in FIGS. 12-14. It is readily seen that in all three cases the release rate is substantially relative to that of the immediate-release formulation of FIG. 1. The release profile did not change significantly following storage over time. In particular, each of FIGS. 12 and 13 shows the initial release profile and the release profile after storage at 40° C. and 75% RH for six months. In each figure, at any time point equal to or greater than 2 hours, the percentage by weight of compound released in the initial release profile was found to be within 10% of the percentage by weight of compound released in the release profile after storage.

Examples of release rates (% by weight) are shown in Tables 6a-6d. All release profiles disclosed in Tables 6a-6d were measured with USP Apparatus 1 (baskets) at 100 rpm in 500 mL of aqueous sodium phosphate at a concentration of 0.05 M (pH=6.8). The values in a given table relate to tablets obtained from the same batch. Values shown represent mean values over a number of dissolution tests ("n" in each table) in each ease.

TABLE 6a

Initial release profile: % of Compound 1 that is released for a tablet containing 0.05 mg of Compound 1, 25 mg of Methocel K4M Premium CR and 25 mg of Methocel K100 Premium LVCR.

| | 60* | 120* | 180* | 240* | 360* | 480* | 600* | 840* |
|---|---|---|---|---|---|---|---|---|
| mean value (n = 6) of % of Compound 1 released | 6.9 | 25.3 | 35.8 | 45.1 | 62 | 74.8 | 86.6 | 100.4 |
| % RSD** | 1.7 | 2 | 3.3 | 3.9 | 5.7 | 6.9 | 5.3 | 2 |

*time in minutes

TABLE 6a-continued

Initial release profile: % of Compound 1 that is released for a tablet containing 0.05 mg of Compound 1, 25 mg of Methocel K4M Premium CR and 25 mg of Methocel K100 Premium LVCR.

| | 60* | 120* | 180* | 240* | 360* | 480* | 600* | 840* |
|---|---|---|---|---|---|---|---|---|

**RSD as a percentage of mean value of % of Compound 1 released

TABLE 6b

Initial release profile: % of Compound 1 that is released for a tablet containing 0.5 mg of Compound 1, 25 mg of Methocel K4M Premium CR and 25 mg of Methocel K100 Premium LVCR.

| | 60* | 120* | 180* | 240* | 360* | 480* | 600* | 840* |
|---|---|---|---|---|---|---|---|---|
| mean value (n = 6) of % of Compound 1 released | 17.9 | 27.3 | 36.9 | 45.5 | 61.1 | 74.2 | 84.8 | 98.1 |
| % RSD** | 1.2 | 1.2 | 1.6 | 1.9 | 3.2 | 4 | 3.9 | 2.8 |

*time in minutes
**RSD as a percentage of mean value of % of Compound 1 released

TABLE 6c

Release profile after storage at 40° C. and 75% RH for 6 months: % of Compound 1 that is released for a tablet containing 0.05 mg of Compound 1, 25 mg of Methocel K4M Premium CR and 25 mg of Methocel K100 Premium LVCR.

| | 60* | 120* | 180* | 240* | 360* | 480* | 600* | 840* |
|---|---|---|---|---|---|---|---|---|
| mean value (n = 6) of % of Compound 1 released | 17 | 27.1 | 36.9 | 45.4 | 61.1 | 75.8 | 86.9 | 100 |
| % RSD** | 2.3 | 2.5 | 3.2 | 4.3 | 5.1 | 3.7 | 2.5 | 1.4 |

*time in minutes
**RSD as a percentage of mean value of % of Compound 1 released

TABLE 6d

Release profile after storage at 40° C. and 75% RH for 6 months: % of Compound 1 that is released for a tablet containing 0.5 mg of Compound 1, 25 mg of Methocel K4M Premium CR and 25 mg of Methocel K100 Premium LVCR.

| | 60* | 120* | 180* | 240* | 360* | 480* | 600* | 840* |
|---|---|---|---|---|---|---|---|---|
| mean value (n = 6) of % of Compound 1 released | 6.8 | 24.3 | 33 | 41.3 | 55.5 | 67.9 | 79.4 | 94.7 |
| % RSD** | 2.4 | 2.8 | 4.3 | 5.6 | 7.5 | 8.3 | 6.7 | 4.3 |

*time in minutes
**RSD as a percentage of mean value of % of Compound 1 released

Example 7

Clinical Trials

A. An open-label, fixed sequence, non-randomized study in two cohorts of healthy male and non-pregnant, non-lactating female subjects was conducted. Two cohorts with twelve subjects in each were enrolled to ensure data in ten evaluable subjects per cohort.

Each subject in Cohort 1 received each of the following regimens, in the fasted state, in a sequential manner over four treatment periods:

Regimen A (0.03 mg mediate-release Compound 1): 1×0.03 mg Compound 1 immediate-release capsule, Regimen B (0.06 mg modified-release Compound 1): 1×0.06 mg Compound 1 modified-release tablet as disclosed herein.

Regimen C (0.12 mg modified-release Compound 1): 0.06 mg Compound 1 modified-release tablets as disclosed herein, Regimen D (0.18 mg modified-release Compound 1) 3×0.06 mg Compound 1 modified-release tablets as disclosed herein.

Subjects in Cohort 1 were considered evaluable if they received both 0.06 mg and 0.12 mg Compound 1 modified-release tablet doses and the reference Compound 1 immediate-release capsule.

Each subject in Cohort 2 received each of the following regimens, in the fasted state, in a sequential manner over three treatment periods:
  Regimen E (0.2 mg selexipag): 1×selexipag (Uptravi®) 200 μg film-coated tablet.
  Regimen F (0.4 mg selexipag): 2×selexipag (Uptravi®) 200 μg film-coated tablets.
  Regimen G (0.6 mg selexipag): 3×selexipag (Uptravi®) 200 μg film-coated tablets.

Subjects in Cohort 2 were considered evaluable if they received both the 0.2 mg and 0.4 mg doses of selexipag.

Subjects received each regimen in the morning of Day 1, following an overnight fast of a minimum of 8 hours. PK samples were taken from subjects at 72 hours post-dose. There was a minimum washout period of 7 days between each administration of investigational medicinal product (IMP) (i.e., selexipag film-coated tablet(s), Compound 1 immediate-release capsule(s), and/or Compound 1 modified-release tablet(s)).

For Cohort 1, subjects received Regimens A, B and C in a sequential manner at consecutive treatment periods. Subjects who tolerated the IMP in all prior regimens continued in the study to receive the final dose (Regimen D); subjects who did not tolerate the MP were considered to have completed the study and did not receive the final dose.

For Cohort 2, subjects received Regimens E and F in a sequential manner at consecutive treatment periods. Subjects who tolerated the IMP in all prior regimens continued in the study to receive the final dose (Regimen G); subjects who did not tolerate the IMP were considered to have completed the study and did not receive the final dose.

Pharmacokinetic Assessments:

Venous blood samples were withdrawn at regular time intervals. Plasma concentration data for Compound 1 and the selexipag parent and active metabolite were analyzed using appropriate non-compartmental techniques to obtain estimates of one or more of the following parameters:
  $T_{lag}$
  $T_{max}$
  $C_{max}$
  $C_{12}$
  $C_{24}$
  $AUC_{(0-last)}$
  $AUC_{(0-inf)}$
  AUC % extrap
  lambda-z
  T½el
  CL/F
  Frel: relative bioavailability of 0.06 mg Compound 1 tablets compared to the reference 0.03 mg Compound 1 capsule Pharmacodynamic Assessments:

Platelet aggregation was assessed for Regimen C and optional Regimen D in Cohort 1, and Regimen F and optional Regimen G in Cohort 2.

The following comparisons were estimated for Compound 1 and selexipag:
  Platelet aggregation (% change from baseline) versus time.
  Platelet aggregation versus plasma concentration.
  Effect maxima ($E_{max}$) and area under the effect curve (AUEC) for platelet aggregation (% change from baseline).

One or more of the above pharmacokinetic parameters were determined at one or more of the following time points: pre-dose and (referring to hours after administration): 0.5, 1, 1.5, 2, 3, 4, 5, 6, 8, 10, 12, 16, 20, 24, 36, 48, and 72 hours.

One or more of the above pharmacodynamic is parameters were determined at one or more of the following time points: pre-dose and (referring to hours after administration): 0.5, 1, 1.5, 2, 3, 4, 5, 6, 8, 10, 12, 16, 20, 24, 36, 48, and 72 hours.

Pharmacokinetic results showed that the modified-release tablet reduced the Cmax and increased Tmax while substantially maintaining similar total plasma concentrations. The most common treatment-emergent adverse events were similar to those seen in single ascending dose studies of Compound 1.

Following single oral administration of 0.06, 0.12 and 0.18 mg of the modified-release tablets of Compound 1, median Tmax occurred between approximately 4 and 10 hours. The geometric mean half-life ranged from approximately 19 to 23 hours across all dose levels.

Systemic exposure (Cmax and AUC) to Compound 1 following oral administration of the modified-release tablet formulation of Compound 1 increased in a slightly higher than dose-proportional manner.

Plasma concentrations at 24 hours post-dose were higher following administration of the modified-release tablet formulation of Compound 1, with an increase in line with the dose increase, compared to the immediate release-formulation.

Dose-adjusted peak plasma exposure ($C_{max}$/D) measures were lower for the modified-release compared to the immediate-release formulation [geometric mean ratios (GMRs) ranged from 28.7-41.2%]. Dose-adjusted total plasma exposure (AUC/D) measures ranged from similar to somewhat lower for modified-release compared to the immediate-release formulation (GMRs ranged from 63.3-97.9%). Relative bioavailability based on individual dose-adjusted peak plasma concentrations ($C_{max}$) was statistically significantly lower for 0.06, 0.12 and 0.18 mg of the modified-release tablet formulation of Compound 1 than the immediate-release capsule. Relative bioavailability based on individual dose-adjusted ratios of AUC(0-last) was statistically significantly lower than 0.06 and 0.12 mg of the modified-release tablet formulation of Compound 1, while 0.18 mg of the modified-release tablet formulation of Compound 1 demonstrated similar dose-adjusted total exposure (AUC(0-last)) compared to 0.03 mg of the immediate release capsule. Relative bioavailability based on individual dose-adjusted ratios of AUC(0-inf) showed a similar trend to AUC(0-last).

Overall, the modified-release tablet formulation of Compound 1 offers improved performance over the immediate-release capsule formulation for once daily dosing by extending drug exposure and minimizing $C_{max}$.

B. A second open-label, non-randomized pharmacokinetic study was conducted in healthy subjects. Fasted (cohort 1; n=19) or fed state (cohort 2, n=18) subjects received a modified-release tablet formulation of Compound 1 in a dose escalation sequence over 25 days (once daily dosing started at 0.06 mg and was slowly titrated, depending upon individual subject tolerability, by additional 0.06 mg dose increments every 5 days up to 0.3 mg once daily).

Two cohorts were enrolled to ensure data in 12 evaluable subjects per cohort.

Each subject received a once daily dose of the modified-release Compound 1 for 5 days, with up to four sequential dose escalations every 5 days:
  Regimen A (0.06 mg modified-release Compound 1): 1×0.06 mg Compound 1 modified-release tablet for 5 days Regimen B (0.12 mg modified-release Compound 1): 2×0.06 mg Compound 1 modified-release tablet for 5 days Regimen C (0.18 mg modified-release Compound 1): 3×0.06 mg Compound 1 modified-release tablet for 5 days Regimen 1) (0.24 mg modified-release Compound 1): 4×0.06 mg Compound 1 modified-release tablet for 5 days Regimen E (0.30 mg modified-release Compound 1): 5×0.06 mg Compound 1 modified-release tablet for 5 days Dose-dependent plasma exposure measures were observed for the modified-release tablet formulation given once daily, with low peak-trough fluctuation and little effect of food seen across dose levels. Somewhat higher mean plasma exposure measures were observed in females compared to males.

Accumulation index (5 days of dosing at 0.60 mg) was approximately 2.1-fold ($AUC_{(0-24)}$) in both the fed and fasted state. Exposure in the fed and fasted states was similar after single administration and at steady state, however, $T_{max}$ was delayed in the fed state. Peak exposure was significantly higher in female subjects than in male subjects, with an increase of greater than 42% for $C_{max}$, at steady state. However, differences in $AUC_{(0-24)}$ at steady state did not indicate a significant increase.

The modified-release tablet formulation of Compound 1 offered improved pharmacokinetic performance over both immediate-release capsules of Compound 1 and selexipag immediate-release tablet formulations by providing once daily dosing with extended drug exposure and low peak-trough fluctuation.

Example 8

Clinical Trial

A 22-week randomized, double-blind, placebo-controlled study with a dose titration period of up to 9 weeks was conducted. Sixty-one patients were randomized 2:1 Compound 1 to placebo, Right Heart Catheterization (RHC) measurements were obtained prior to study Day 1 of the dose titration period and at Week 22. The following values were obtained and recorded: pulmonary artery pressure (PAP) (systolic, diastolic, and mean), heart rate (FIR), right atrial pressure (RAP), pulmonary capillary wedge pressure (PCWP) right ventricular pressure (RVP) and cardiac output (CO), pulmonary vascular resistance (PVR), arterial and mixed venous oxygen saturation (FiO2) (if applicable). Systemic vascular resistance (SVR) was estimated from blood pressure measurements. The 6-minute walk test (6MWD) was conducted according to the modified guidelines issued by the American Thoracic Society, See Am J Respir Crit Care Med 166:111-117, 2002.

Primary efficacy endpoints for the study were: a) change from baseline in PVR after 22 weeks of treatment, and b) change from baseline in 6 MWD after 22 weeks of treatment.

Compound 1 was administered as a capsule in 0.01, 0.02, 0.03, 0.04, and 0.10 mg dose strengths. The formulation was supplied as a liquid-filled, size 4, hard-gelatin capsule containing Compound 1, polyoxyl 40 hydrogenated castor oil (Kolliphor® RH40) NF, butylated hydroxytoluene (BHT) NF, and colloidal silicon dioxide NE.

The starting dose of Compound 1 was 0.01 mg twice daily. The dose of Compound 1 was titrated according to patient tolerability. If the initial dose was tolerated (0.01 mg twice daily), then the dose was increased once a week in the following fashion: 0.02 mg twice daily, 0.03 mg twice daily, 0.04 mg twice daily, 0.06 Mg twice daily, 0.08 mg, 0.1 mg twice daily, 0.2 mg twice daily and 0.3 mg twice daily. The dose was optionally escalated to a possible maximum total daily dose of 0.6 mg (0.3 mg twice daily), pending tolerability. If a dose was not tolerated, Compound 1 was optionally decreased to the previous dose level. If the initial dose of 0.01 mg twice daily was not tolerated, dosing was optionally decreased to 0.01 mg once daily.

Subjects received concomitant oral disease-specific PAH therapy only if the dose remained stable for at least 3 months prior to the start of screening. This therapy consisted of the following: ERA and/or an agent acting on the NO pathway including the following: a PDE-5 inhibitor and a sGC stimulator, Subjects were instructed to continue the same dose and regimen of these medications for the duration of the study.

The use of the following therapies, which may affect PAH, was also permitted if the subject was on a stable dose for 1 month prior to screening and the dose remained unchanged through the duration of the study: vasodilators (including calcium channel blockers), digoxin, spironolactone, and L-arginine supplementation.

Doses of spironolactone and digoxin were held or reduced, if necessary, to protect the subject's safety, Doses were not allowed to be increased in the month before Day 1 and during the controlled study.

Diuretics were prescribed as clinically indicated throughout the study.

Additionally, the use of PDE-5 inhibitor as needed for erectile dysfunction (ED) was permitted as long as the subject had not taken a dose within 48 hours of any baseline or study-related efficacy assessment. In addition, the subject must not have taken more than 8 sildenafil tablets, 6 vardenafil, or 4 tadalafil tablets per month for ED.

Previous administration of a prostacyclin or prostacyclin analogue was not permitted if treatment was stopped for a safety or tolerability issue. In addition, intravenous inotropes within 1 month of screening were not permitted.

All subjects were taking PAH disease-specific medication. The majority of subjects were taking an ERA or PDE-5 inhibitor during the study for the treatment of PAH. Most subjects were on supportive therapy during the study.

Figure 15:
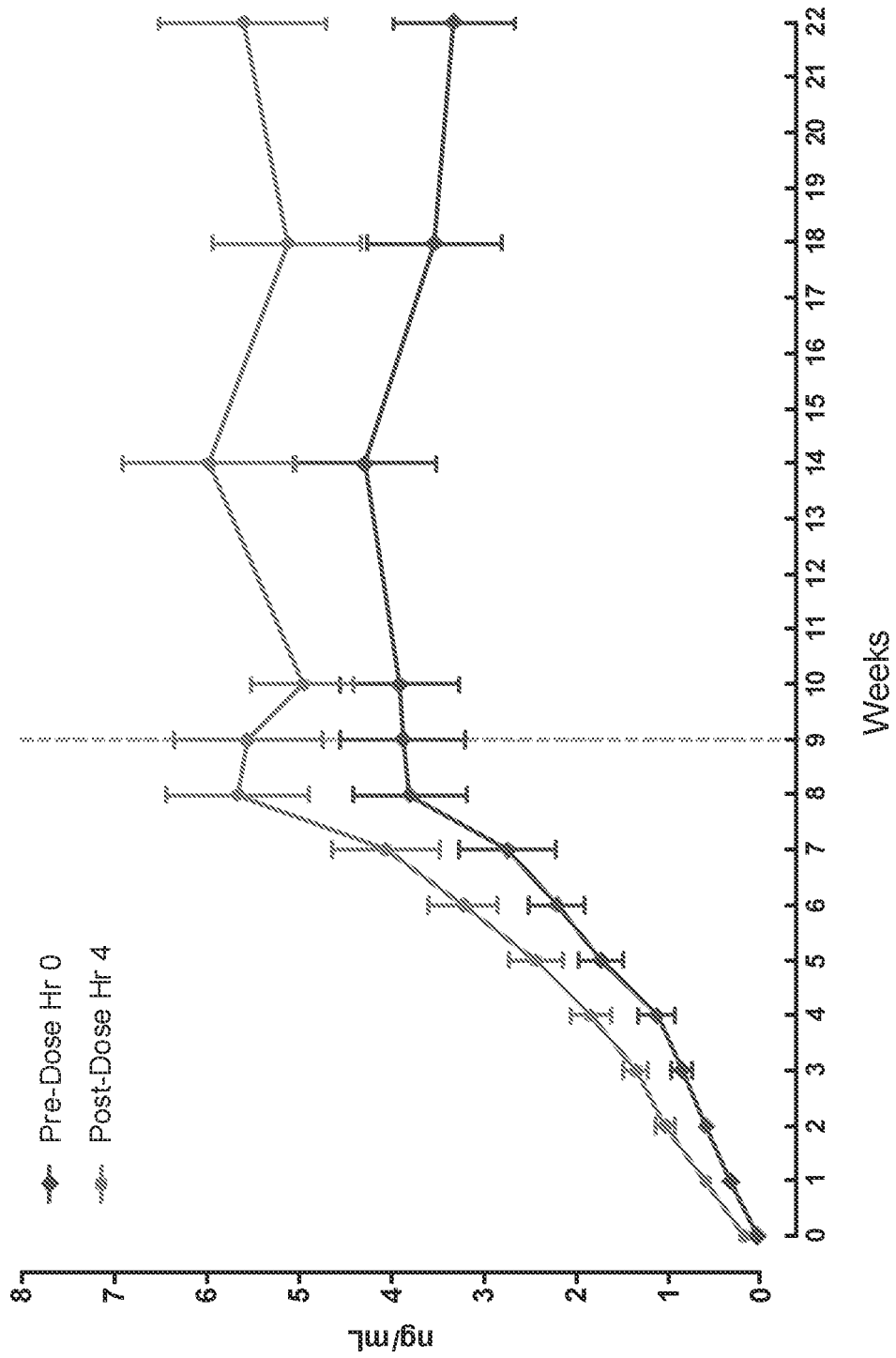
FIG. 15 shows the mean plasma concentration of Compound 1 measured pre-dose and at 4 hours post-dose in the clinical trial described in Example 8.

Compound 1 plasma levels were measured both pre-dose and at 4 hours post-dose. The mean concentration of Compound 1 over time is shown in FIG. 15. Mean pre-dose and 4 hours post-dose plasma concentrations continued to rise during the 9-week dose titration period. Thereafter, mean steady-state pre-dose and 4-hours post-dose plasma concentrations were maintained throughout the 13-week maintenance period. Overall, the observed mean pre-dose and 4-hours post-dose plasma levels of Compound 1 appear similar to those previously observed in healthy human subjects when administered the same dose regimen.

Compound 1 achieved the primary endpoint with a statistically significant change from baseline in pulmonary vascular resistance (PVR) compared to placebo. Compound 1 also demonstrated numerical improvement in 6-minute walk distance (6MWD). There was a strong and positive correlation between the 4 hour post-dose plasma concentrations of Compound 1 and percent change from baseline in PVR and 6MWD.

Adverse events observed in the study were consistent with other prostacyclin treatments for the management of PAH. The distribution of maintenance doses for patients receiving Compound 1 was as follows: 0.02 mg (n=1), 0.03 mg (n=1), 0.04 mg (n=0), 0.06 mg (n=3), 0.08 mg (n=3), 0.12 mg (n=5), 0.16 mg (n=4), 0.2 mg (n=6), 0.4 mg (n=12), and 0.6 mg (n=5).

Those skilled in the art will recognize that various modifications, additions, and substitutions to the illustrative examples set forth herein can be made without departing from the spirit of the invention and are, therefore, considered within the scope of the invention.

The invention claimed is:

1. A method for the treatment of pulmonary arterial hypertension (PAH) in a human, comprising administering to the human in need thereof, a pharmaceutical composition comprising 2-(((1r,4r)-4-(((4-chlorophenylxphenyl)carbamoyloxy)methyl)cyclohexyl)methoxy)acetic acid, having the structure:

(Compound 1)

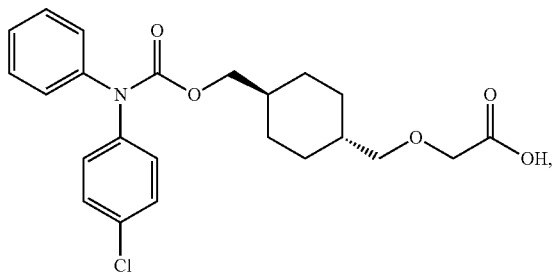

or a pharmaceutically acceptable salt, solvate, or hydrate thereof, in an amount equivalent to 0.01 mg to 1 mg of Compound 1,
  wherein the pharmaceutical composition is a tablet;
  wherein the tablet comprises a core and a coating;
  wherein the core consists of Compound 1, or a pharmaceutically acceptable salt, solvate, or hydrate thereof; a first release modifier; a second release modifier; at least one filler; at least one glidant; and at least one lubricant;
  wherein the first release modifier has a viscosity of 2300 mPA seconds to 3800 mPA seconds when present in an amount of about 2% in water at 20° C. and the second release modifier has a viscosity of 75 mPA seconds to 120 mPA seconds when present in an amount of about 2% in water at 20° C.
  wherein the first release modifier is present in the core in an amount equal to about 12.5% to about 37.5% by weight and the second release modifier is present in the core in an amount equal to about 12.5% to about 37.5% by weight;
  wherein the composition has a release rate by weight of the compound in an aqueous medium that is one or more of release rates (a), (b) and (c), wherein
    (a) less than or equal to 40% by weight of the compound is released over the first two hours in the aqueous medium;
    (b) 40% to 60% by weight of the compound is released over the first five hours in the aqueous medium; and
    (c) more than or equal to 80% by weight of the compound is released over the first fourteen hours in the aqueous medium,
  wherein the release rate is measured with USP Apparatus 1 (baskets) at 80 to 120 rpm in 400 to 600 mL of an aqueous medium at a pH of 6.3 to 7.3 at a temperature of 37° C.±0.5° C., comprising sodium phosphate at a concentration of 0.04 to 0.06 M.

2. The method of claim 1, wherein the first release modifier is hydroxypropyl methylcellulose.

3. The method of claim 2, wherein the second release modifier is hydroxypropyl methylcellulose.

4. The method of claim 1, wherein the first release modifier is present in an amount equal to about 25% by weight and the second release modifier is present in an amount equal to about 25% by weight.

5. The method of claim 1, wherein the compound is 2-(((1r,4r)-4-(((4-chlorophenyl)(phenyl)carbamoyloxy)methyl)cyclohexyl)methoxy)acetic acid 6 (Compound 1).

6. The method of claim 5, wherein Compound 1 is present in an 7 amount from 0.01% to 1% by weight of the pharmaceutical composition.

7. The method of claim 5, wherein Compound 1 is present in an 8 amount from 0.01% to 0.6% by weight of the pharmaceutical composition.

8. The method of claim 5, wherein Compound 1 is present in an amount selected from 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg.

9. The method of claim 1, wherein Compound 1 is present in an amount selected from 0.05 mg, 0.25 mg and 0.4 mg.

10. The method of claim 1, wherein the core consists of Compound 1, the first release modifier, the second release modifier, silicon dioxide, magnesium stearate, mannitol, and microcrystalline cellulose.

11. The method of claim 1, wherein the coating does not comprise hydroxypropyl methylcellulose.

12. The method of claim 1, wherein the tablet has a total weight of 98 mg to 110 mg.

13. The method of claim 1, wherein the release rate is the release rate measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M.

14. The method of claim 1, wherein the pharmaceutical composition is storage-stable.

15. The method of claim 14, wherein the pharmaceutical composition is storage-stable and the release rate of the compound after storage of the composition at 40° C. and 75% RH for at least one month does not vary at any given dissolution time point equal or greater than 2 hours by more than 20% of the release rate of the compound prior to storage, wherein the release rate after storage and prior to storage are each measured with USP Apparatus 1 (baskets) at 100 rpm in 500 mL of an aqueous medium at a pH of 6.8 at a temperature of 37° C.±0.5° C., wherein the aqueous medium comprises sodium phosphate at a concentration of 0.05 M.

16. The method of claim 1, wherein the pharmaceutical composition is administered once daily.

17. The method of claim 1, wherein the PAH is selected from: idiopathic PAH (IPAH); familial PAH (FPAH); PAH associated with other conditions (APAH); and PAH associated with significant venous or capillary involvement.

18. The method of claim 17, wherein the APAH is PAH associated with collagen vascular disease, PAH associated with congenital systemic-to-pulmonary shunts, PAH associated with portal hypertension, PAH associated with HIV infection, PAH associated with drugs or toxins, PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, or PAH associated with splenectomy.

19. The method of claim 1, wherein the PAH is PAH associated with pulmonary veno-occlusive disease (PVOD) or PAH associated with pulmonary capillary hemangiomatosis (PCH).

20. A method for the treatment of pulmonary arterial hypertension (PAH) in a human, comprising administering to the human in need thereof, a pharmaceutical composition comprising 2-(((1r,4r)-4-(((4-chlorophenyl)(phenyl)carbamoyloxy)methyl)cyclohexyl)methoxy)acetic acid, having the structure:

(Compound 1)

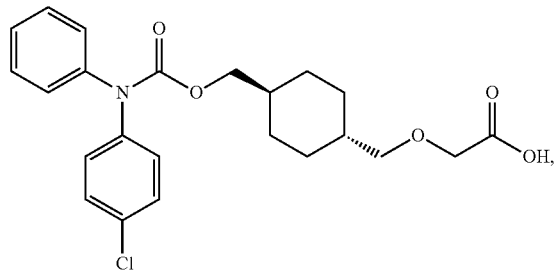

wherein the composition is a tablet comprising a core and a coating; wherein the core consists of 0.01 mg to 0.8 mg of Compound 1; 5 mg to 45 mg of hydroxypropyl methylcellulose having a viscosity of 2300 mPA seconds to 3800 mPA seconds when present in an amount of about 2% in water at 20° C.; 5 mg to 45 mg of hydroxypropyl methylcellulose having a viscosity of 75 mPA seconds to 120 mPA seconds when present in an amount of about 2% in water at 20° C.; at least one filler; at least one glidant; and at least one lubricant.

21. A method for the treatment of pulmonary arterial hypertension (PAH) in a human, comprising administering to the human in need thereof, a pharmaceutical composition comprising 2-(((1r,4r)-4-(((4-chlorophenyl)(phenyl)carbamoyloxy)methyl)cyclohexyl)methoxy)acetic acid, having the structure:

(Compound 1)

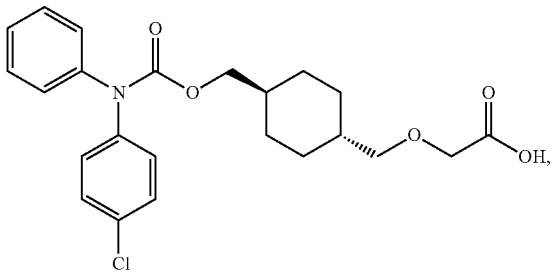

wherein the composition is a tablet comprising a core and a coating; wherein the core consists of 0.01 mg to 0.8 mg of Compound 1; 25 mg of hydroxypropyl methylcellulose having a viscosity of 2300 mPA seconds to 3800 mPA seconds when present in an amount of about 2% in water at 20° C.; 25 mg of hydroxypropyl methylcellulose having a viscosity of 75 mPA seconds to 120 mPA seconds when present in an amount of about 2% in water at 20° C.; at least one filler; at least one glidant; and at least one lubricant.

22. The method of claim 1, wherein treatment of pulmonary arterial hypertension comprises ameliorating symptoms of PAH, arresting further development of symptoms of PAH, or both.

23. The method of claim 22, wherein the symptoms of pulmonary arterial 24 hypertension comprise dyspnea, angina, syncope or edema, or combinations thereof.

24. The method of claim 20, wherein treatment of pulmonary arterial hypertension comprises ameliorating symptoms of PAH, arresting further development of symptoms of PAH, or both.

25. The method of claim 24, wherein the symptoms of pulmonary arterial hypertension comprise dyspnea, angina, syncope or edema, or combinations thereof.

* * * * *